United States Patent
Kennedy et al.

(10) Patent No.: US 7,250,444 B2
(45) Date of Patent: Jul. 31, 2007

(54) PYRROLE-BASED HMG-COA REDUCTASE INHIBITORS

(75) Inventors: Robert Michael Kennedy, Ann Arbor, MI (US); William Keun-Chan Park, Ann Arbor, MI (US); Bruce David Roth, Plymouth, MI (US); Yuntao Song, Ann Arbor, MI (US); Bharat K. Trivedi, Farmington Hills, MI (US)

(73) Assignee: Pfizer Inc., New York, NY (US)

( * ) Notice: Subject to any disclaimer, the term of this patent is extended or adjusted under 35 U.S.C. 154(b) by 360 days.

(21) Appl. No.: 10/862,844

(22) Filed: Jun. 7, 2004

(65) Prior Publication Data

US 2005/0043364 A1  Feb. 24, 2005

Related U.S. Application Data

(60) Provisional application No. 60/494,216, filed on Aug. 11, 2003.

(51) Int. Cl.
*A61K 31/40* (2006.01)
*C07D 207/00* (2006.01)

(52) U.S. Cl. ............... 514/427; 514/340; 548/518; 548/560; 548/562

(58) Field of Classification Search ........... 548/560, 548/518, 562; 546/276.4; 514/427, 340
See application file for complete search history.

(56) References Cited

U.S. PATENT DOCUMENTS

| | | | |
|---|---|---|---|
| 3,983,140 A | 9/1976 | Endo et al. | |
| 4,049,495 A | 9/1977 | Endo et al. | |
| 4,137,322 A | 1/1979 | Endo et al. | |
| 4,198,425 A | 4/1980 | Mistui et al. | |
| 4,255,444 A | 3/1981 | Oka et al. | |
| 4,262,013 A | 4/1981 | Mistui et al. | |
| 4,375,475 A | 3/1983 | Willard et al. | |
| 4,681,893 A | 7/1987 | Roth | |
| 4,851,427 A | 7/1989 | Wareing | |
| 5,055,484 A | 10/1991 | Jendrall et al. | |
| 5,091,386 A | 2/1992 | Kesseler et al. | |
| 5,385,929 A | 1/1995 | Bjorge et al. | |
| 6,479,490 B2 * | 11/2002 | Gong et al. ............ | 514/235.5 |

FOREIGN PATENT DOCUMENTS

| | | |
|---|---|---|
| EP | 0221025 | 5/1987 |
| WO | WO 01/52829 A2 | 7/2001 |
| WO | WO 2004/005250 A1 | 1/2004 |

OTHER PUBLICATIONS

Selling, H.A., et al. Acetylenic Sulfinamides: A Novel Class of Compounds, Synthietic Communications; 1976 ,6 (2), p. 129-134.
Babin,,P., et al. Electrophillic Properties of Sulphamyl Chloride. Application to the Synthesis of alpha beta-Acetylenic Sulphonamides; J. Chem Research 1982, 1, p. 16-17.
Baudin, J. B., et al, A Simpe and Effiecient Preparation of N,n-Disubstituted (1-Alkyne)- or (E)-(1-Alkene)sulfinamides and their Conversion into the Correspnding Sulfinates or Sulfonamides; Synlett, 11, 1992, pp. 911-913.
Hlasta, D. J., et al., Steric Effects on teh Regioselectivity of Azide-Alkyne Dipolar Cycloaddition Reaction: The Sysnthesis fo Humah Leukocyte Elastase Inhibitors; J. Organic Chem, 1994, 59, pp. 6184-6189.
Procopiou, P.A., et al, Inhibitors of Cholesterol Biosynthese 2. 3-5Dihydroxy-7-(N-pyrrolyl)-6-heptenoates, a Novel Series of HMG-CoA Reductase Inhibitors, J of Medical Chem., 1993, 36, pp. 3658-3662.
Ansell, J. et. al., hsCRP and HDL Effects of Statins Trial (CHEST): Rapid Effect of Statin Therapy on C-Reative Protein and High-Density Lipoprotein Levels; Heart Disease, 2003, 5, p. 2-7.
Beaird, S, et al., HMG-CoA Reductase Inhibitors: Assessing Differences in Drug Interactions and Safety Profiles; Journal of the American Pharmaceutical Assoc., 2004, vol. 40, No. 5, p. 637-644.
Lipid Research Clinics Program, The Lipid Research Clinics Corionary Primary Previention Trial Results; Journal of American Medical Assoc.,1984, vol.251, No. 3, p. 351-374.
Takemoto, M., et. al., Pleiotropic Effects of 3-Hyrdroxy-3-Methylglutaryl Coenzyme A. Redutase Inhibitors; Arterioscler Throm Vasc Biol., 2001, vol. 21, p. 1712-1713.
Bottorff, M., et. al., Long-term Safety of Hepatic Hydroxymethl Glutaryl Coenzyme a Reductase Inhibitors; Arch. Intern. Med, 2000, vol. 160, p. 2273-2280.
McTaggart, F., et. al., Preclinical and Clinical Pharmacology of Rosuvastation, a New-Hydroxy-3-Methylglutaryl Coenzyme A. Reductase Inhibitor; 2001 vol. 87 (suppl) p. 28B-32B.
Hulcher, F., et. al., Inhibition of Hepatic Cholesterol Biosynthesis by 3-5 Hydroxy-3,4,4-Trimethylvaleric Acid and Its Site of Action; Archives of Biochemistry and Biophyics 1971, vol. 146, p. 422-427.
Brown, M. et. al., Lowering Plasma Cholesterol by Raising LDL Receptors, New England Journal of Medicine, 1981, vol. 305, No. 9, p. 515-517.
Singer, F., et. al., New Inhibitors of in vitro Conversion of Acetate and Mevalonate to Cholesterol; Proc. Soc. Exper. Biol. Med., 1959, vol. 102, 370-373.
Brown, A., et al., Crystal and Molecular Structure of Compaction, a New Antifugal Metabolite from *Penicillium breviocmpactum*; Journal of Chem. Soc. Perkin I, 1976, 1165-1170.
McKenney, J. et al, Pharmacologic Characteristics of Statins, Clin Cardiol, 2003, vol. 26 (suppl. III), pp. III-32-III-38.
Chapman, M. et al, Optimizing the pharmacology of statins: characteristics of rosuvastatin, Atherosclerosis Supplements 2, 2002, pp. 33-37.
Roth, B., et al, Inhibitors of Cholesterol Biosynthesis . . . ; Journal of Medicinal Chemistry, 1991, vol. 34, pp. 357-366.
Graul, A., et al, Atorvastatin Calcium Hypolipidemic HMG-CoA Reductase Inhibitor, Drugs of the Future, 1997, vol. 22, No. 9, pp. 956-968.
Jahng, Y., et al, Design of a new class of HMG-CoA reductase inhibitors, Drugs of the Future, 1995, vol. 20, No. 4, pp. 387-404.

* cited by examiner

*Primary Examiner*—Kamal A. Saeed
*Assistant Examiner*—Rei-tsang Shiao
(74) *Attorney, Agent, or Firm*—Gregg C. Benson; Rona A. Nardone

(57) ABSTRACT

HMGCo-A reductase inhibitor compounds useful as hypocholesterolemic and hypolipidemic compounds are provided. Also provided are pharmaceutical compositions of the compounds. Methods of making and methods of using the compounds are also provided.

34 Claims, No Drawings

PYRROLE-BASED HMG-COA REDUCTASE INHIBITORS

This present application claims priority under 35 U.S.C. section 119(e) to U.S. Provisional Application Ser. No. 60/494,216, filed Aug. 11, 2003.

FIELD OF THE INVENTION

The present invention relates to compounds and pharmaceutical compositions useful as hypocholesterolemic and hypolipidemic agents. More specifically, the present invention relates to certain potent inhibitors of the enzyme 3-hydroxy-3-methylglutaryl-coenzyme A reductase ("HMG-CoA Reductase"). The invention further relates to methods of using such compounds and compositions to treat subjects, including humans, suffering from hyperlipidemia, hypercholesterolemia, hypertriglyceridemia, Alzheimer's disease, benign prostatic hypertrophy (BPH), osteoporosis and atherosclerosis.

BACKGROUND OF THE INVENTION

High levels of blood cholesterol and blood lipids are conditions involved in the onset of atherosclerosis. The conversion of HMG-CoA to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents. Thus, statins are the drugs of first choice for management of many lipid disorders. Representative statins include atorvastatin, lovastatin, pravastatin, rosuvastatin and simvastatin.

It is known that inhibitors of HMG-CoA reductase are effective in lowering the blood plasma level of low density lipoprotein cholesterol (LDL-C), in man. (cf. M. S. Brown and J. L. Goldstein, *New England Journal of Medicine*, 305, No. 9, 515-517 (1981)). It has been established that lowering LDL-C levels affords protection from coronary heart disease (cf. *Journal of the American Medical Association*, 251, No. 3, 351-374 (1984)). Further, it is known that certain derivatives of mevalonic acid (3,5-dihydroxy-3-methylpentanoic acid) and the corresponding ring-closed lactone form mevalonolactone, inhibit the biosynthesis of cholesterol (cf. F. M. Singer et al., *Proc. Soc. Exper. Biol. Med.*, 102: 370 (1959) and F. H. Hulcher, *Arch. Biochem. Biophys.*, 146: 422 (1971)). U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown et al., *J. Chem. Soc. Perkin* I (1976) 1165). U.S. Pat. No. 4,255,444 to Oka et al. discloses several synthetic derivatives of mevalonolactone having antilipidemic activity. U.S. Pat. Nos. 4,198,425 and 4,262,013 to Mitsue et al. disclose aralkyl derivatives of mevalonolactone which are useful in the treatment of hyperlipidemia.

U.S. Pat. No. 4,375,475 to Willard et al. discloses certain substituted 4-hydroxytetrahydropyran-2-ones which, in the 4(R)-trans-steroisomeric form, are inhibitors of cholesterol biosynthesis.

Published PCT application No. WO 84/01231 discloses certain indole analogs and derivatives of mevalonolactone having utility as hypolipoproteinemic and antiatherosclerotic agents.

Atorvastatin and pharmaceutically acceptable salts thereof are selective, competitive inhibitors of HMG-CoA reductase. As such, atorvastatin calcium is a potent lipid lowering compound and is thus useful as a hypolipidemic and/or hypocholesterolemic agent, as well as in the treatment of osteoporosis and Alzheimer's disease. A number of patents have issued disclosing atorvastatin. These include: U.S. Pat. Nos. 4,681,893; 5,273,995 and 5,969,156, which are incorporated herein by reference.

All statins interfere, to varying degrees, with the conversion of HMG-CoA to the cholesterol precursor mevalonate by HMG-CoA reductase. These drugs share many features, but also exhibit differences in pharmacologic attributes that may contribute to differences in clinical utility and effectiveness in modifying lipid risk factors for coronary heart disease. (Clin. Cardiol. Bol. 26 (Suppl. III), III-32-III-38 (2003)). Some of the desirable pharmacologic features with statin therapy include potent reversible inhibition of HMG-CoA reductase, the ability to produce large reductions in LDL-C and non-high-density lipoprotein cholesterol (non-HDL-C), the ability to increase HDL cholesterol (HDL-C), tissue selectivity, optimal pharmacokinetics, availability of once a day dosing and a low potential for drug-drug interactions. Also desirable is the ability to lower circulating very-low-density-lipoprotein (VLDL) as well as the ability to lower triglyceride levels.

At the present time, the most potent statins display in vitro $IC_{50}$ values, using purified human HMG-CoA reductase catalytic domain preparations, of between about 5.4 and about 8.0 nM. *Am J. Cardiol* 2001; 87(suppl):28B-32B; *Atheroscer Suppl.* 2002; 2:33-37. Generally, the most potent LDL-C-lowering statins are also the most potent non-HDL-C-lowering statins. Thus, maximum inhibitory activity is desirable. With respect to HDL-C, the known statins generally produce only modest increases in HDL-C. Therefore, the ability to effect greater increases in HDL-C would be advantageous as well.

With respect to tissue selectivity, differences among statins in relative lipophilicity or hydrophilicity may influence drug kinetics and tissue selectivity. Relatively hydrophilic drugs may exhibit reduced access to nonhepatic cells as a result of low passive diffusion and increased relative hepatic cell uptake through selective organic ion transport. In addition, the relative water solubility of a drug may reduce the need for extensive cytochrome P450 (CYP) enzyme metabolism. Many drugs, including the known statins, are metabolized by the CYP3A4 enzyme system. *Arch Intern Med* 2000; 160:2273-2280; *J Am Pharm Assoc* 2000; 40:637-644. Thus, relative hydrophilicity is desirable with statin therapy.

Two important pharmacokinetic variables for statins are bioavailability and elimination half-life. It would be advantageous to have a statin with limited systemic availability so as to minimize any potential risk of systemic adverse effects, while at the same time having enough systemic availability so that any pleiotropic effects can be observed and maximized with statin treatment. These pleiotropic effects include improving or restoring endothelial function, enhancing the stability of atherosclerotic plaques, reduction in blood plasma levels of certain markers of inflammation such as C-reactive protein, decreasing oxidative stress and reducing vascular inflammation. *Arterioscler Thromb Vasc Biol.* 2001; 21:1712-1719; *Heart Dis* 5 (1):2-7, 2003. Further, it would be advantageous to have a statin with a long enough elimination half-life to maximize effectiveness for lowering LDL-C.

Finally, it would be advantageous to have a statin that is either not metabolized or minimally metabolized by the CYP 3A4 systems so as to minimize any potential risk of drug-drug interactions when statins are given in combination with other drugs.

Accordingly, it would be most beneficial to provide a statin having a combination of desirable properties including high potency in inhibiting HMG-CoA reductase, the ability to produce large reductions in LDL-C and non-high density lipoprotein cholesterol, the ability to increase HDL cholesterol, selectivity of effect or uptake in hepatic cells, optimal systemic bioavailability, prolonged elimination half-life, and absence or minimal metabolism via the CYP3A4 system.

SUMMARY OF THE INVETION

This invention provides a novel series of N-alkyl pyrroles as HMG-CoA reductase inhibitors. Compounds of the invention are potent-inhibitors of cholesterol biosynthesis. Accordingly, the compounds find utility as therapeutic agents to treat hyperlipidemia, hypercholesterolemia, hypertriglyceridemia and atherosclerosis. More specifically, the present invention provides a compound having a Formula I,

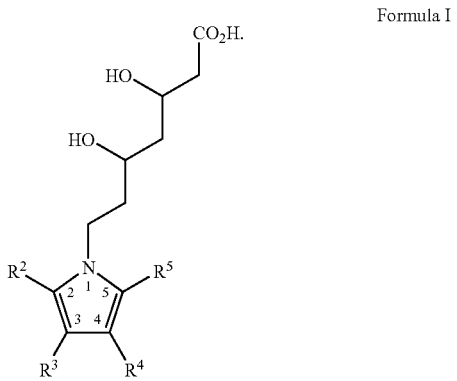

Formula I or a pharmaceutically acceptable salt, ester, amide, stereoisomer or prodrug thereof, or a pharmaceutically acceptable salt of the prodrug, wherein $R^2$ is benzyl, naphthyl or cyclohexyl, optionally substituted; phenyl or phenyl substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; one of $R^3$ and $R^4$ is H; aryl, aralkyl, heteroaryl, heteroaralkyl, optionally substituted; $C_1$-$C_8$ alkyl straight chain or branched; or $C_3$-$C_8$ cycloalkyl; and the other one of $R^3$ and $R^4$ is H, I, COOR', $R^6R^7$NC(O)— or $SO_2NR^9R^{10}$; one of $R^6$ and $R^7$ is $SO_2NHR^8$ or $SO_2R^8$; and the other one of $R^6$ and $R^7$ is H or $C_1$-$C_4$ alkyl; $R^8$ is aryl or heteroaryl, optionally substituted; $R^9$ and $R^{10}$ are each independently H; aryl, aralkyl, heteroaryl or heteroaralkyl optionally substituted with halogen, OR', $(CH_2)_n$COOR', $(CH_2)_n$CONR'R''', $(CH_2)_n$SO$_2$NR'R''', $(CH_2)_n$SO$_2$R' or CN; $C_1$-$C_{10}$ alkyl unsubstituted or substituted with OH, CO$_2$R' or CONR'R''; or N, $R^9$ and $R^{10}$ taken together form a 4-11 member ring optionally containing up to 2 heteroatoms selected from O, N and S, said ring optionally substituted with =O, OH, benzyl, phenyl, CO$_2$R', R'OR'', $(CH_2)_n$SO$_2$R' or CONR'R''; $R^5$ is alkyl of from one to four carbon atoms, optionally substituted with a halogen; R' and R'' are each independently H, lower alkyl or taken together form a 4-7 member ring; and n is 0-2.

The present invention provides the compounds: (3R,5R)-7-[2,3-Bis-(4-fluoro-phenyl)-5-isopropyl-4-methylsulfamoyl-pyrrol-1-yl]-3,5-dihydroxy-heptanoic acid; (3R,5R)-7-[2,3-Bis-(4-fluoro-phenyl)-5-isopropyl-pyrrol-1-yl]-3,5-dihydroxy-heptanoic acid; (3R,5R)-7-[3-Benzylsulfamoyl-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-4-(2-hydroxy-phenylsulfamoyl)-5-isopropyl-pyrrol-1-yl]-3,5-dihydroxy-heptanoic acid; (3R,5R)-7-[2,3-Bis-(4-fluoro-phenyl)-5-isopropyl-4-phenylsulfamoyl-pyrrol-1-yl]-3,5-dihydroxy-heptanoic acid; 4-[1-((3R,5R)-6-Carboxy-3,5-dihydroxy-hexyl)-4,5-bis-(4-fluoro-phenyl)-2-isopropyl-1H-pyrrole-3-sulfonylamino]-benzoic acid; 1-[1-((3R,5R)-6-Carboxy-3,5-dihydroxy-hexyl)-4,5-bis-(4-fluoro-phenyl)-2-isopropyl-1H-pyrrole-3-sulfonyl]-piperidine-4-carboxylic acid; (3R,5R)-7-[2,3-Bis-(4-fluoro-phenyl)-5-isopropyl-4-(2-methoxycarbonyl-ethylsulfamoyl)-pyrrol-1-yl]-3,5-dihydroxy-heptanoic acid; (3R,5R)-7-[2,3-Bis-(4-fluoro-phenyl)-5-isopropyl-4-(3-methoxycarbonyl-propylsulfamoyl)-pyrrol-1-yl]-3,5-dihydroxy-heptanoic acid; (3R,5R)-7-[3-(2,4-Difluoro-phenylsulfamoyl)-4,5-bis-(4-fluoro-phenyl)-2-isopropyl-pyrrol-1-yl]-3,5-dihydroxy-heptanoic acid; (3R,5R)-7-[3-Carbamoyl-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-5-isopropyl-4-(toluene-4-sulfonylaminocarbonyl)-pyrrol-1-yl]-3,5-dihydroxy-heptanoic acid; (3R,5R)-7-[2,3-Bis-(4-fluoro-phenyl)-4-(2-hydroxy-ethylsulfamoyl)-5-isopropyl-pyrrol-1-yl]-3,5-dihydroxy-heptanoic acid; 4-{[1-((3R,5R)-6-Carboxy-3,5-dihydroxy-hexyl)-5-(4-fluoro-phenyl)-2-isopropyl-4-phenyl-1H-pyrrole-3-carbonyl]-amino}-benzoic acid; (3R,5R)-7-[3-(4-Cyano-phenyl)-2-(4-fluoro-phenyl)-5-isopropyl-4-phenylcarbamoyl-pyrrol-1-yl]-3,5-dihydroxy-heptanoic acid; (3R,5R)-7-[3-(4-Bromo-phenyl)-2-(4-fluoro-phenyl)-5-isopropyl-4-phenylcarbamoyl-pyrrol-1-yl]-3,5-dihydroxy-heptanoic acid; (3R,5R)-7-[3-(3,4-Difluoro-phenyl)-2-(4-fluoro-phenyl)-5-isopropyl-4-phenylcarbamoyl-pyrrol-1-yl]-3,5-dihydroxy-heptanoic acid; 4-{[1-((3R,5R)-6-Carboxy-3,5-dihydroxy-hexyl)-5-(4-fluoro-phenyl)-2-isopropyl-4-phenyl-1H-pyrrole-3-carbonyl]-amino}-benzoic acid; (3R,5R)-7-[2,3-Bis-(4-fluoro-phenyl)-4-(2-hydroxy-phenylsulfamoyl)-5-isopropyl-pyrrol-1-yl]-3,5-dihydroxy-heptanoic acid; (3R,5R)-7-[2-(4-Fluoro-phenyl)-5-isopropyl-3-naphthalen-2-yl-4-phenylcarbamoyl-pyrrol-1-yl]-3,5-dihydroxy-heptanoic acid; (3R,5R)-7-[3-Cyclopropyl-2-(4-fluoro-phenyl)-5-isopropyl-4-phenylcarbamoyl-pyrrol-1-yl]-3,5-dihydroxy-heptanoic acid; (3R,5R)-7-[3-(4-Dimethylcarbamoyl-phenylcarbamoyl)-5-(4-fluoro-phenyl)-2-isopropyl-4-phenyl-pyrrol-1-yl]-3,5-dihydroxy-heptanoic acid; (3R,5R)-7-[2-(4-Fluoro-phenyl)-4-iodo-5-isopropyl-3-phenyl-pyrrol-1-yl]-3,5-dihydroxy-heptanoic acid; (3R,5R)-7-[3-(4-Diethylcarbamoyl-phenylcarbamoyl)-5-(4-fluoro-phenyl)-2-isopropyl-4-phenyl-pyrrol-1-yl]-3,5-dihydroxy-heptanoic acid; (3R,5R)-7-[2-(4-Fluoro-phenyl)-5-isopropyl-4-(4-methylcarbamoyl-phenylcarbamoyl)-3-phenyl-pyrrol-1-yl]-3,5-dihydroxy-heptanoic acid; (3R,5R)-7-[2-(4-Fluoro-phenyl)-5-isopropyl-4-phenylcarbamoyl-3-pyridin-4-yl-pyrrol-1-yl]-3,5-dihydroxy-heptanoic acid; (3R,5R)-7-[4-Benzylcarbamoyl-2-(4-fluoro-phenyl)-5-isopropyl-imidazol-1-yl]-3,5-dihydroxy-heptanoic acid; (3R,5R)-7-[2,3-Bis-(4-fluoro-phenyl)-4-(2-fluoro-phenylsulfamoyl)-5-isopropyl-pyrrol-1-yl]-3,5-dihydroxy-heptanoic acid; (3R,5R)-7-[2,3-Bis-(4-fluoro-phenyl)-4-(3-hydroxy-phenylsulfamoyl)-5-isopropyl-pyrrol-1-yl]-3,5-dihydroxy-heptanoic acid; (3R,5R)-7-[3-(4-Carbamoyl-phenylsulfamoyl)-4,5-bis-(4-fluoro-phenyl)-2-isopropyl-pyrrol-1-yl]-3,5-dihydroxy-heptanoic acid; (3R,5R)-7-[2-Ethyl-5-(4-fluoro-phenyl)-4-isopropyl-3-phenylcarbamoyl-pyrrol-1-yl]-3,5-dihydroxy-heptanoic acid; (3R,5R)-7-[2,3-Bis-(4-fluoro-phenyl)-5-isopropyl-4-(4-sulfamoyl-phenylsulfamoyl)-pyrrol-1-yl]-3,5-dihydroxy-heptanoic acid; (3R,5R)-7-[2-(4-Fluoro-phenyl)-3,5-diisopropyl-4-phenylcarbamoyl-pyrrol-1-yl]-3,5-dihydroxy-heptanoic acid; (3R,5R)-7-[2-Ethyl-5-(4-fluoro-phenyl)-4-phenethyl-3-phenylcarbamoyl-pyrrol-1-yl]-3,5-dihydroxy-heptanoic acid; (3R,5R)-7-[3-Benzylcarbamoyl-2-ethyl-5-(4-fluoro-phenyl)-4-isopropyl-pyrrol-1-yl]-3,5-dihydroxy-heptanoic acid; (3R,5R)-7-[2-(4-Fluoro-phenyl)-5-isopropyl-4-(morpholine-4-sulfonyl)-3-phenyl-pyrrol-1-yl]-3,5-dihydroxy-heptanoic acid; (3R,5R)-7-[3-(Benzyl-methyl-sulfamoyl)-4,5-bis-(4-fluoro-phenyl)-2-isopropyl-pyrrol-1-yl]-3,5-dihydroxy-heptanoic acid; (3R,5R)-7-[3-(Benzyl-methyl-sulfamoyl)-5-(4-fluoro-phenyl)-2-isopropyl-4-p-tolyl-pyrrol-1-yl]-3,5-dihydroxy-heptanoic acid; (3R,5R)-7-[3-(Benzyl-methyl-sulfamoyl)-5-(4-fluoro-phenyl)-2-isopropyl-4-naphthalen-2-yl-pyrrol-1-yl]-3,5-dihydroxy-heptanoic acid; (3R,5R)-7-[3-(4-Benzyl-piperidine-1-sulfonyl)-5-(4-fluoro-phenyl)-2-isopropyl-4-phenyl-pyrrol-1-yl]-3,5-dihydroxy-heptanoic acid; (3R,5R)-7-[2-Ethyl-5-methyl-4-(5-methyl-pyridin-2-ylcarbamoyl)-3-p-tolyl-pyrrol-1-yl]-3,5-dihydroxy-heptanoic acid; (3R,5R)-7-(2,5-Dimethyl-3-naphthalen-2-yl-4-phenylcarbamoyl-pyrrol-1-yl)-3,5-dihydroxy-heptanoic acid; (3R,5R)-7-[2-Ethyl-5-methyl-4-(5-methyl-pyridin-2-ylcarbamoyl)-3-naphthalen-2-yl-pyrrol-1-yl]-3,5-dihydroxy-heptanoic acid; (3R,5R)-7-(2-Ethyl-5-methyl-3-phenyl-4-phenylcarbamoyl-pyrrol-1-yl)-3,5-dihydroxy-heptanoic acid; (3R,5R)-7-(3-Benzylcarbamoyl-2,5-dimethyl-4-phenyl-pyrrol-1-yl)-3,5-dihydroxy-heptanoic acid; (3R,5R)-7-(3-Benzylcarbamoyl-2,5-dimethyl-4-p-tolyl-pyrrol-1-yl)-3,5-dihydroxy-heptanoic acid; (3R,5R)-7-(3-benzylcarbamoyl-2,5-dimethyl-4-naphthalen-2-yl-pyrrol-1-yl)-3,5-dihydroxy-heptanoic acid; (3R,5R)-7-(3-Benzylcarbamoyl-5-ethyl-2-methyl-4-phenyl-pyrrol-1-yl)-3,5-dihydroxy-heptanoic acid; (3R,5R)-7-[2-ethyl-4-(2-methoxy-ethylcarbamoyl)-3-(4-methoxy-phenyl)-5-methyl-pyrrol-1-yl]-3,5-dihydroxy-heptanoic acid; (3R,5R)-7-(3-benzylcarbamoyl-5-ethyl-2-methyl-4-p-tolyl-pyrrol-1-yl)-3,5-dihydroxy-heptanoic acid; (3R,5R)-7-[2-Ethyl-4-(2-methoxy-ethylcarbamoyl)-5-methyl-3-naphthalen-2-yl-pyrrol-1-yl]-3,5-dihydroxy-heptanoic acid; (3R,5R)-7-[3-benzylcarbamoyl-5-ethyl-4-(4-methoxy-phenyl)-2-methyl-pyrrol-1-yl]-3,5-dihydroxy-heptanoic acid; (3R,5R)-7-(3-Benzylcarbamoyl-5-ethyl-2-methyl-4-naphthalen-2-yl-pyrrol-1-yl)-3,5-dihydroxy-heptanoic acid; (3R,5R)-7-(2,5-Dimethyl-3-phenethylcarbamoyl-4-phenyl-pyrrol-1-yl)-3,5-dihydroxy-heptanoic acid; (3R,5R)-3,5-Dihydroxy-7-(3-isobutylcarbamoyl-2,5-dimethyl-4-phenyl-pyrrol-1-yl)-heptanoic acid; (3R,5R)-3,5-Dihydroxy-7-(3-isobutylcarbamoyl-2,5-dimethyl-4-p-tolyl-pyrrol-1-yl)-heptanoic acid; (3R,5R)-7-(2-Ethyl-4-isobutylcarbamoyl-5-methyl-3-p-tolyl-pyrrol-1-yl)-3,5-dihydroxy-heptanoic acid; (3R,5R)-7-(2,5-Dimethyl-3-phenethylcarbamoyl-4-p-tolyl-pyrrol-1-yl)-3,5-dihydroxy-heptanoic acid; (3R,5R)-7-(2-benzyl-5-methyl-3-phenyl-4-phenylcarbamoyl-pyrrol-1-yl)-3,5-dihydroxy-heptanoic acid; (3R,5R)-7-[3-(4-Chloro-phenyl)-5-isopropyl-2-methyl-4-phenylcarbamoyl-pyrrol-1-yl]-3,5-dihydroxy-heptanoic acid; (3R,5R)-3,5-Dihydroxy-7-(2-methyl-4,5-diphenyl-3-phenylcarbamoyl-pyrrol-1-yl)-heptanoic acid; (3R,5R)-7-[2-(4-fluoro-phenyl)-4-iodo-5-isopropyl-3-phenyl-pyrrol-1-yl]-3,5-dihydroxy-heptanoic acid; (3R,5R)-7-[3-(4-Carbamoyl-phenylsulfamoyl)-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-5-isopropyl-4-(4-sulfamoyl-phenylsulfamoyl)-pyrrol-1-yl]-3,5-dihydroxy-heptanoic acid; (3R,5R)-7-[2-(4-Fluoro-phenyl)-5-isopropyl-4-(morpholine-4-sulfonyl)-3-phenyl-pyrrol-1-yl]-3,5-dihydroxy-heptanoic acid; (3R,5R)-7-[3-(Benzyl-methyl-sulfamoyl)-5-(4-fluoro-phenyl)-2-isopropyl-4-naphthalen-2-yl-pyrrol-1-yl]-3,5-dihydroxy-heptanoic acid; (3R,5R)-7-[3-(4-Benzyl-piperidine-1-sulfonyl)-5-(4-fluoro-phenyl)-2-isopropyl-4-phenyl-pyrrol-1-yl]-3,5-dihydroxy-heptanoic acid; 7-[3-(3-Aza-spiro[5.5] undecane-3-sulfonyl)-4,5-bis-(4-fluoro-phenyl)-2-isopropyl-pyrrol-1-yl]-3,5-dihydroxy-heptanoic acid; 7-[2,3-Bis-(4-fluoro-phenyl)-4-(4-hydroxy-piperidine-1-sulfonyl)-5-isopropyl-pyrrol-1-yl]-3,5-dihydroxy-heptanoic acid; 7-[2,3-Bis-(4-fluoro-phenyl)-5-isopropyl-4-(pyrrolidine-1-sulfonyl)-pyrrol-1-yl]-3,5-dihydroxy-heptanoic acid; 7-[2,3-Bis-(4-fluoro-phenyl)-4-(2-hydroxymethyl-pyrrolidine-1-sulfonyl)-5-isopropyl-pyrrol-1-yl]-3,5-dihydroxy-heptanoic acid; 7-[2,3-Bis-(4-fluoro-phenyl)-4-(3-hydroxy-pyrrolidine-1-sulfonyl)-5-isopropyl-pyrrol-1-yl]-3,5-dihydroxy-heptanoic acid; 7-[2,3-Bis-(4-fluoro-phenyl)-5-isopropyl-4-(3-phenyl-pyrrolidine-1-sulfonyl)-pyrrol-1-yl]-3,5-dihydroxy-heptanoic acid; 7-[2,3-Bis-(4-fluoro-phenyl)-5-isopropyl-4-(3-methanesulfonyl-pyrrolidine-1-sulfonyl)-pyrrol-1-yl]-3,5-dihydroxy-heptanoic acid; 7-[2,3-Bis-(4-fluoro-phenyl)-4-(3-hydroxy-pyrrolidine-1-sulfonyl)-5-isopropyl-pyrrol-1-yl]-3,5-dihydroxy-heptanoic acid; 7-[3-Diphenylsulfamoyl-4,5-bis-(4-fluoro-phenyl)-2-isopropyl-pyrrol-1-yl]-3,5-dihydroxy-heptanoic acid; 7-[2,3-Bis-(4-fluoro-phenyl)-5-isopropyl-4-(thiomorpholine-4-sulfonyl)-pyrrol-1-yl]-3,5-dihydroxy-heptanoic acid; 7-[3-(1,1-Dioxo-1l6-thiomorpholine-4-sulfonyl)-4,5-bis-(4-fluoro-phenyl)-2-isopropyl-pyrrol-1-yl]-3,5-dihydroxy-heptanoic acid; 7-[3-(2,6-Dimethyl-morpholine-4-sulfonyl)-4,5-bis-(4-fluoro-phenyl)-2-isopropyl-pyrrol-1-yl]-3,5-dihydroxy-heptanoic acid; 7-[2,3-Bis-(4-fluoro-phenyl)-5-isopropyl-4-(octahydro-isoquinoline-2-sulfonyl)-pyrrol-1-yl]-3,5-dihydroxy-heptanoic acid;

and pharmaceutically acceptable salts, esters and amides thereof.

Further, the present invention provides a process for making a compound having a Formula 10

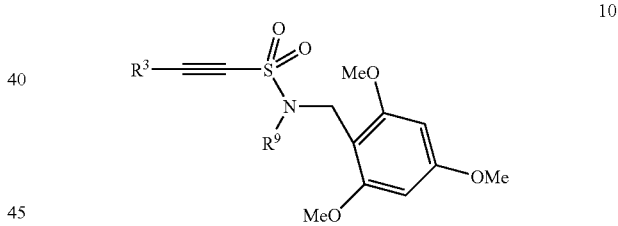

wherein $R^9$ is aryl, aralkyl, heteroaryl or heteroaralkyl; optionally substituted; $C_1$-$C_{10}$ alkyl unsubstituted or substituted with OH, $CO_2R'$ or $CONR'R''$; and $R^3$ is aryl, aralkyl, heteroaryl, heteroaralkyl, optionally substituted; $C_1$-$C_8$ alkyl straight chain or branched; or $C_3$-$C_8$ cycloalkyl;

comprising the following steps: 1.) reacting a compound having a Formula 1

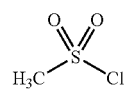

with $R^9$-substituted 2,4,6-trimethoxy benzylaniline, wherein $R^9$ is as defined above, to form a compound of Formula 8 wherein Me is methyl and $R^9$ is as defined above,

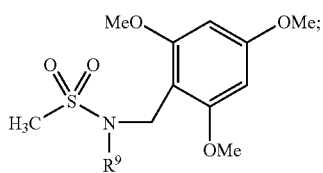

2.) reacting the compound of Formula 8 with a compound having a Formula $R^3$COOMe wherein $R^3$ and Me are as defined above, is in n-BuLi, to form a compound of Formula 9

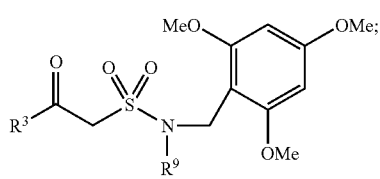

wherein Me is methyl and $R^3$ and $R^9$ are as defined above; and

3.) contacting the compound 9 with 2-chloro N-methylpyridinium iodide and triethylamine to form the compound 10.

The present invention further provides a compound having a Formula 15

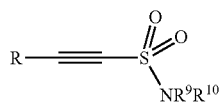

wherein R is $C_1$-$C_8$ alkyl straight chain or branched or $C_3$-$C_8$ cycloalkyl;

$R^9$ and $R^{10}$ are each independently H; aryl, aralkyl, heteroaryl or heteroaralkyl;

optionally substituted; $C_1$-$C_{10}$ alkyl unsubstituted or substituted with OH, $CO_2R'$ or CONR'R''; or N, $R^9$ and $R^{10}$ taken together form a 4-7 member ring, optionally containing up to 2 heteroatoms selected from O, N and S, said ring optionally substituted with OH, benzyl, phenyl, $CO_2R'$ or CONR'R''; and R' and R'' are each independently H, lower alkyl or taken together form a 4-7 member ring.

The present invention also provides a compound having a formula C,

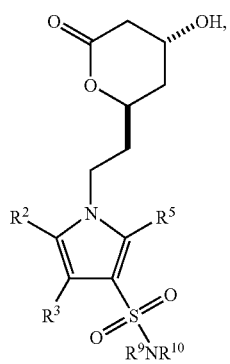

wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; $R^3$ is H; aryl, aralkyl, heteroaryl, heteroaralkyl, optionally substituted; $C_1$-$C_8$ alkyl straight chain or branched; or $C_3$-$C_8$ cycloalkyl;

$R^5$ is alkyl of from one to four carbon atoms, optionally substituted with a halogen; and $R^9$ and $R^{10}$ are each independently H; aryl, aralkyl, heteroaryl or heteroaralkyl optionally substituted with halogen, OR', $(CH_2)_n$COOR', $(CH_2)_n$CONR'R'', $(CH_2)_n$SO$_2$NR'R'', $(CH_2)_n$SO$_2$R' or CN; $C_1$-$C_{10}$ alkyl unsubstituted or substituted with OH, $CO_2R'$ or CONR'R'';

or N, $R^9$ and $R^{10}$ taken together form a 4-7 member ring optionally containing up to 2 heteroatoms selected from O, N and S, said ring optionally substituted with OH, benzyl, phenyl, $CO_2R'$ or CONR'R'';

$R^5$ is alkyl of from one to four carbon atoms, optionally substituted with a halogen; R' and R'' are each independently H, lower alkyl or taken together form a 4-7 member ring; and n is 0-2.

The present invention also provides a compound having a Formula,

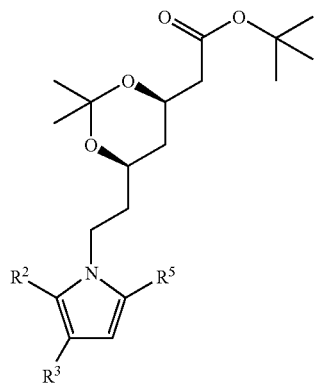

or a pharmaceutically acceptable salt, ester, amide, stereoisomer or prodrug thereof or a pharmaceutically acceptable salt of the prodrug wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; $R^3$ is H; aryl, aralkyl, heteroaryl, heteroaralkyl, optionally substituted; $C_1$-$C_8$ alkyl straight chain or branched; or $C_3$-$C_8$ cycloalkyl; and $R^5$ is alkyl of from one to four carbon atoms, optionally substituted with a halogen.

The present invention also provides a compound having a formula

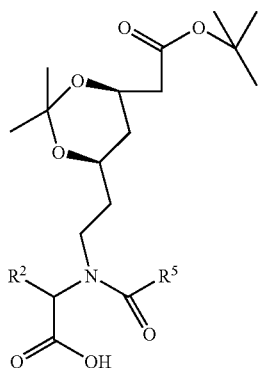

wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; and $R^5$ is alkyl of from one to four carbon atoms, optionally substituted with a halogen.

DETAILED DESCRIPTION OF THE INVENTION

The present invention provides a compound having a Formula I,

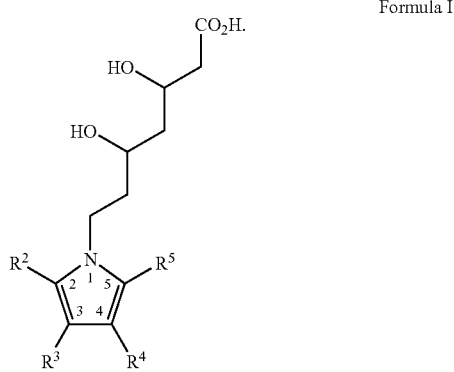

Formula I or a pharmaceutically acceptable salt, ester, amide, stereoisomer or prodrug thereof, or a pharmaceutically acceptable salt of the prodrug, wherein $R^2$ is benzyl, naphthyl or cyclohexyl, optionally substituted; phenyl or phenyl substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; one of $R^3$ and $R^4$ is H; aryl, aralkyl, heteroaryl, heteroaralkyl, optionally substituted; $C_1$-$C_8$ alkyl straight chain or branched; or $C_3$-$C_8$ cycloalkyl; and the other one of $R^3$ and $R^4$ is H, I, COOR', $R^6R^7NC(O)$— or $SO_2NR^9R^{10}$; one of $R^6$ and $R^7$ is $SO_2NHR^8$ or $SO_2R^8$; and the other one of $R^6$ and $R^7$ is H or $C_1$-$C_4$ alkyl; $R^8$ is aryl or heteroaryl, optionally substituted; $R^9$ and $R^{10}$ are each independently H; aryl, aralkyl, heteroaryl or heteroaralkyl optionally substituted with halogen, OR', $(CH_2)_n$ COOR', $(CH_2)_nCONR'R''$, $(CH_2)_nSO_2NR'R''$, $(CH_2)_n$ $SO_2R'$ or CN; $C_1$-$C_{10}$ alkyl unsubstituted or substituted with OH, $CO_2R'$ or CONR'R''; or N, $R^9$ and $R^{10}$ taken together form a 4-11 member ring optionally containing up to 2 heteroatoms selected from O, N and S, said ring optionally substituted with =O, OH, benzyl, phenyl, $CO_2R'$, R'OR'', $(CH_2)_n$ $SO_2R'$ or CONR'R''; $R^5$ is alkyl of from one to four carbon atoms, optionally substituted with a halogen; R' and R'' are each independently H, lower alkyl or taken together form a 4-7 member ring; and n is 0-2.

Further provided is the above-described compound wherein $R^2$ is phenyl or substituted phenyl. Further provided is the compound wherein $R^2$ is phenyl substituted with a halogen. Further provided is the compound wherein $R^2$ is para-fluorophenyl.

Further provided is the above-described compound wherein $R^3$ is indolyl, phenyl, biphenyl or substituted phenyl, pyridyl or substituted pyridyl, lower alkyl, or naphthyl.

Further provided is the above compound wherein $R^3$ is cyclohexyl-, clyclopentyl-, cyclobutyl-, cyclopropyl-, methyl-, ethyl-, isopropyl-, difluoromethyl, trifluoro-methyl or phenyl substituted with one or more halogen.

Further provided is the compound wherein $R^3$ is para-fluorophenyl, 3,4-difluorophenyl, para-cyanophenyl or para-methylphenyl.

Further provided is the above described compound wherein $R^5$ is $C_1$-$C_4$ alkyl. Further provided is the compound wherein $R^5$ is $C_{1-3}$ alkyl.

Further provided is the above compound wherein $R^4$ is $SO_2NR^9R^{10}$.

Further provided is the above compound wherein $R^9$ and $R^{10}$ are each independently H, methyl, phenyl or phenyl substituted with OH, F, $CO_2R'$, CONR'R'', $SO_2NR'R''$ or one or more halogen; or benzyl or benzyl substituted with OH, $CO_2R'$ or CONR'R''.

Further provided is the above compound wherein $R^5$ is isopropyl, ethyl, trifluoromethyl or difluoromethyl.

Further provided is the compound wherein $R^5$ is isopropyl and $R^2$ is para-fluorophenyl.

Further provided is a pharmaceutically acceptable salt of the above compound wherein the salt is a sodium salt or a calcium salt.

Further provided is a sterioisomer of the above compound comprising a (3R, 5R)-isomer.

Further provided is a sterioisomer of the above compound comprising a (3S, 5R)-isomer.

Further provided is a sterioisomer of the above compound comprising a (3R, 5S)-isomer.

Further provided is a sterioisomer of the above compound comprising a (3S, 5S)-isomer.

Further provided is a pharmaceutically acceptable ester of the above compound wherein the ester is a methyl ester.

Further provided is the above-described compound wherein $R^5$ is isopropyl.

Further provided is the above compound wherein $R^2$ and $R^3$ are each independently phenyl or substituted phenyl and $R^5$ is $C_1$-$C_4$ alkyl.

Further provided is the compound wherein $R^5$ is $C_1$-$C_4$ alkyl and $R^4$ is $SO_2NR^9R^{10}$. Further provided is the compound wherein $R^5$ is $C_1$-$C_4$ alkyl, $R^4$ is $SO_2NR^9R^{10}$ and $R^9$ and $R^{10}$ are each independently H, Me, phenyl substituted with OH, F, $CO_2R'$, $SO_2NR'R''$ or CONR'R'', benzyl or benzyl substituted with OH, F, $CO_2R'$ or CONR''.

Further provided is the above compound wherein $R^8$ is phenyl or substituted phenyl.

Further provided is the above compound wherein N, $R^9$ and $R^{10}$ taken together form a 4-7 member ring, optionally containing up to 2 heteroatoms selected form O, N, and S, said ring optionally substituted with OH, benzyl, phenyl, $CO_2R'$ or $CONR'R''$; and $R'$ and $R''$ are each independently H, lower alkyl or taken together form a 4-7 member ring.

Further provided are pharmaceutical compositions of compounds of the present invention.

Further provided is a method of inhibiting cholesterol biosynthesis in a mammal requiring inhibition, comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of lowering LDL cholesterol in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of raising HDL cholesterol in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of treating, preventing or controlling hyperlipidemia in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of treating, preventing or controlling hypercholesterolemia in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of treating, preventing or controlling hypertriglyceridemia in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of treating, preventing or controlling atherosclerosis in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further provided is a method of treating, preventing or controlling Alzheimer's disease, BPH, diabetes or osteoporosis in a mammal comprising administering to the mammal in need thereof a therapeutically effective amount of a compound of the present invention or the pharmaceutically acceptable salt, ester, amide or prodrug thereof, or the pharmaceutically acceptable salt of the prodrug.

Further, the present invention provides a process for making a compound having a Formula 10

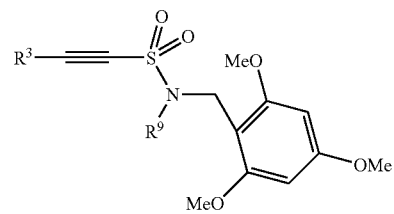

wherein $R^9$ is aryl, aralkyl, heteroaryl or heteroaralkyl; optionally substituted; $C_1$-$C_{10}$ alkyl unsubstituted or substituted with OH, $CO_2R'$ or $CONR'R''$; and $R^3$ is aryl, aralkyl, heteroaryl, heteroaralkyl, optionally substituted; $C_1$-$C_8$ alkyl straight chain or branched; or $C_3$-$C_8$ cycloalkyl;

comprising the following steps: 1.) reacting a compound having a Formula 1

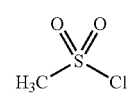

with $R^9$-substituted 2,4,6-trimethoxy benzylaniline, wherein $R^9$ is as defined above, to form a compound of Formula 8 wherein Me is methyl and $R^9$ is as defined above,

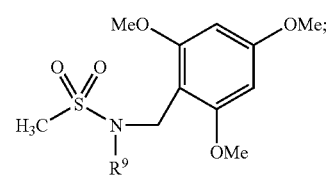

2.) reacting the compound of Formula 8 with a compound having a Formula $R^3COOMe$ wherein $R^3$ and Me are as defined above, is in n-BuLi, to form a compound of Formula 9

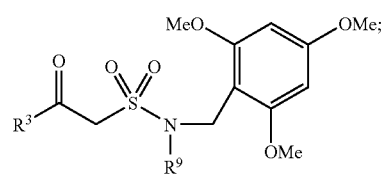

wherein Me is methyl and $R^3$ and $R^9$ are as defined above; and

3.) contacting the compound 9 with 2-chloro N-methylpyridinium iodide and triethylamine to form the compound 10.

The present invention further provides a compound having a Formula 15

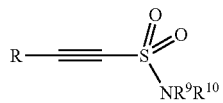

wherein R is $C_1$-$C_8$ alkyl straight chain or branched or $C_3$-$C_8$ cycloalkyl;

$R^9$ and $R^{10}$ are each independently H, aryl, aralkyl, heteroaryl or heteroaralkyl; optionally substituted; $C_1$-$C_{10}$ alkyl unsubstituted or substituted with OH, $CO_2R'$ or CONR'R''; or N, $R^9$ and $R^{10}$ taken together form a 4-7 member ring, optionally containing up to 2 heteroatoms selected from O, N and S, said ring optionally substituted with OH, benzyl, phenyl, $CO_2R'$ or CONR'R''; and R' and R'' are each independently H, lower alkyl or taken together form a 4-7 member ring. 45.

Further provided is a process for making a compound having a Formula 15 wherein R, $R^9$ and $R^{10}$ are as defined above

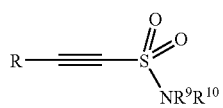

comprising the following steps: 1.) reacting a compound of Formula 1

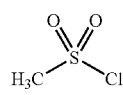

with $NR^9R^{10}$ wherein $R^9$ and $R^{10}$ are as defined above, to form a compound of Formula 13, wherein $R^9$ and $R^{10}$ are as defined above,

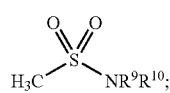

2.) reacting the compound 13 with RCOOMe wherein R is as defined above and Me is methyl, in n-BuLi, to form a corresponding β-ketosulfonamide; 3.) reacting said corresponding β-ketosulfonamide with a Hunig's base to form the compound 15.

Further provided is a process for making a compound having a Formula cc

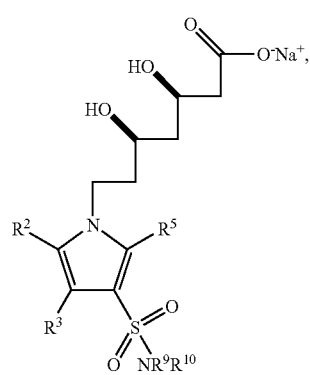

wherein $R^2$, $R^3$, $R^5$, $R^9$ and $R^{10}$ are as defined above, comprising the following steps: 1.) reacting a compound of Formula a, wherein $R^3$, $R^9$ and $R^{10}$ are as defined above, in a solvent,

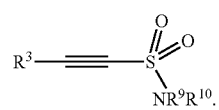

with a compound of Formula 5, wherein $R^2$ and $R^5$ are as defined above

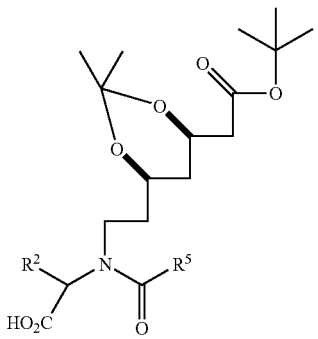

to form a compound of Formula b wherein $R^2$, $R^3$, $R^5$, $R^9$ and $R^{10}$ are as defined above;

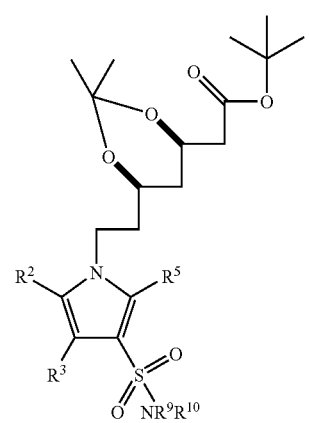

2.) forming a lactone corresponding to the compound b; and
3) hydrolyzing the lactone to form the compound cc.

Further provided is a process for making a compound having a Formula 12a

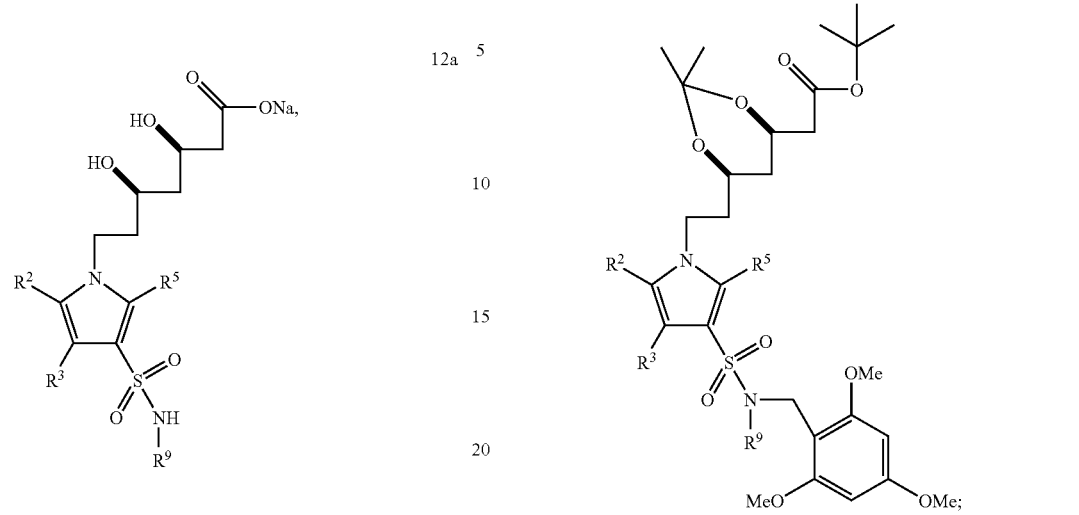

wherein $R^2$, $R^3$ and $R^5$ are as defined in claim 1 and $R^9$ is aryl, aralkyl, heteroaryl or heteroaralkyl; optionally substituted; or $C_{1-10}$ alkyl, optionally sukbstituted, comprising the following steps: 1.) reacting a compound of Formula 5 wherein $R^2$ and $R^5$ are as defined above,

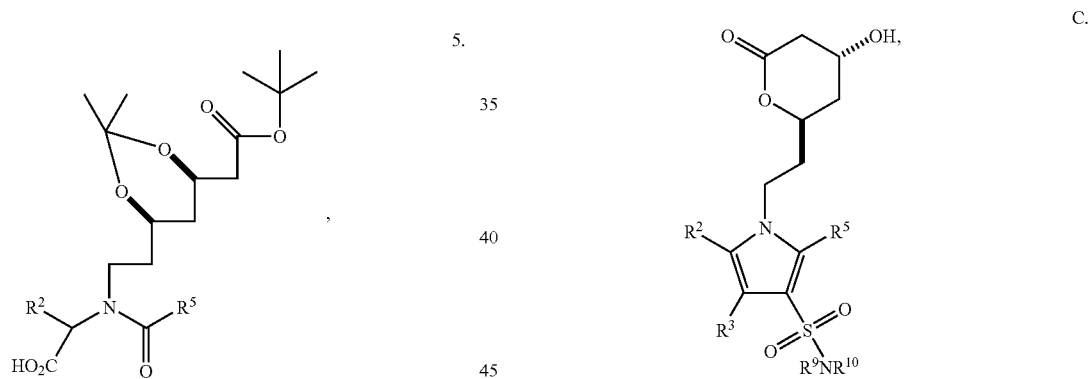

with a compound of Formula 10 wherein Me is methyl, $R^3$ and $R^9$ are as defined above,

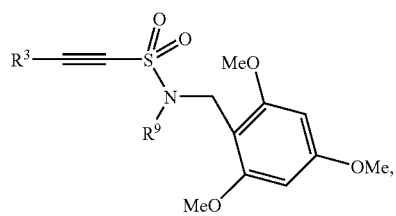

to form a compound of Formula 11 comprising a 2,4,6 trimethoxybenzyl protecting group, wherein $R^2$, $R^3$, $R^5$ and $R^9$ are as defined above, 2.) forming a lactone corresponding to the compound 11; 3) removing the protecting group; and 4.) hydrolyzing the lactone to produce the compound 12.

The present invention also provides a compound having a formula C, wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; $R^3$ is H; aryl, aralkyl, heteroaryl, heteroaralkyl, optionally substituted; $C_1$-$C_8$ alkyl straight chain or branched; or $C_3$-$C_8$ cycloalkyl;
$R^5$ is alkyl of from one to four carbon atoms, optionally substituted with a halogen; and $R^9$ and $R^{10}$ are each independently H; aryl, aralkyl, heteroaryl or heteroaralkyl optionally substituted with halogen, OR', $(CH_2)_n$COOR', $(CH_2)_n$CONR'R", $(CH_2)_n$SO$_2$NR'R", $(CH_2)_n$SO$_2$R' or CN; $C_1$-$C_{10}$ alkyl unsubstituted or substituted with OH, CO$_2$R' or CONR'R";
or N, $R^9$ and $R^{10}$ taken together form a 4-7 member ring optionally containing up to 2 heteroatoms selected from O, N and S, said ring optionally substituted with OH, benzyl, phenyl, CO$_2$R' or CONR'R";

$R^5$ is alkyl of from one to four carbon atoms, optionally substituted with a halogen; R' and R" are each independently H, lower alkyl or taken together form a 4-7 member ring; and n is 0-2.

The present invention further provides a process for making a compound having a formula C

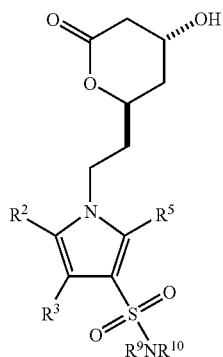

C., wherein $R^2$, $R^3$, $R^5$, $R^9$ and $R^{10}$ are as defined above, comprising the following steps:

1). Reacting a compound A,

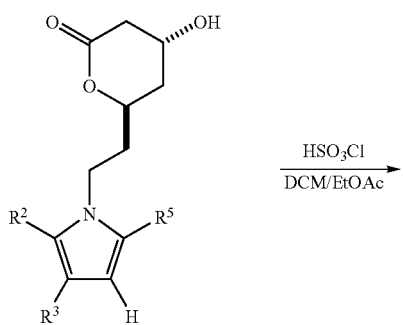

wherein $R^2$; $R^3$ and $R^5$ are as defined above with HSO$_3$Cl in DCM/EtOA$_C$ to form a compound B,

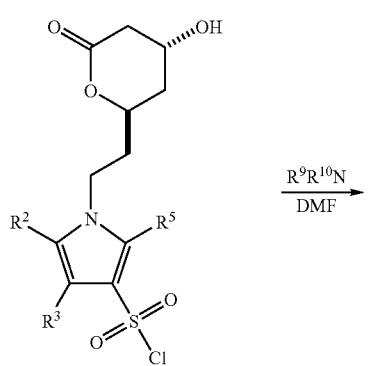

wherein $R^2$, $R^3$ and $R^5$ are as defined above; and 2.) reacting the compound B with $R^9R^{10}$N wherein $R^9$ and $R^{10}$ are as defined above in DMF to form the compound C.

The present invention also provides a compound having a Formula,

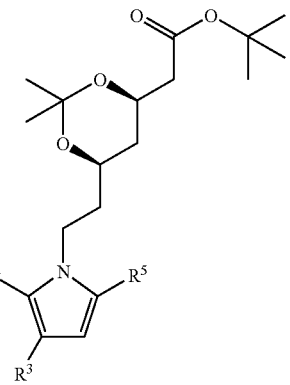

or a pharmaceutically acceptable salt, ester, amide, stereoisomer or prodrug thereof or a pharmaceutically acceptable salt of the prodrug wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; $R^3$ is H; aryl, aralkyl, heteroaryl, heteroaralkyl, optionally substituted; $C_1$-$C_8$ alkyl straight chain or branched; or $C_3$-$C_8$ cycloalkyl; and $R^5$ is alkyl of from one to four carbon atoms, optionally substituted with a halogen.

The present invention also provides a compound having a formula

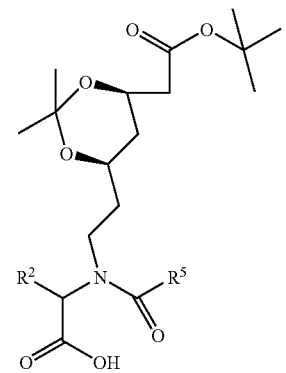

wherein $R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms; and $R^5$ is alkyl of from one to four carbon atoms, optionally substituted with a halogen. Also provided is the above compound wherein $R^5$ is isopropyl. Also provided is the above compound wherein $R^5$ is isopropyl and $R^5$ is para-fluorophenyl.

Also provided is a racemic mixture comprising a compound of Formula 1.

The following definitions are used, unless otherwise described. Halo is fluoro, chloro, bromo or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically recited.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, $—O(CH_2)_{0-2}CF_3$, halogen, nitro, cyano, $=O$, $=S$, $—OH$, $—SH$, $—CF_3$, $—CO_2H$, $—CO_2C_1-C_6$ alkyl, $—NH_2$, $—NHC_1-C_6$ alkyl, $—CONR'R"$, or $—N(C_1-C_6 alkyl)_2$ where R' and R" are independently alkyl, akenyl, alkynyl, aryl, or joined together to form a 4 to 7 member ring. Useful alkyl groups have from 1 to 6 carbon atoms ($C_1-C_6$ alkyl).

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Optionally, lower alkyl is referred to as "$C_1-C_6$ alkyl."

The term "haloalkyl" as used herein refers to a lower alkyl radical, as defined above, bearing at least one halogen substituent, for example, chloromethyl, fluoroethyl, trifluoromethyl, or 1,1,1-trifluoroethyl and the like. Haloalkyl can also include perfluoroalkyl wherein all hydrogens of a loweralkyl group are replaced with fluorine atoms.

The term "alkenyl" means a straight or branched unsaturated hydrocarbon radical having from 2 to 12 carbon atoms and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched hydrocarbon radical having of 2 to 12 carbon atoms having at least one triple bond and includes, for example, 3-propynyl, 1-butynyl, 3-butynyl, 1-pentynyl, 3-pentynyl, 3-methyl-3-butynyl, 1-hexynyl, 3-hexynyl, 3-hexynyl, 3-heptynyl, 1-octynyl, 1-nonynyl, 1-decynyl, 1-undecynyl, 1-dodecynyl, and the like.

The term "alkylene" as used herein refers to a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like. The alkylene groups of this invention can be optionally substituted with one or more of the substituents selected from lower alkyl, lower alkoxy, lower thioalkoxy, $—O(CH_2)_{0-2}CF_3$, halogen, nitro, cyano, $=O$, $=S$, $—OH$, $—SH$, $—CF_3$, $—CO_2H$, $—CO_2C_1-C_6$ alkyl, $—NH_2$, $—NHC_1-C_6$ alkyl, $—CONR'R"$, or $—N(C_1-C_6 alkyl)_2$ where R' and R" are independently alkyl, akenyl, alkynyl, aryl, or joined together to form a 4 to 7 member ring. Useful alkylene groups have from 1 to 6 carbon atoms ($C_1-C_6$ alkylene).

The term "heteroatom" as used herein represents oxygen, nitrogen, or sulfur (O, N, or S) as well as sulfoxyl or sulfonyl ($SO$ or $SO_2$) unless otherwise indicated.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, $—O(CH_2)_{0-2}CF_3$, halogen, nitro, cyano, $=O$, $=S$, $—OH$, $—SH$, $—CF_3$, $—CO_2H$, $—CO_2C_1-C_6$ alkyl, $—NH_2$, $—NHC_1-C_6$ alkyl, $—CONR'R"$, or $—N(C_1-C_6 alkyl)_2$ where R' and R" are independently alkyl, akenyl, alkynyl, aryl, or joined together to form a 4 to 7 member ring.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower alkoxy, lower thioalkoxy, $—O(CH_2)_{0-2}CF_3$, halogen, nitro, cyano, $=O$, $=S$, $—OH$, $—SH$, $—CF_3$, $—CO_2H$, $—CO_2C_1-C_6$ alkyl, $—NH_2$, $—NH(C_1-C_6$ alkyl), $—CONR'R"$, or $—N(C_1-C_6 alkyl)_2$ where R' and R" are independently alkyl, akenyl, alkynyl, aryl, or joined together to form a 4 to 7 member ring.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The terms "lower alkoxy" and "lower thioalkoxy" as used herein refers to O-alkyl or S-alkyl of from 1 to 6 carbon atoms as defined above for "lower alkyl."

The term "aryl" as used herein refers to an aromatic ring which is unsubstituted or optionally substituted by 1 to 4 substituents selected from lower alkyl, lower alkoxy, lower thioalkoxy, $—O(CH_2)_pCF_3$, halogen, nitro, cyano $—OH$, $—SH$, $—CF_3$, $—CO_2H$, $—CO_2C_1-C_6$ alkyl, $—NH_2$, $—NHC_1-C_6$ alkyl, $—SO_2alkyl$, $—SO_2NH_2$, $—CONR'R"$, or $—N(C_1-C_6 alkyl)_2$ where R' and R" are independently alkyl, akenyl, alkynyl, aryl, or joined together to form a 4 to 7 member ring. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, or the like. Further, the term "aryl" means a cyclic or polycyclic aromatic ring having from 5 to 12 carbon atoms, and being unsubstituted or substituted with up to 4 of the substituent groups recited above for alkyl, alkenyl, and alkynyl.

The term aralkyl as used herein means aryl, as defined above, attached to an alkyl group.

The term "heteroaryl" means an aromatic ring containing one or more heteroatom. The heteroaryl is optionally substituted with one or more groups enumerated for aryl. Examples of heteroaryl include, but are not limited to thienyl, furanyl, pyrrolyl, pyridyl, pyrimidyl, imidazoyl, pyrazinyl, oxazolyl, thiazolyl, benzothienyl, benzofuranyl, indolyl, quinolinyl, isoquinolinyl, and quinazolinyl, and the like. Further, the term "heteroaryl" means an aromatic mono-, bi-, or polycyclic ring incorporating one or more (i.e. 1-4) heteroatoms selected from N, O, and S, which mono-, bi-, or polycyclic ring is optionally substituted with $—OH$, $—O(alkyl)$, $SH$, $S(alkyl)$, amine, halogen, acid, ester, amide, amidine, alkyl ketone, aldehyde, nitrile, fluoroalkyl, nitro, sulphone, sulfoxide or $C_{1-6}$ alkyl. Examples further include 1-, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 1,3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic heteroaryl compounds include, but are not limited to indolizinyl, isoindolyl, benzofuranyl, benzothienyl, benzoxazolyl, benzimidazolyl, quinolinyl, isoquinolinyl, quinazolinyl, 1-, 2-, 3-, 4-, 5-, 6-, or 7-indolyl, 1-, 2-, 3-, 5-, 6-, 7-, or 8-indolizinyl, 1-, 2-, 3-, 4-, 5-, 6-, or 7-isoindolyl, 2-, 3-, 4-, 5-, 6-, or 7-benzothienyl, 2-, 4-, 5-, 6-, or 7-benzoxazolyl, 1-, 2-, 4-, 5-, 6-, or 7-benzimidazolyl, 2-, 3-, 4-, 5-, 6-, 7-, or 8-quinolinyl, and 1-, 3-, 4-, 5-, 6-, 7-, or 8-isoquinolinyl.

The term heteroaralkyl, as used herein, means heteroaryl, as defined above, attached to an alkyl group.

The term "heterocycle" means a saturated mono- or polycyclic (i.e. bicyclic) ring incorporating one or more (i.e. 1-4) heteroatoms selected from N, O, and S. It is understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or C1-6 alkyl. Examples of suitable monocyclic heterocycles include, but are not limited to piperidinyl, pyrrolidinyl, piperazinyl, azetidinyl, aziridinyl, morpholinyl, thietanyl, oxetaryl.

The term "cycloalkyl" means a saturated hydrocarbon ring. Further, the term "cycloalkyl" means a hydrocarbon ring containing from 3 to 12 carbon atoms, for example, cyclopropyl, cyclobutyl, cyclopentyl, cyclohexyl, cycloheptyl, cyclooctyl, decalinyl, norpinanyl, and adamantyl. The cycloalkyl ring may be unsubstituted or substituted by 1 to 3 substituents selected from alkyl, alkoxy, thioalkoxy, hydroxy, thiol, nitro, halogen, amino, alkyl and dialkylamino, formyl, carboxyl, CN, —NH—CO—R—CO—NHR—, —CO$_2$R—, —COR—, aryl, or heteroaryl, wherein alkyl, aryl, and heteroaryl are as defined herein. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "cycloalkenyl" means a cycloalkyl group having one or more carbon-carbon double bond. Example includes cyclobutene, cyclopentene, cyclohexene, cycloheptene, cyclobutadiene, cyclopentadiene, and the like.

The term "isomer" means "stereoisomer" and "geometric isomer" as defined below.

The term "stereoisomer" means compounds that possess one or more chiral centers and each center may exist in the R or S configuration. Stereoisomers includes all diastereomeric, enantiomeric and epimeric forms as well as racemates and mixtures thereof.

The term "geometric isomer" means compounds that may exist in cis, trans syn, anti, entgegen (E), and zusammen (Z) forms as well as mixtures thereof.

The symbol "=" means a double bond.

The symbol "⌒" means a bond to a group wherein a 4 to 8 membered ring is formed. Typically this symbol will appear in pairs.

When a bond to a substituent is shown to cross the bond connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring.

When a bond from a substituent is shown to cross the bond connecting 2 atoms in a ring of the substituent, then such substituent may be bonded from any atom in the ring which is available.

When a bond is represented by a line such as "—" this is meant to represent that the bond may be absent or present provided that the resultant compound is stable and of satisfactory valency. If an assymetic carbon is created by such a bond, a particular stereochemistry is not to be implied.

As used herein, the following terms have the meanings given: RT means room temperature. MP means melting point. MS means mass spectroscopy. TLC means thin layer chromatography. [S]at. means saturated. [C]onc. means concentrated. TBIA means tert-Butylisopropylidene amine. DCM means dichloromethane, which is used interchangeably with methylene chloride. NBS means N-Bromosuccinimide. "h" means hour. "v/v" means volume ratio or "volume per volume". $R_f$ means retention factor. Tf$_2$O means "triflicanhydride". Ac$_2$O means aceticanhydride. "[T]rifluorotol." means trifluorotoluene. "DMF" means dimethylformamide. "DCE" means dichloroethane.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of hyperlipidemia, hypercholesterolemia, hypertriglyceridemia or atherosclerois.

The term "a pharmaceutically acceptable salt, ester, amide, or prodrug" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "a pharmaceutically acceptable salt" refers to the relatively non-toxic, inorganic and organic acid or base addition salts of compounds of the present invention. These salts can be prepared in situ during the final isolation and purification of the compounds or by separately reacting the purified compound in its free form with a suitable organic or inorganic acid or base and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977; 66:1-19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines, the amine may also be in the form of a 5- or 6-membered heterocycle containing one nitrogen atom.

Amides derived from ammonia, $C_1$-$C_3$ alkyl primary amines and $C_1$-$C_2$ dialkyl secondary amines are preferred. Amides of the compounds of the invention may be prepared according to conventional methods.

"Prodrugs" are intended to include any covalently bonded carrier which releases the active parent drug according to Formula I in vivo. Further, the term "prodrug" refers to compounds that are transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include acetates, formates, benzoate derivatives of alcohols, and amines present in compounds of Formula I.

In some situations, compounds may exist as tautomers. All tautomers are included within Formula I and are provided by this invention.

Certain compounds of the present invention can exist in unsolvated form as well as solvated form including hydrated form. In general, the solvated form including hydrated form is equivalent to unsolvated form and is intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns and by chiral synthesis. Additionally, the compounds of the present invention may exist as geometric isomers. The present invention includes all cis, trans, syn, anti, entgegen (E), and zusammen (Z) isomers as well as the appropriate mixtures thereof.

The compounds of the present invention are suitable to be administered to a patient for the treatment, control, or prevention of, hypercholesteremia, hyperlipidemia, atherosclerosis and hypertriglyceridemia. The terms "treatment", "treating", "controlling", "preventing" and the like, refers to reversing, alleviating, or inhibiting the progress of the disease or condition to which such term applies, or one or more symptoms of such disease or condition. As used herein, these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound of the invention to a subject that is not at the time of administration afflicted with the disease or condition. "Preventing" also encompasses preventing the recurrence of a disease or condition or of symptoms associated therewith. Accordingly, the compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

Preparation of Compounds of the Invention

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods, which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC or recrystallization may be employed. The following non-limiting descriptions also demonstrate methods for the synthesis of compounds of the invention.

Scheme 1 shows the preparation of compounds of Formula I wherein $R^2$ and $R^3$ are each parafluorophenyl, $R^4$ is $SO_2NR^9R^{10}$ and $R^5$ is isopropyl.

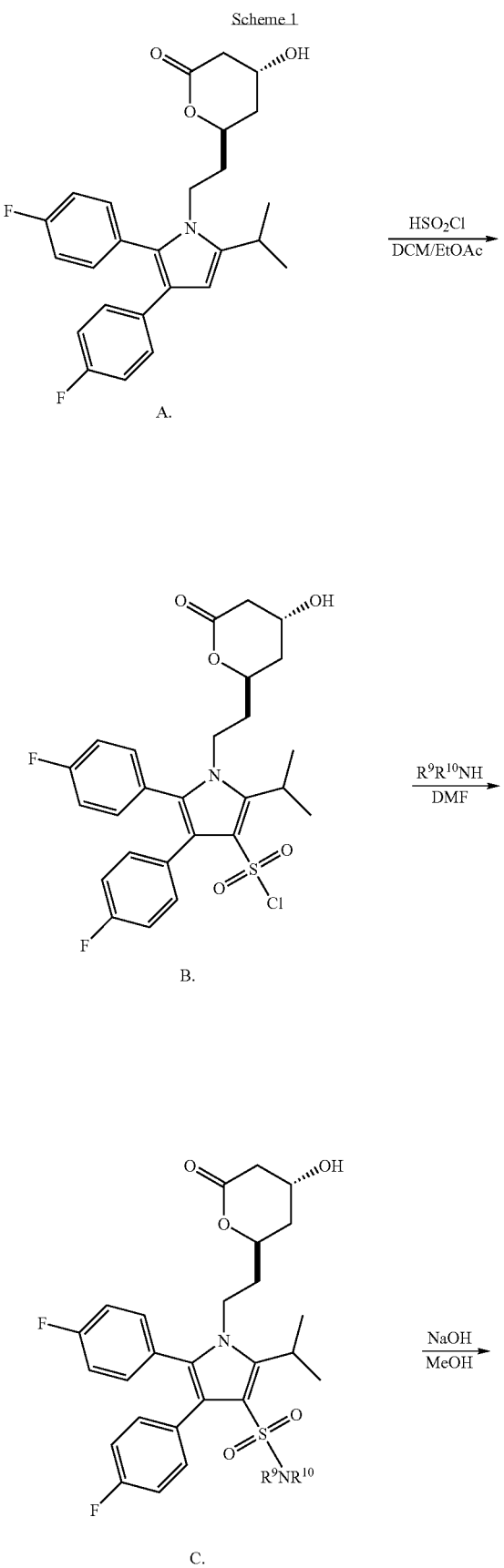

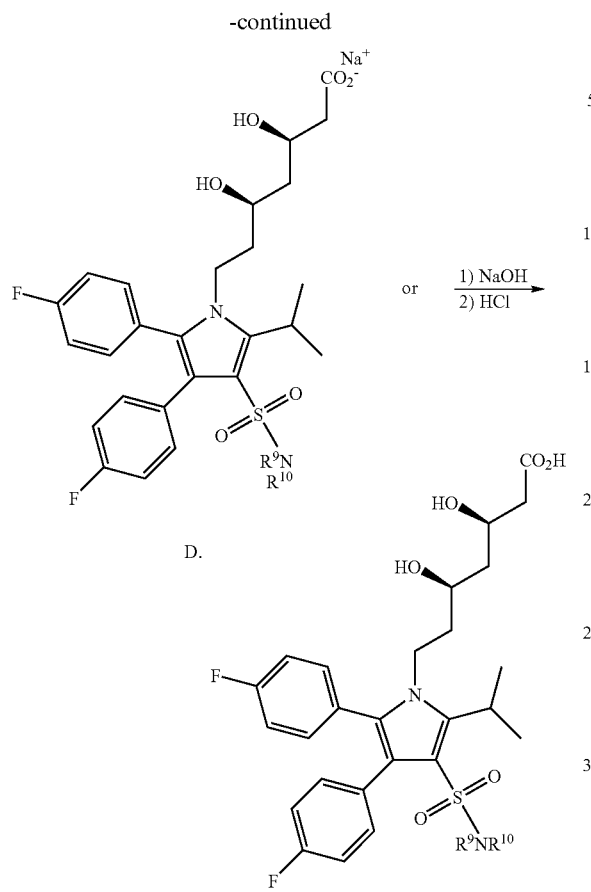

Compound A is treated with chlorosulfonic acid in dichloromethane to give compound B which reacts with an amine of interest in DMF to afford the sulfonamide C. Hydrolysis of the lactone gives the desired compound D, a sodium salt or di-sodium salt depending on the chemical nature of $R^9$ and $R^{10}$ groups. Alternatively, one could work up the reaction under acidic conditions to isolate the corresponding free acid. Preparation of starting material A is shown in Scheme 1a:

The di-ketone 1, which was prepared in a similar manner as described by Bruce et al (J. Med. Chem. 1991, 34, 357-366), reacts with amine 2 (see US005149837A for the synthesis) under acidic conditions to give compound 3. Acid catalyzed hydrolysis of the acetonide 3 followed by saponification of the ester using aqueous NaOH solution affords the di-hydroxy acid. Acid catalyzed lactonization of the di-hydroxy acid gives the compound A.

Alternate methods for preparing compounds of the invention are shown in Scheme 2 and in Scheme 2i.

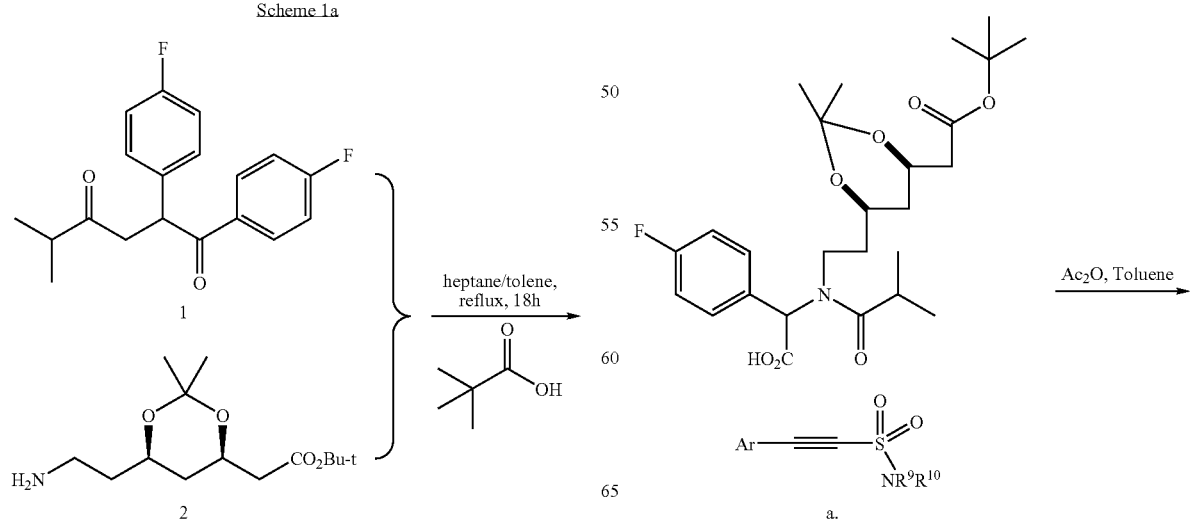

29
-continued
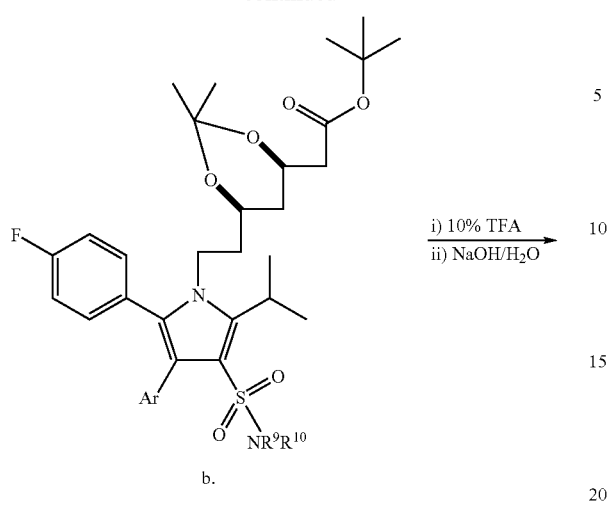
b.
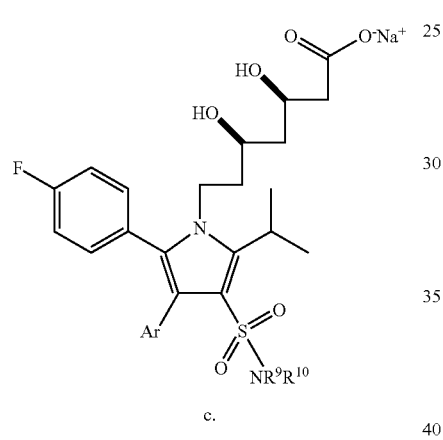
c.
30
-continued
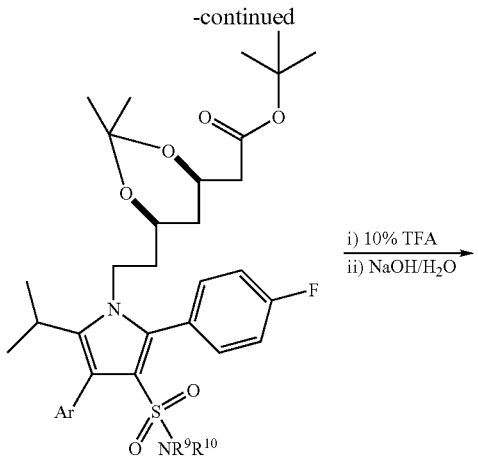
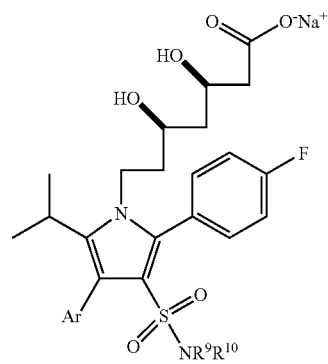
Similar compounds may be made using Scheme 2 and 2i, for example, as shown in Scheme 2a and Scheme 2ai:
Scheme 2i
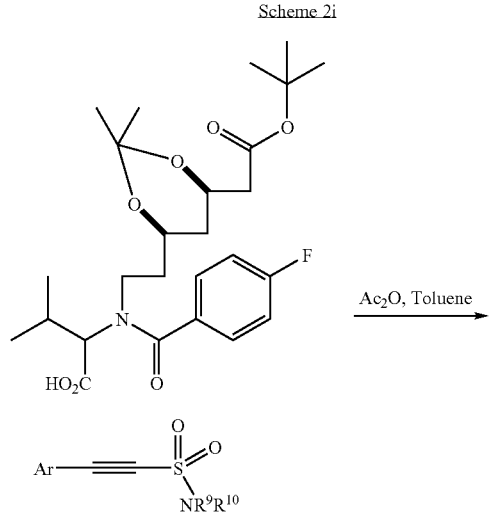
Scheme 2a
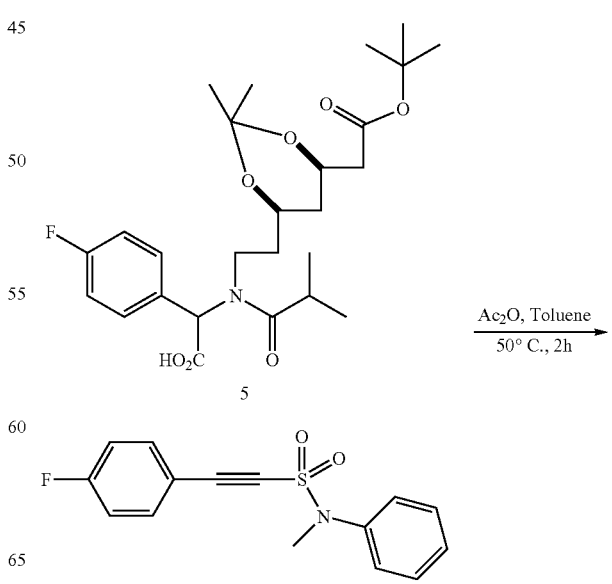

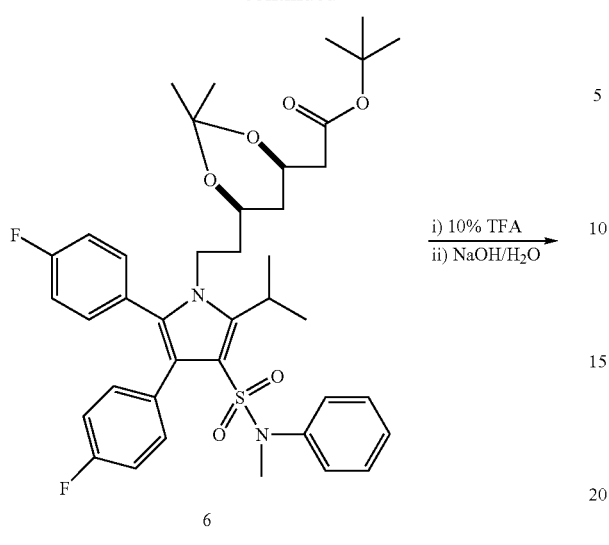
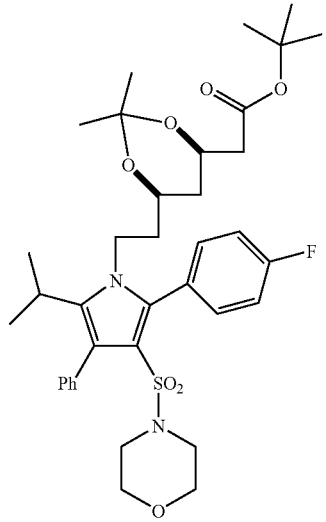
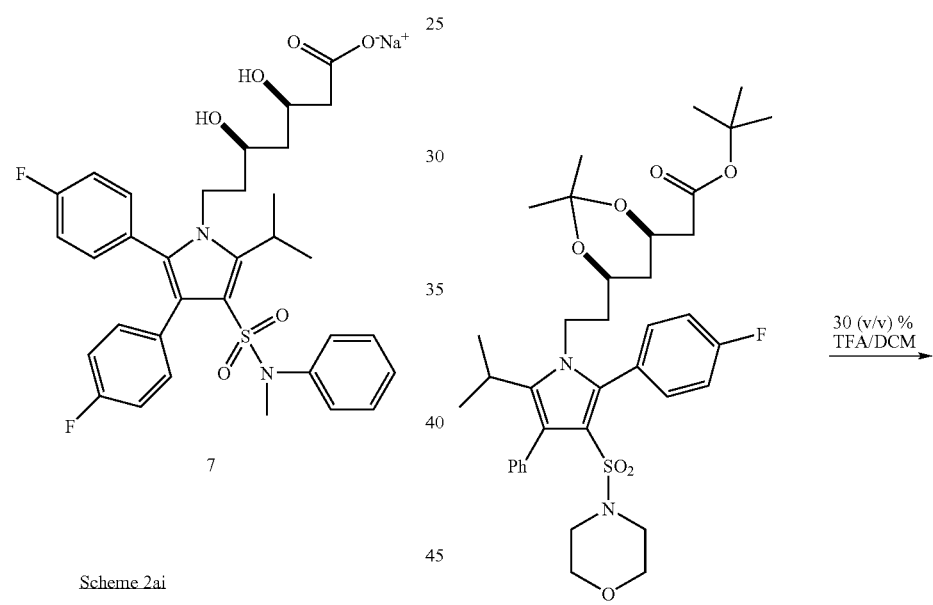
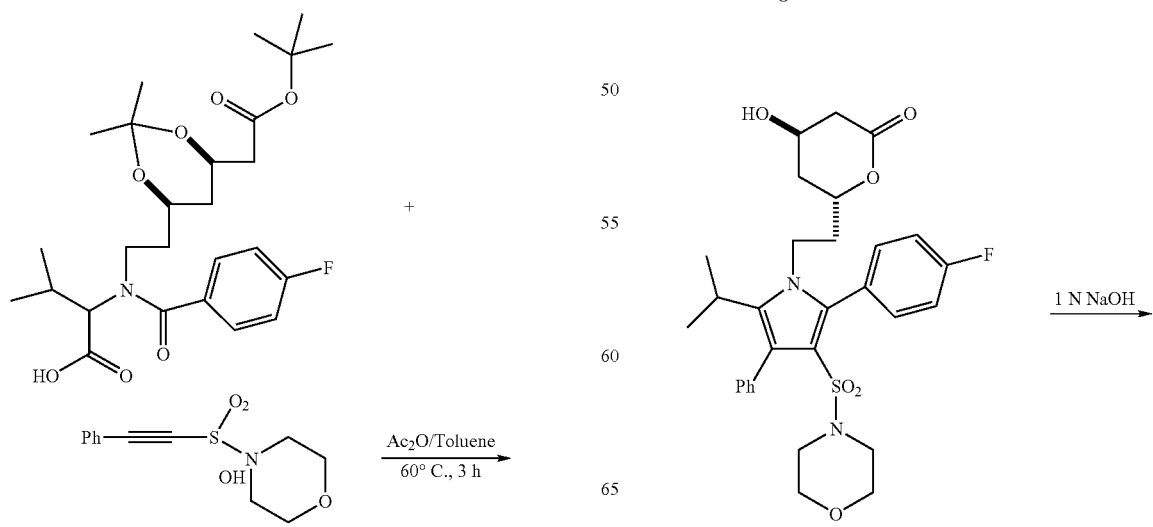
Scheme 2ai

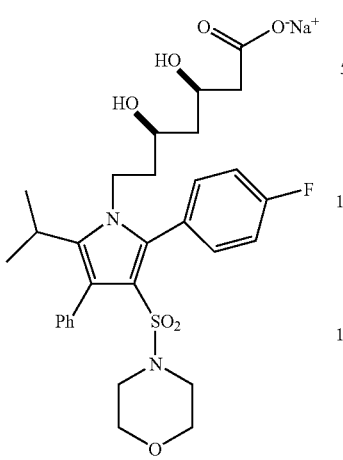

In Scheme 2a, a Munchnone intermediate is formed in situ from acetic anhydride and compound 5, and subsequent [3+2] cycloaddition of this intermediate with the alkynyl-sulfonamide 4 gives the desired regioisomer 6 in high yield. Treatment of 6 with TFA yields a lactone which in turn is hydrolyzed by NaOH to provide the final compound 7.

The starting materials for reaction Scheme 2a and 2ai may be made as shown in the following Schemes 2b, 2c and 2ci.

Scheme 2b

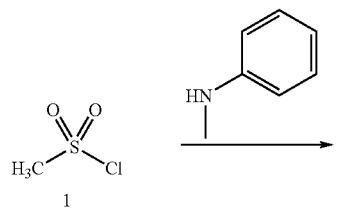

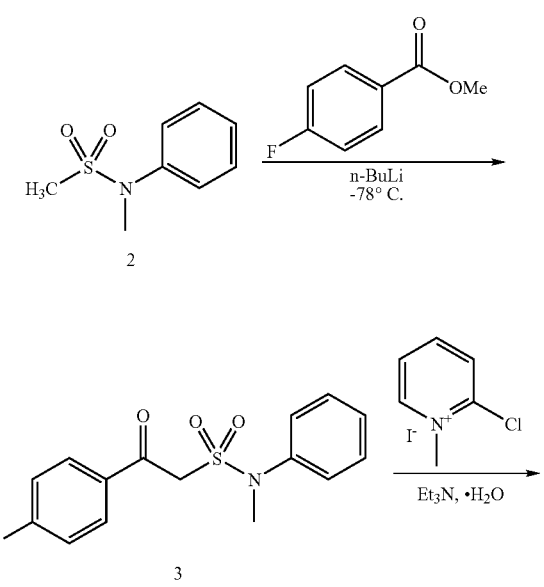

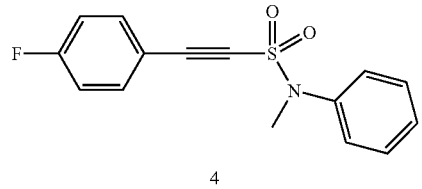

The main advantages of synthetic Schemes 2, 2a, 2b and 2c are two-fold: first, an effective route to compound 4. Second, achieving the right regioisomer in high yield (for example, compound 6). In Scheme 2b, the reaction of methane sulfonyl chloride (1) with N-methylaniline provides the corresponding sulfonamide (2) with high yield. The subsequent alkylation of 2 with 4-fluorobenzoic acid methyl ester yields the desired β-ketosulfonamide 3. Mukiyama reaction conditions (for example, 2-chloro N-methylpyridinium iodide, triethylamine) were employed for dehydration of 3 to give the corresponding alkynyl sulfonamide 4. As used herein, "Mukiyama reaction conditions" means reaction conditions that effect dehydration of β-ketosulfonamide.

Scheme 2c describes the formation of the Munchnone precursor 5. Starting with 4-fluorobenzoic acid esterification to make methyl ester, subsequent bromination with NBS (N-bromosuccinimide) with a catalytic amount of HBr results in a bromo methyl ester 5b. A simple nucleophilic substitution reaction with the amine (TBIA) in the presence of base (triethylamine) provides the 5c with high yield. This secondary amine is acylated with for example, isobutyryl chloride (I—PrC(O)Cl) to give the desired methyl ester product. The methyl ester is hydrolyzed with a base LiOH to give the Munchnone precursor 5.

Scheme 2c

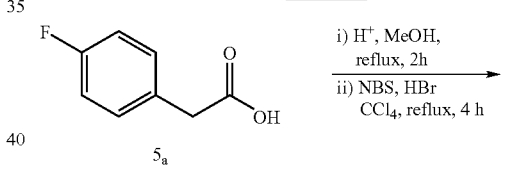

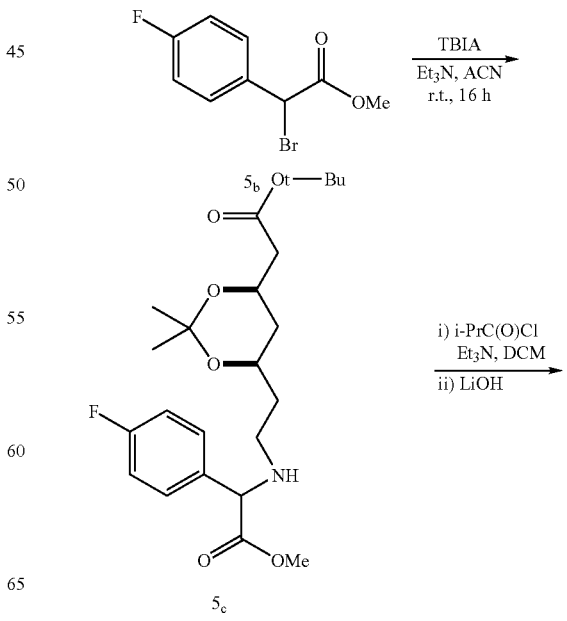

-continued

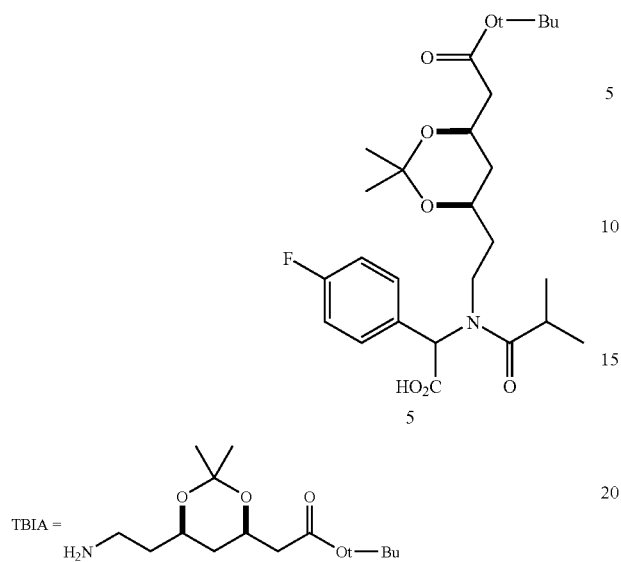

Scheme 2ci

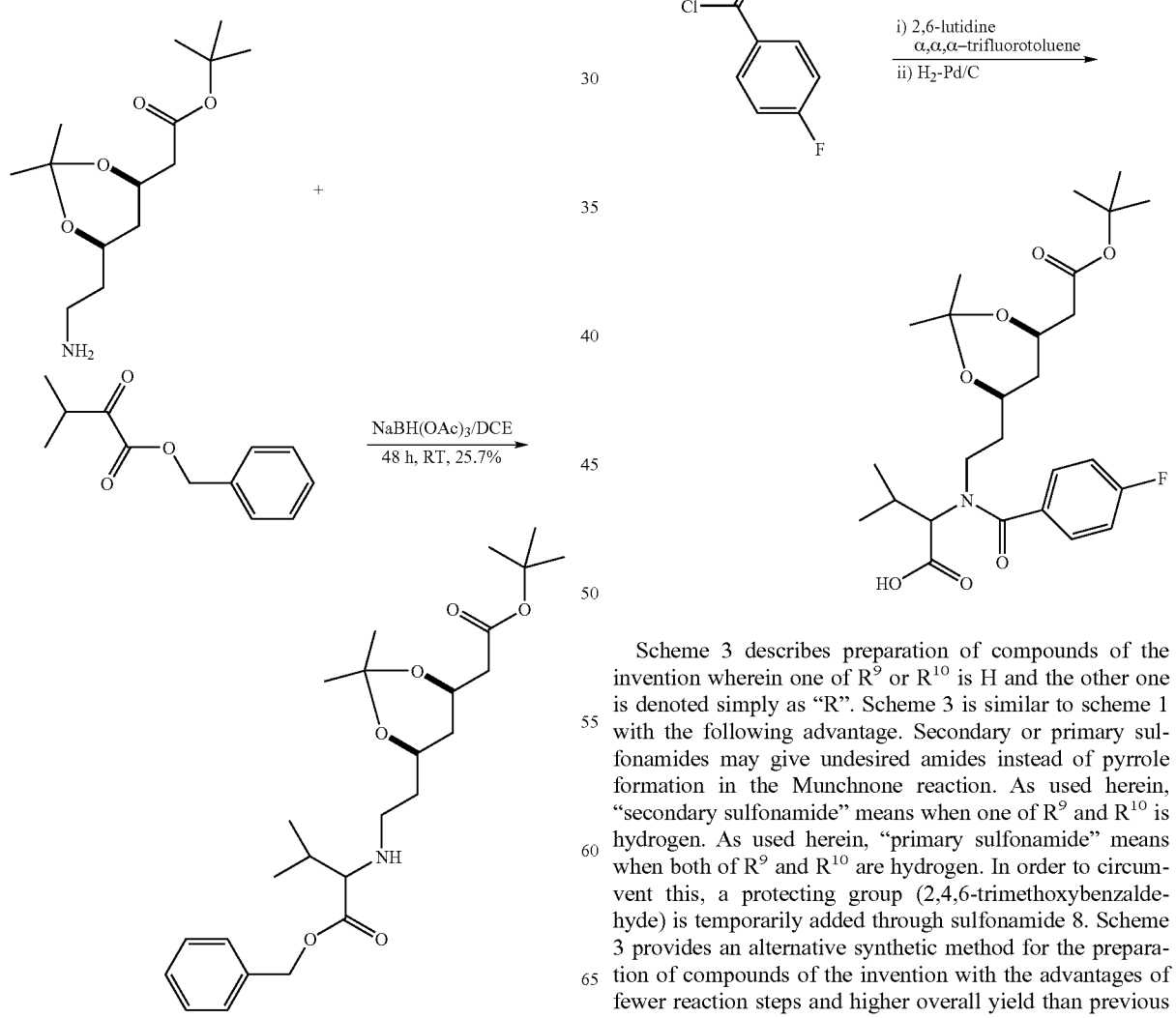

-continued

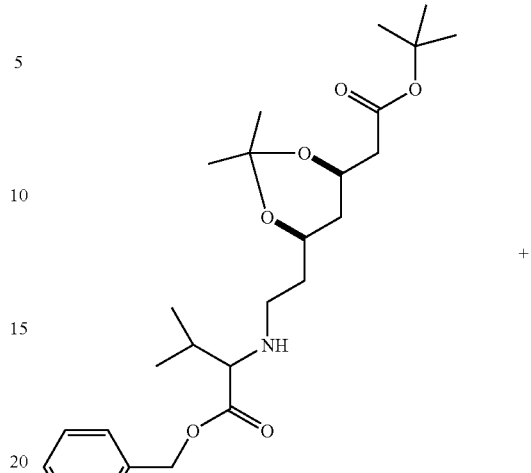

Scheme 3 describes preparation of compounds of the invention wherein one of $R^9$ or $R^{10}$ is H and the other one is denoted simply as "R". Scheme 3 is similar to scheme 1 with the following advantage. Secondary or primary sulfonamides may give undesired amides instead of pyrrole formation in the Munchnone reaction. As used herein, "secondary sulfonamide" means when one of $R^9$ and $R^{10}$ is hydrogen. As used herein, "primary sulfonamide" means when both of $R^9$ and $R^{10}$ are hydrogen. In order to circumvent this, a protecting group (2,4,6-trimethoxybenzaldehyde) is temporarily added through sulfonamide 8. Scheme 3 provides an alternative synthetic method for the preparation of compounds of the invention with the advantages of fewer reaction steps and higher overall yield than previous methods.

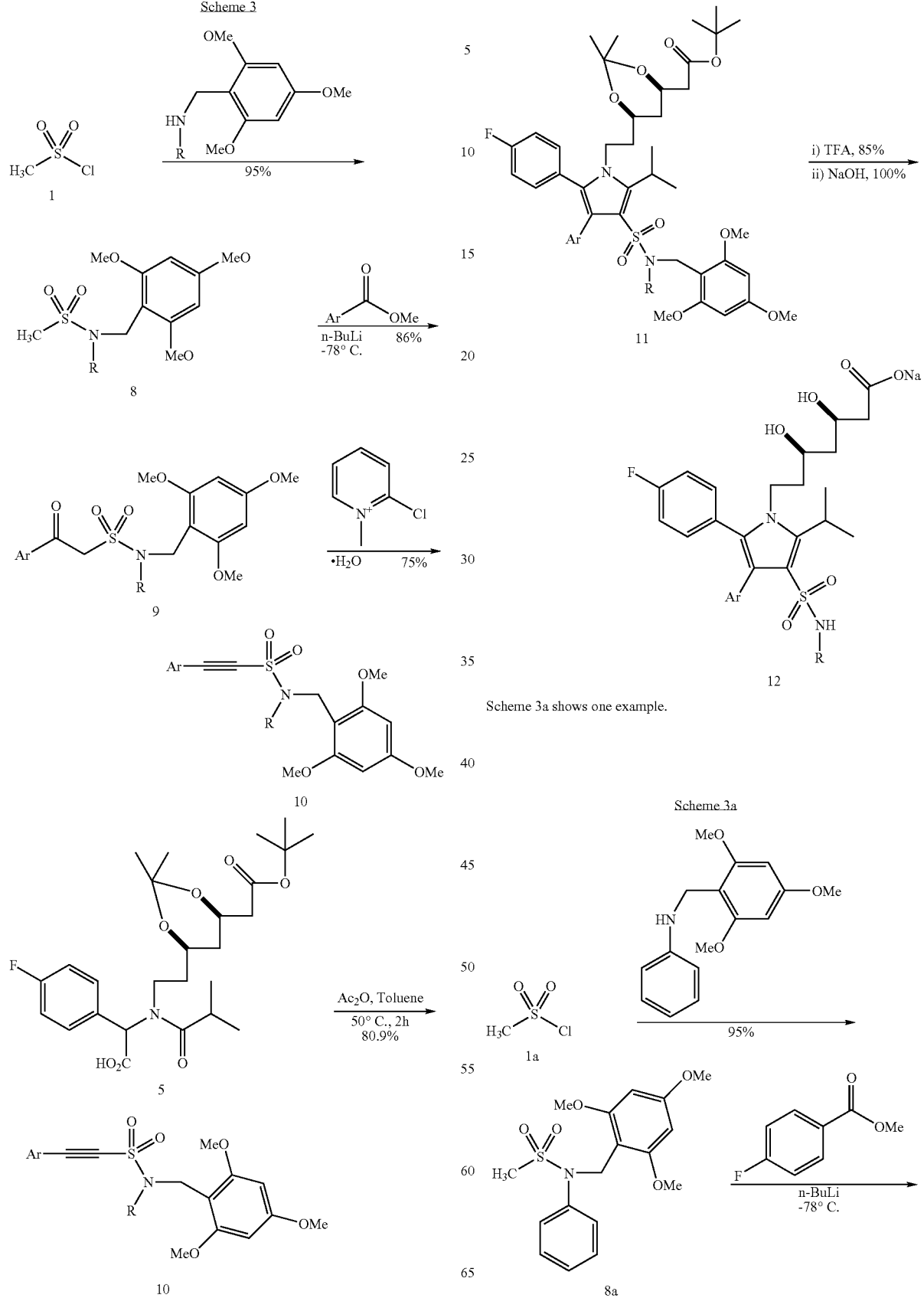
Scheme 3a shows one example.

-continued

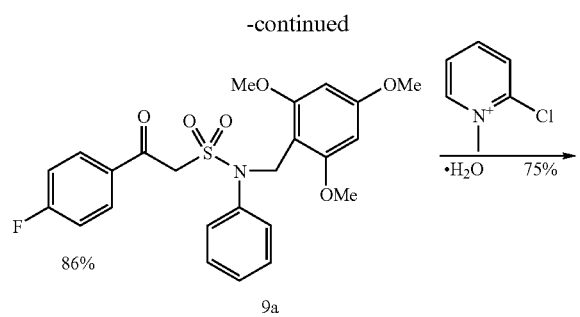

9a 86%

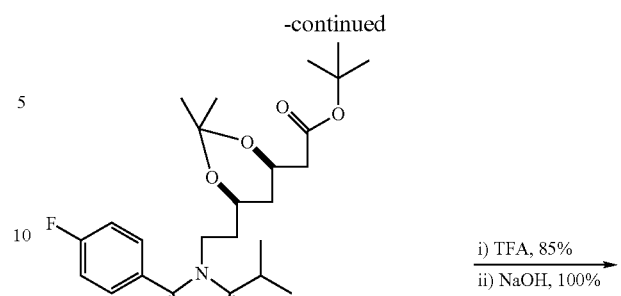

11a i) TFA, 85%
ii) NaOH, 100%

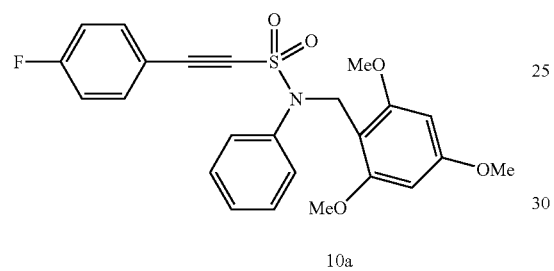

10a

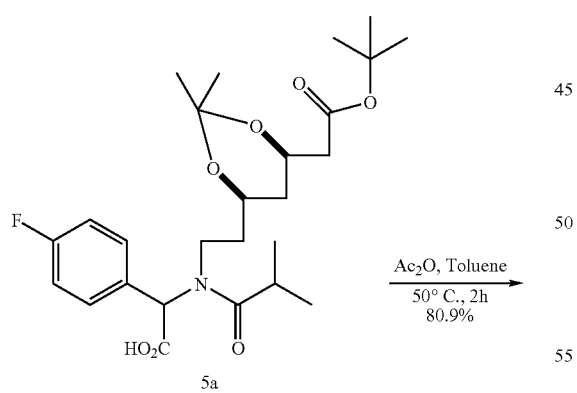

5a

Ac₂O, Toluene
50° C., 2h
80.9%

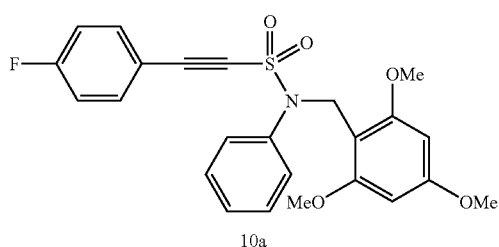

10a

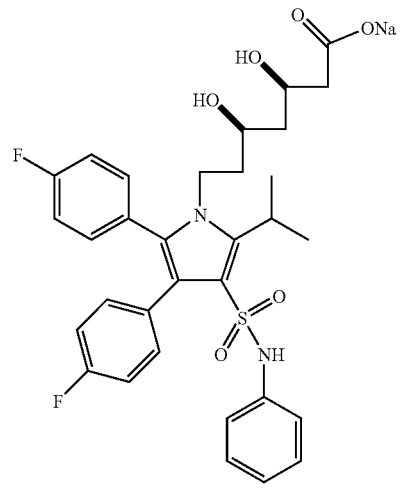

12a

Both synthetic routes shown in Schemes 1 and 3 include aryl-substituted alkyne sulfonamides (compound 4 and 10). The conversion of β-ketosulfonamides with a non-aryl, for example an alkyl group, may be difficult with Mukiyama conditions (2-chloro N-methylpyridinium iodide and triethylamine). For example, in Scheme 4, the non-aryl group is isopropyl and $NR^9R^{10}$ taken together are morpholino-. The use of Tf₂O-Hunig's base (for example, diisopropylethylamine, DIEA) conditions for dehydration of β-ketosul fonamides overcomes this problem. As used herein, "Hunig's base" can include any strong organic base capable of deprotonation of β-ketosulfonamide, preferably, diisopropylethylamine.

Scheme 4 shows the dehydration of a non-aryl or an alkyl-substituted β-ketosulfonamides to the corresponding alkyne. Scheme 4a shows one example.

Scheme 4

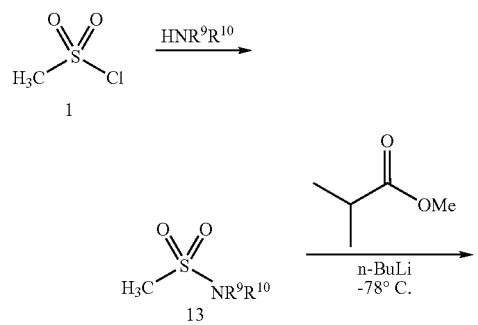

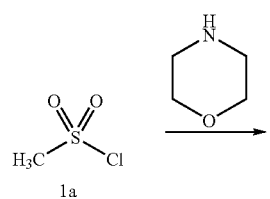

Scheme 4a

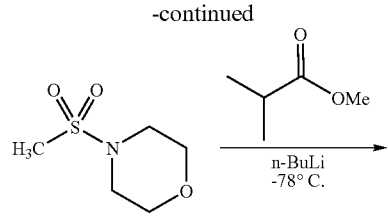

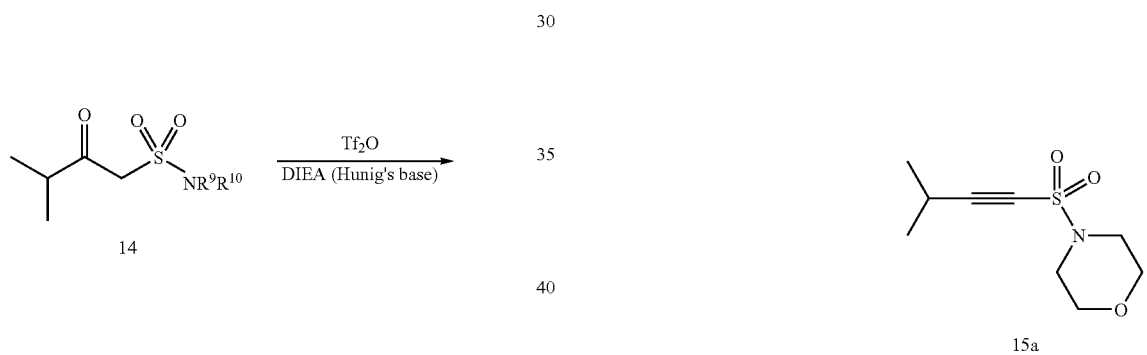

In Scheme 4, a variety of methyl esters including but not limited to those listed below may be used. An appropriate methyl ester is one that will result in the desired end product. Likewise, a variety of secondary amines including those listed below may be used.

Scheme 4, Examples of Methyl esters;

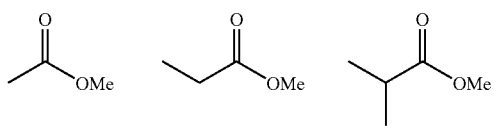

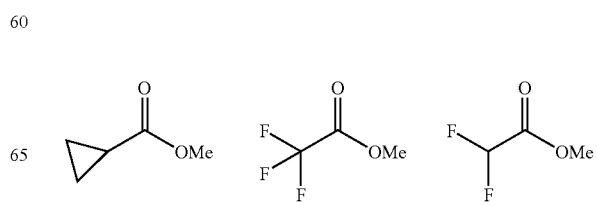

Scheme 4, Examples of secondary amines;

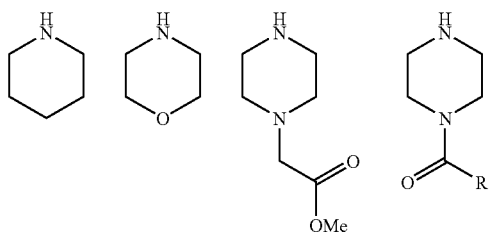

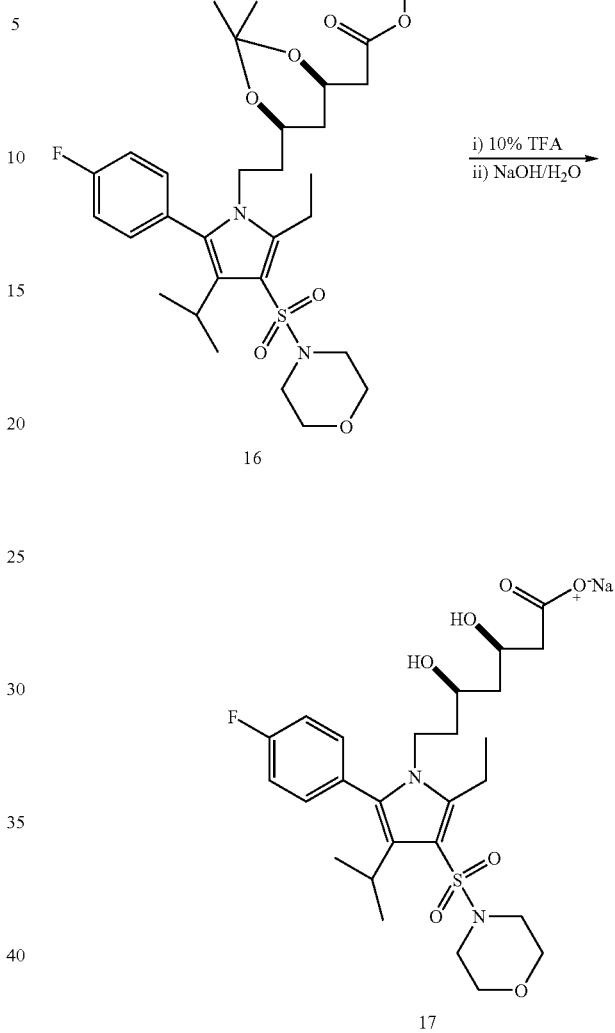

Scheme 5 shows the cycloaddition of a Munchnone precursor, 5'* and compound 15 via Munchnone reaction. The advantage of the reaction scheme shown in Scheme 5 is that the specific desired isomer e.g., 17, is obtained in high yield.

Scheme 5

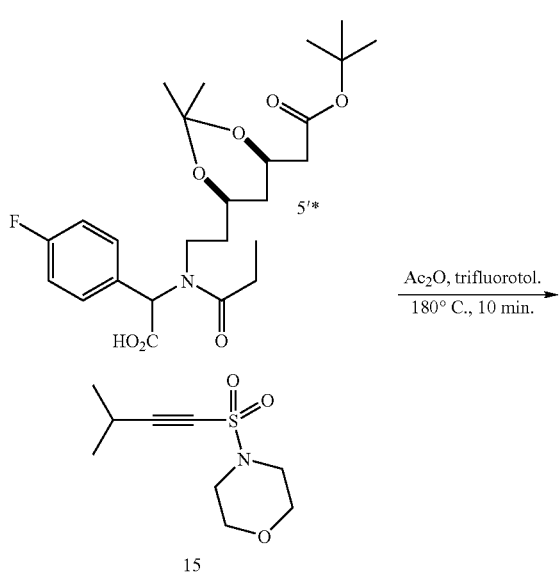

Scheme 6 shows, for example, the preparation of a compound of Formula I wherein $R^2$ and $R^3$ are each parafluorophenyl, $R^4$ is $R^6R^7NC(O)$— wherein one of $R^6$ and $R^7$ is H and the other one of $R^6$ and $R^7$ is $SO_2R^8$, and $R^5$ is isopropyl (compound 6). Scheme 6 also shows the preparation of a compound wherein $R^4$ is $R^6R^7N(C)O$— and one of $R^6$ and $R^7$ is H and the other one of $R^6$ and $R^7$ is $SO_2NHR^8$ (compound 4). Further, Scheme 6 shows the preparation of a compound wherein $R^4$ is $R^6R^7N(C)O$— and $R^6$ and $R^7$ are each H (compound 3).

In scheme 6, condensation reaction of compound 1 (see Scheme 1a for preparation of acetonide) with sulfonyl isocyanate 5 gives compound 6; condensation of compound 1 with chlorosufonyl isocyanate gives compound 2. Treatment of compound 2 with an aryl amine gives compound 4. When compound 2 is reacted with benzylamine, compound 3 may be isolated.

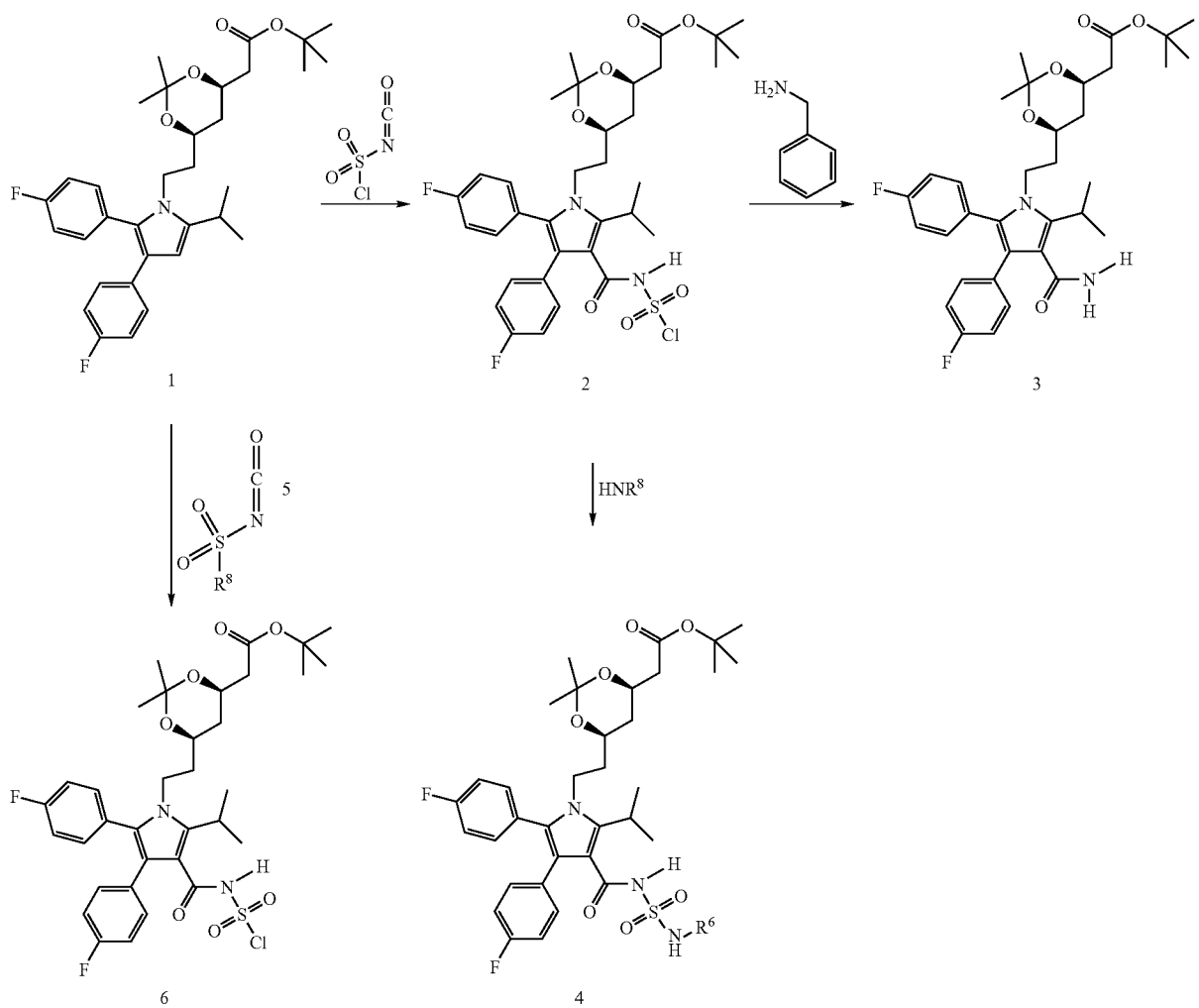
Scheme 6
In Scheme 7, the acetonide functional group is hydrolyzed using HC1 (1N) in methanol, and the hydrolysis of the ester affords the desired product a sodium salt or di-sodium salt depending on the chemical nature of the R⁴ group.
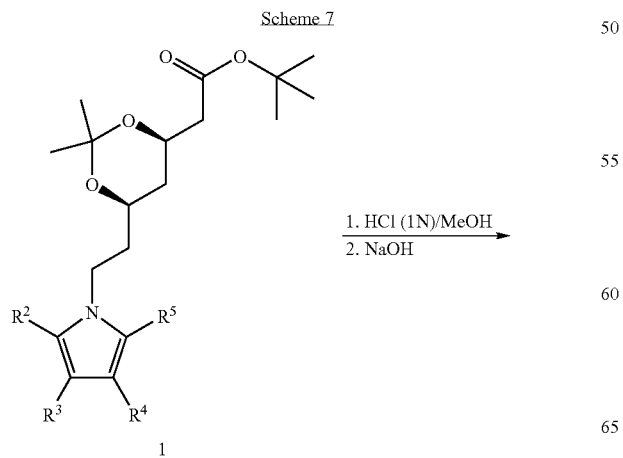
Scheme 7
EXAMPLES
The following non-limiting Examples show how to carry out the present invention. The synthetic route of compounds of the present invention is not limited to the methods outlined below. It is assumed that one skilled in the art will be able to use the schemes outlined below to synthesize compounds claimed in this invention.

Example 1 shows the preparation of a compound of Formula I wherein $R^2$ and $R^3$ are each para-fluorophenyl, $R^3$ is isopropyl and $R^4$ is $SO_2NR^9R^{10}$. In Example 1, one of $R^9$ and $R^{10}$ is H and the other one of $R^9$ and $R^{10}$ is phenyl. Compounds with variations on $R^9$ and $R^{10}$ were made using a similar reaction scheme and are shown, along with characterizing data, in TABLE I which follows Example 1.

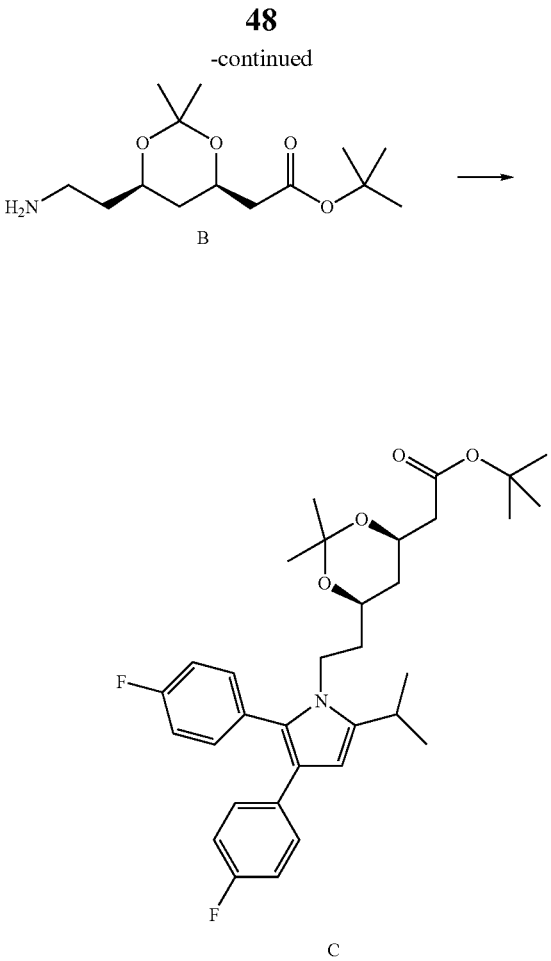

Example 1

(3R,5R)-7-[2,3-bis-(4-fluoro-phenyl)-5-isopropyl-4-phenylsulfamoyl-pyrrol-1-yl]-3,5-dihydroxy-heptanoic acid monosodium salt

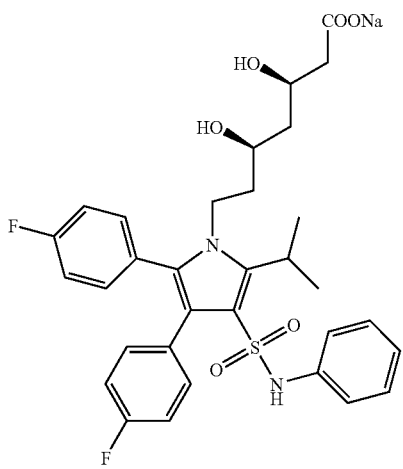

Step A

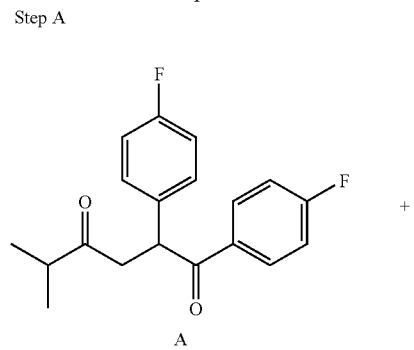

A

Preparation:

To a solution of the above starting material-A and the above starting material-B in heptane/toluene (9/1, v/v) was added trimethylacetic acid. The resulting reaction mixture was refluxed under $N_2$ for 16 hrs. The water formed was removed with a Dean-Stark trap. The total volume of the water removed was 1.85 mL (1.91 mL by theory). The reaction mixture was cooled to RT, washed successively with 1N HCl, 1N NaOH, sat. $NaHCO_3$ and brine, and concentrated in vacuo to give a brown syrup. The brown syrup was dissolved in 80 mL of MeOH, chilled in an ice-bath, yellow solid precipitated and the desired product was isolated via filtration (24.65 g), MP 88-91° C.

Combustion Analysis for ($C_{33}H_{41}F_2NO_4 \cdot 0.15CH_3OH$):

|  | Carbon | Hydrogen | Nitrogen | F |
|---|---|---|---|---|
| Theory | 71.29 | 7.51 | 2.51 | 6.80 |
| Found | 71.61 | 7.90 | 2.60 | 7.00 |

Step B

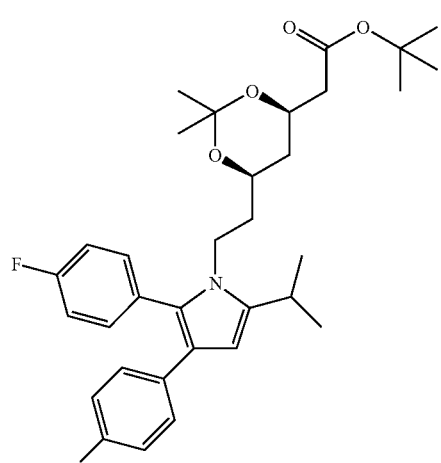

A

Step C

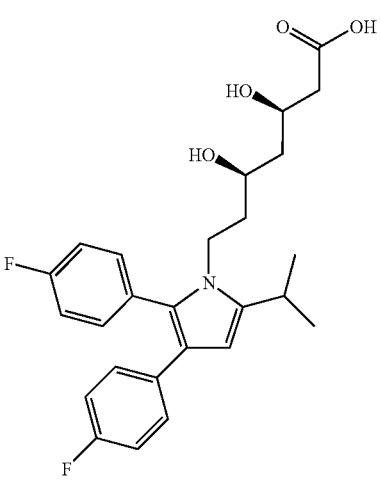

A

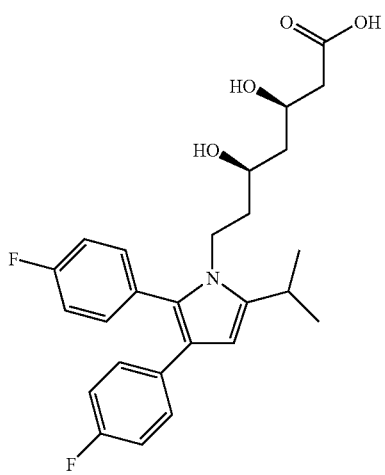

B

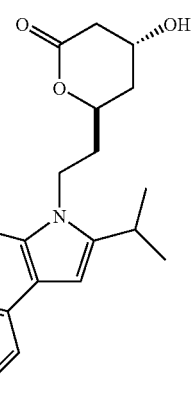

B

Preparation:

To a suspension of the above starting material-A from Step A in MeOH (8.88 mL/mmol, 308 mL) was added 1 N HCl (20.8 mL). The resulting mixture was stirred using a mechanical stirrer for 24 hours. An aqueous NaOH solution (1N, 55.5 mL) was added. The reaction mixture was stirred for another 16 hours. The reaction mixture was diluted with 100 mL of water, washed with hexane (2×200 mL), and acidified with con. HCl to pH=2. White precipitate formed, the mixture was extracted with EtOAc (3×200 mL), and the combined organic solution was dried over $Na_2SO_4$. The mixture was filtered and the filtrate was concentrated in vacuo, two phases formed, water was separated out, and the organic phase was concentrated affording a beige solid (14.5 g). MP 195-196° C.; MS, APCI+440.2 (M−18+H).

Combustion Analysis for [$C_{26}H_{29}F_2NO_4$]:

|  | Carbon | Hydrogen | Nitrogen | F |
|---|---|---|---|---|
| Theory | 68.26 | 6.39 | 3.06 | 8.30 |
| Found | 69.46 | 6.17 | 3.05 | 8.64 |

Preparation:

To a suspension of the above starting material-A from Step B in toluene (200 mL) was added conc. HCl (3 drops). The resulting mixture was refluxed for 5 hrs. Water formed was continuously removed from the system with a Dean-Stark trap. The residual solid was removed via a hot filtration, the filtrate was cooled to RT, white crystals formed and were isolated via filtration (12.2970 g). MS, APCI+440.2 (M+H);

Combustion Analysis for: $C_{26}H_{27}F_2NO_3$

|  | Carbon | Hydrogen | Nitrogen | F |
|---|---|---|---|---|
| Theory | 71.05 | 6.19 | 3.19 | 8.65 |
| Found | 71.10 | 6.45 | 3.40 | 8.56 |

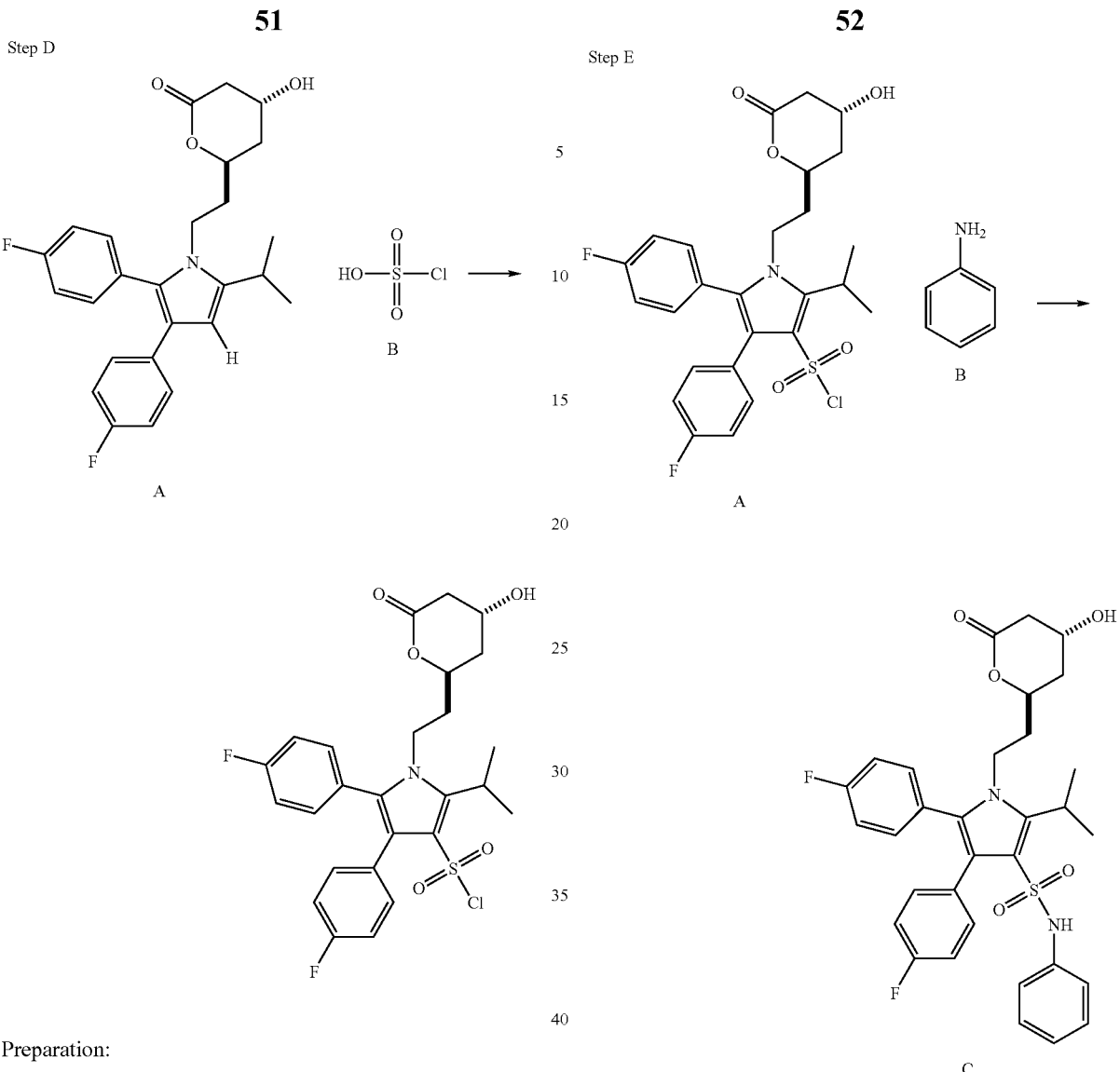

Step D

Step E

Preparation:

To a suspension of the starting material A from Step C in dichloromethane (9.0 mL) was added 12.0 mL of chlorosulfonic acid. A brown reaction solution was obtained. The reaction mixture was stirred at RT for 3 hours and 35 minutes. The reaction mixture was cooled to −60° C., diluted with 100 mL of ethyl acetate and cooled at −60° C. 200 mL of ethyl acetate at RT was added. The solution was warmed to 22° C., then poured onto ice. When the ice was, two phases were separated (aqueous layer was about 25 mL). The aqueous phase was extracted with EtOAc (1×20 mL), and the combined organic phase was poured onto ice again. The temperature of the mixture was kept at around 22° C. with a hot water bath. When the ice was melted, two phases were separated (aqueous layer was about 30 mL). The organic phase was washed again with brine (60 mL), the mixture was allowed to stand for 20 minutes for good phase separation, and then the two phases were separated. The organic phase was dried over $Na_2SO_4$ first, then solid $NaHCO_3$ was added to neutralize the residual acid in the solution. After 5 minutes, the mixture was filtered. The filtrate was concentrated in vacuo. When the volume was reduced to about 150 mL, the solution became cloudy. The mixture was filtered and the filtrate was concentrated to give the desired product (3.7247 g) as a light yellow foam which was used in the next step without further purifications.

Preparation:

To a solution of the starting material A from Step D, in DMF (2.0 mL), was added 0.666 mL of aniline. The reaction mixture was stirred at RT under nitrogen for 3 hours. After 3 hours, the reaction mixture was diluted with 50 mL of ethyl acetate, washed with 1 N HCl (2×30 mL) and brine, and dried over $Na_2SO_4$. The crude product was purified by chromatography and the desired product was isolated as a white foam (0.2685 g). MP, 93-101° C.

Combustion Analysis for $[C_{32}H_{32}F_2N_2O_5S \cdot 0.5C_4H_8O_2$ (ethyl acetate)]:

|  | Carbon | Hydrogen | Nitrogen | F |
|---|---|---|---|---|
| Theory | 63.93 | 5.68 | 4.39 | 5.95 |
| Found | 63.56 | 5.76 | 4.35 | 6.11 |

Step F

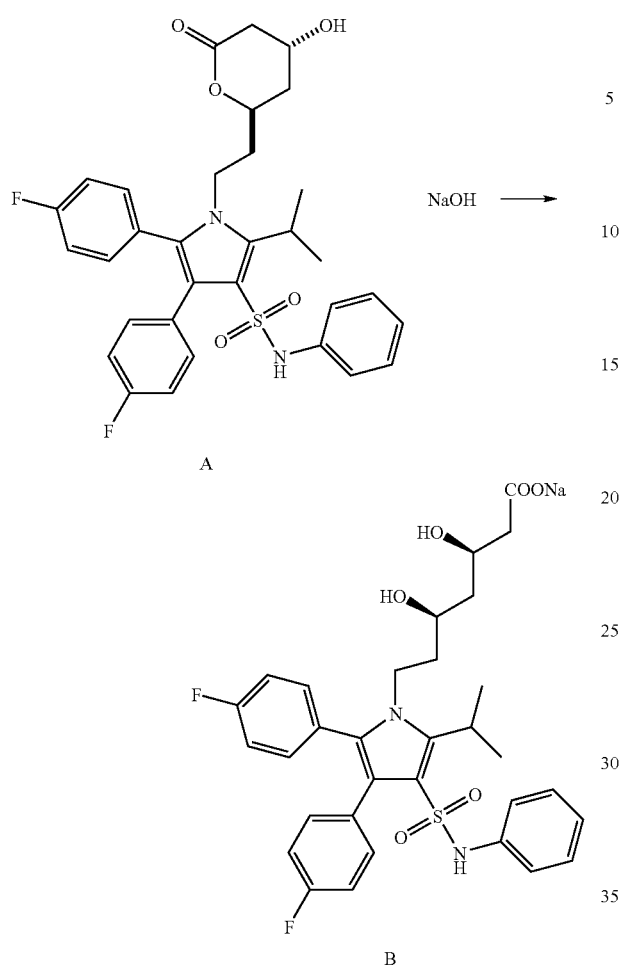

Preparation:

To a solution of the above starting material-A from Step E in MeOH was added 1N NaOH. The resulting reaction solution was stirred at RT for 40 minutes, and then concentrated in vacuo. 2 mL of MeOH was added to dissolve the residue, 10 mL of toluene was added, and then evaporated to azeotropically remove water. This process was repeated (twice) until a white solid was obtained. The white solid was dissolved in a very small amount of MeOH, then diluted with 20 mL of 5% MeOH in methylene chloride. A cloudy solution was obtained. After standing for 0.5 hour, the mixture was filtered to remove the solid (excess of NaOH, the sodium salt is soluble in 5% MeOH in methylene chloride). The filtrate was concentrated in vacuo to afford a solid, which was triturated with ether to form a white precipitate. Filtration gave the desired product as a beige solid (0.1885 g), MS (APCI+) 613.2; MP 130-134° C. (decomposed).

Combustion Analysis for $(C_{32}H_{33}F_2N_2NaO_6S \cdot C_4H_{10}O \cdot 1.5H_2O)$:

|  | Carbon | Hydrogen | Nitrogen | F |
|---|---|---|---|---|
| Theory | 58.23 | 5.66 | 4.14 | 5.62 |
| Found | 58.04 | 5.29 | 4.00 | 5.62 |

Compounds (sodium salt thereof) with variations on $R^9$ and $R^{10}$ were made using a similar reaction scheme to Example 1 and are shown, along with characterizing data, in TABLE I below.

TABLE I

Variations On Example 1

| $R^9$ | $R^{10}$ | MP | MS |
|---|---|---|---|
| H, | (4-isopropenylphenyl) | >240° C. | 671.1 (APCI+) |
| H, | (3-hydroxypropyl) | 147–150° C. | 581.1, acid + H (APCI+) |
| H, | (benzyl) | 115–119° C. |  |
| H, | (4-(CO$_2$Me)benzyl) | 131–135° C. | 685.2, acid + H (APCI+) |
| H, | (3-ONa-phenyl) | 166–169° C. | 629.1, acid + H (APCI+) |
| H, | (2-ONa-phenyl) | 175–178° C. | 629.2, acid + H (APCI+) |
| H, CH$_3$ |  | 140–143° C. |  |
| H, | (2,4-difluorophenyl) | 80–91° C. | 631.1 (M + H) (APCI+) |

TABLE I-continued

Variations On Example 1

| R⁹ R¹⁰ | | MP | MS |
|---|---|---|---|
| H, | 2-fluorophenyl | 84–90° C. | 613.1 (M + H) (ASPCI +) |
| H, | 4-fluorophenyl | 161–166° C. | 631.1 (APCI+) |
| H, | -CH₂CH₂C(O)NH₂ | 108–110° C. | 594.2 (acid + H) (APCI+) |
| NR⁹R¹⁰ = | 4-carbamoylpiperidin-1-yl | 161–165° C. | 648.2 (acid + H) (APCI+) |
| H, | -CH₂CH₂CH₂CO₂CH₃ | 120–124° C. | 623.2 (acid + H) (APCI+) |
| H, | -CH₂CH₂CH₂CH₂C(O)ONa | 155–157° C. | 623.1 (acid + H) (APCI+) |
| NR⁹R¹⁰ = | 4-(methoxycarbonyl)piperidin-1-yl | 150–155° C. | 663.2 (acid + H) (APCI+) |
| H, | -NHCH₂CH₂CH₂CO₂CH₃ | 105–108° C. | 637.2 (acid + H) (APCI+) |
| H, | -CH₂CH₂CH₂C(O)ONa | >240° C. | 609.1 (acid + H) (APCI+) |
| H, | 4-(carbamoylmethyl)phenyl | 125–127° C. | 670.3 (APCI+, acid + H) |
| H, | 3-carbamoylphenyl | 99–101° C. | 654.3 (APCI-, acid - H) |
| H, | 4-tert-butylcyclohexyl | 99–101° C. | 654.3 (APCI-, acid - H) |
| NR⁹R¹⁰ = | thiomorpholin-4-yl | 92–94° C. | 623.1 (APCI+, acid + H) |
| NR⁹R¹⁰ = | pyrrolidin-1-yl | 138–140° C. | 591.2 (APCI+, acid + H) |
| H, | 4-biphenyl | 150–152° C. | 689.2 (APCI+, acid + H) |

TABLE I-continued

Variations On Example 1

| R[9] R[10] | | MP | MS |
|---|---|---|---|
| NR[9]R[10] = | 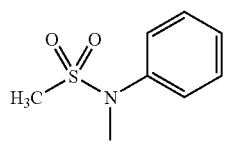 | 123–126° C. | 657 (APCI−, acid − H) |
| NR[9]R[10] = | | 151–153° C. | 673.1 (APCI+, acid + H) |

In Examples 2-17, the numbers refer to compounds shown in Schemes 2, 2a, 2b, 2c, 3, 3a, 4, 4a or 5.

Example 2

2

To a DCM solution (125 mL) containing methanesulfonyl chloride (10 g, 0.087 mole) at 0° C. was added N-methyl aniline (1.25 equiv), followed by dropwise addition of triethylamine (1.25 equiv). The reaction mixture was stirred at 0° C. for one hour and slowly warmed to room temperature. The TLC result showed a spot to spot transformation of the methanesulfonamide 2 (Rf=0.02 to 0.3 in 30% EtOAc/Hex). Work-up: The reaction mixture was evaporated under reduced pressure, and 1N aqueous HCl was added until the pH of the solution became acidic. The desired compound was extracted using EtOAc (25 mL×2), and the organic phase was washed with water (20 mL×2), brine (10 mL), dried over Na$_2$SO$_4$, and filtered. The filtrate was then evaporated under reduced pressure to give a pale yellow solid (crude 14.2 g, 88% recrystallized with MeOH or 12.0 g. MS M+H=186 found: 186, $^1$H NMR structure confirmed).

Example 3

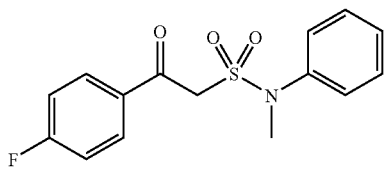

3

To a THF solution (20 mL) containing the methanesulfonamide 2 (2.5 g) at −78° C. was dropwise added n-butyllithium (10.3 mL of 2.5 M in Hexane). The reaction mixture was then warmed to 0° C. and cooled back to −78° C. before methyl p-fluorobenzoate (2.5 g in THF (5 mL)) was added. The reaction mixture was stirred for 1 h after the dry ice bath was removed. Work-up: The reaction mixture was concentrated under reduced pressure, and the resultant suspension was treated with 1N aqueous HCl solution. Once acidified the reaction mixture was extracted with DCM (10 mL×2). The organic phase was then washed with water (10 mL×2), dried over Na$_2$SO$_4$, and filtered. The filtrate then was evaporated under reduced pressure to give a white solid (4.47 g MS M+H=308 found: 308, $^1$H NMR structure confirmed).

Example 4

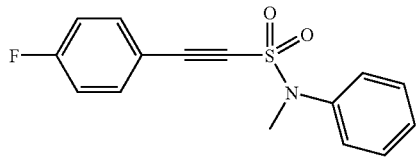

4

Dry triethylamine (3 mL) was slowly added to a DCM solution (5 mL) containing the β-ketosulfonamide 3 (460 mg, 1.5 mmole) and 2-chloro N-methylpyridinium iodide (511 mg, 2.0 mmole) at ambient temperature. The suspension was stirred at room temperature for 2 days. To take a TLC a small aliquot of the sample was treated with 1 N NaOH, extracted with DCM. The TLC spot was taken from the organic phase. Work-Up: After 2 days, the suspension was treated with 1N NaOH (5 mL) for 5 min. Then it was extracted with DCM (20 mL×2). This organic phase was successively washed with 1N NaOH, 1N HCl, water, dried over Na$_2$SO$_4$, and filtered. The filtrate was then passed through a short column of basic alumina. The resultant DCM solution was then evaporated under reduced pressure to give a yellow solid (282 mg, 0.975 mmole, 65%).

Example 5

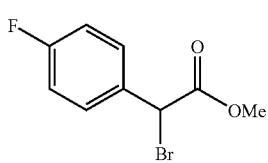

5$_b$

To a dry MeOH solution (50 mL) containing 4-fluorophenylacetic acid $5_a$ (5 g, 0.0324 mole) was added a catalytic amount of 4-toluene sulfonicacid (0.324 mmole, 61 mg). The solution was refluxed for 4 h. The resultant solution was concentrated under reduced pressure to give pale-yellow syrup. The material was diluted with EtOAc (100 mL), and neutralized with NaHCO$_3$ (1M, 5 mL). The organic layer was then washed with H$_2$O (10 mL×2), followed by brine (10 mL), dried over MgSO$_4$ and filtered. The filtrate was concentrated to give a pale-yellow liquid. (5.33 g, 31.75 mmole, 98%, MS M+H=169 found: 169, $^1$H NMR structure confirmed).

The methyl ester (2.0 g, 11.9 mmole) was then added to a CCl$_4$ solution (100 mL) containing NBS (2.33 g, 13.09 mmole). The reaction mixture was refluxed at 80° C. for 3 h to yield the brominated methyl ester $5_b$. The cooled solution was filtered through a pad of silica gel to remove excess succinimide, the filtrate was evaporated under reduced pressure, and the resultant material was transferred to the next reaction without further purification.

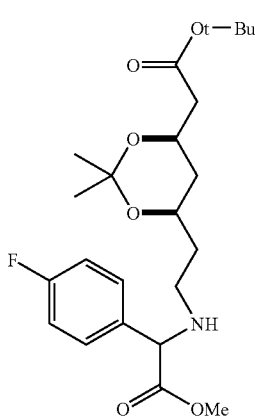

$5_c$

To an acetonitrile solution containing the amine (TBIA, 2.44 g (8.94 mmole)/15 mL ACN) was added the compound $5_b$ (ca. 2 g). While the reaction mixture was stirred triethylamine was added dropwise (1.70 mL, 12.2 mmole 1.5 equiv.). The reaction mixture was stirred at ambient temperature for 16 h. After completion of the reaction, the reaction mixture was concentrated under reduced pressure, and diluted with EtOAc (25 mL). The organic layer was treated with H$_2$O, dried over MgSO$_4$, and filtered. The filtrate was then concentrated under reduced pressure to give the compound $5_c$, 3.29 g.

Isobutyryl chloride (0.53 mL, 4.99 mmole in 5 mL DCM) was added dropwise to a chilled DCM solution (10 mL) containing the compound $5_c$ (2.0 g, 4.54 mmole). While the reaction mixture was stirred, a triethylamine solution (1.27 mL, 2 equiv. in 5 mL DCM) was added dropwise. The reaction mixture was agitated as it was warmed to room temperature for 2 h. After completion of the reaction, the reaction mixture was treated with 1N HCl (20 mL), followed by sat. NaHCO$_3$ (3 mL). The organic layer was then washed with water and brine, dried over MgSO$_4$, and filtered. The filtrate was concentrated under reduced pressure to give pale-yellow syrup. This was purified by a column chromatography using a gradient of EtOAc-Hexane mixture (from 0 to 25% of EtOAc). The isolated yield of the methyl ester was 2.10 g, 4.13 mmole, 90.9%.

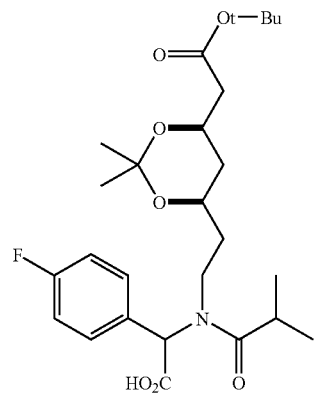

5

The methyl ester (250 mg, 0.50 mmole) was dissolved in a LiOH solution (1M, THF:water (5:1) mixture), and vigorously stirred for 3 h. The reaction mixture was neutralized to pH 7 by titrating it with 1N HCl solution. The desired product was then extracted with EtOAc (20 mL). The organic layer was washed with H$_2$O and brine, dried over MgSO4, and filtered. The filtrate was then evaporated under reduced pressure to give a white amorphous material 5 (200 mg, 0.40 mmole, 80%, MS M+H=496 found: 496, $^1$H NMR structure confirmed).

Example 6

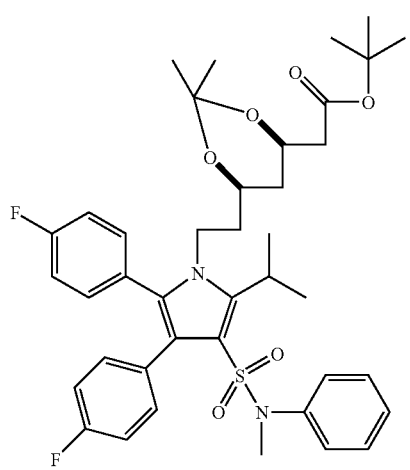

6

To a toluene solution (5 mL) containing the compounds 4 (0.38 g, 1.30 mmole) and 5 (0.450 g, 0.91 mmole) was added acetic anhydride (0.30 mL). The reaction mixture was heated to 50° C. and stirred at that temperature for 2 h. After the reaction was complete, the reaction mixture was evaporated under reduced pressure to give a dark amorphous material from which desired product (compound 6, 499 mg, 0.690 mmole, 76%) was isolated through a column chromatography using a gradient of EtOAc-Hexane mixture (from 0 to 20% of EtOAc).

Example 7

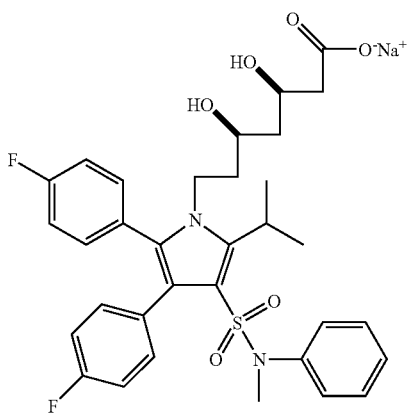

To a DCM solution (5 mL) containing the pyrrolesulfonamide 6, was added 10 (v/v) % TFA in DCM (5 mL) at once at room temperature. The reaction mixture was stirred for 1 h to be complete, and was evaporated under reduced pressure to give a pale yellow amorphous material (yield: 0.25 g, 99%, MS M+H=609 found: 609, $^1$H NMR structure confirmed).

The lactone (250 mg, 0.411 mmole) was dissolved in THF (5 mL), and to this solution was added 1 N NaOH solution (400 μL). After 2 h most of the lactone disappeared in TLC ($R_f$=0.11 in a 7:3 mix hex:EtOAc) to give a baseline spot. The additional NaOH solution (11 μL) was added dropwise. The solution was stirred for an additional 1 h, and was evaporated under reduced pressure. The resultant solid was then re-dissolved in water and frozen, and was lyophilized overnight to yield a white solid 7 (0.211 g, 0.325 mmole, 79%, MS M+H=649 found: 649, $^1$H NMR structure confirmed).

Example 8

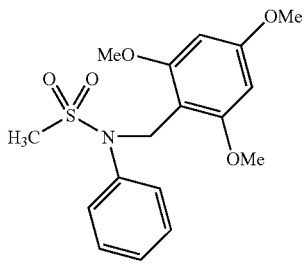

To a DCM solution (50 mL) containing methanesulfonyl chloride 1 (1.614 g, 14.1 mmole) at 0° C. was added 2,4,6-trimethoxybenzylaniline (3.50 g, 13 mmole), followed by dropwise addition of triethylamine (2.68 mL, 19.2 mmole). The reaction mixture was stirred at 0° C. for 1 h and slowly warmed to room temperature. Work-up: The reaction mixture was evaporated under reduced pressure, and 1N HClsolution was added until the pH of the solution was neutral.

The desired compound was extracted using EtOAc (25 mL×2), and the organic phase was washed with water (20 mL×2), and brine (10 mL), dried over Na$_2$SO$_4$, and filtered. The filtrate was then evaporated under reduced pressure to give a pale yellow solid. The product was recrystallized using hot MeOH. Yield: crude: 3.80 g, 84%, recrystallization: 3.11 g.

Example 9

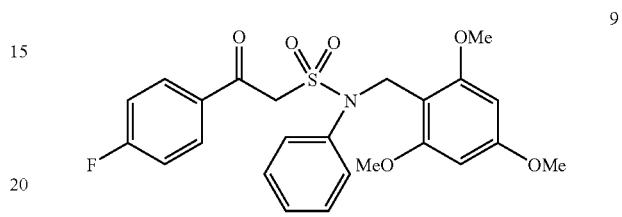

To a THF solution (7.5 mL) containing 8 (1.5 g) at −78° C. was added dropwise n-butyllithium (0.41 mL of 2.5 M in Hexane). The reaction mixture was then warmed to 0° C. and cooled back to −78° C. before methyl p-fluorobenzoate (0.158 g in THF (2.5 mL)) was added. The reaction mixture was stirred for 1 h after the dry ice bath was removed. Work-up: The reaction mixture was concentrated under reduced pressure, and the resultant suspension was treated with 1N HCl solution. Once acidified, the reaction mixture was extracted with DCM (10 mL×2). The organic phase was then washed with water (5 mL×2), dried over Na$_2$SO$_4$, and filtered. The filtrate then was evaporated under reduced pressure to give a white solid (1.527 g, 71.9%).

Example 10

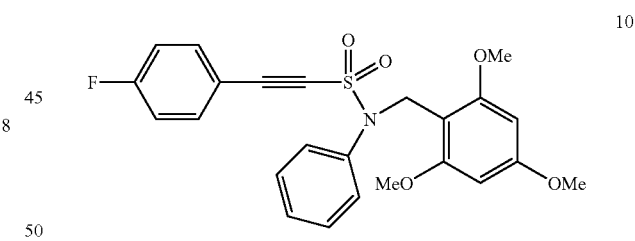

Dry triethylamine (5 mL) was slowly added to a DCM solution (5 mL) containing the β-ketosulfonamide 9 (721 mg, 1.52 mmole) and 2-chloro N-methylpyridinium iodide (580 mg, 2.3 mmole) at ambient temperature. The suspension was stirred at room temperature for 2 days. To take a TLC, a small aliquot of the sample was treated with 1 N NaOH, extracted with DCM. The TLC spot was taken from the organic phase. Work-Up: After 2 days, the suspension was treated with 1N NaOH (5 mL) for 5 min. Then it was extracted with DCM (20 mL×2). This organic phase was successively washed with 1N NaOH, 1N HCl, water, dried over Na$_2$SO$_4$, and filtered. The filtrate was then passed through a short column of basic alumina. The resultant DCM solution was then evaporated under reduced pressure to give a yellow solid (520 mg, 75%).

Example 11

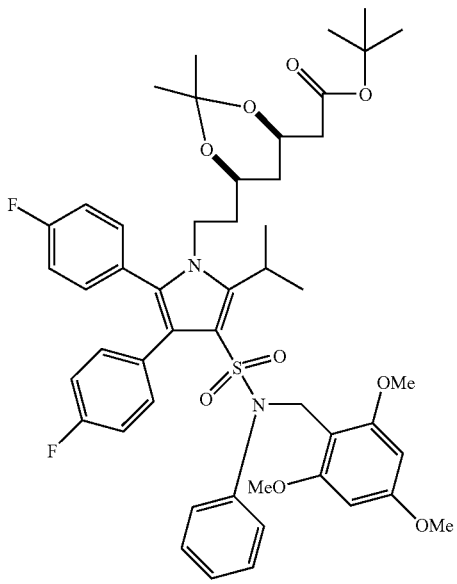

To a toluene solution (5 mL) containing the compounds 10 (0.342 g, 1.10 mmole) and 5 (0.560 g, 0.751 mmole) was added acetic anhydride (0.30 mL). The reaction mixture was heated to 50° C. and stirred at the temperature for 2 h. After the reaction was complete, the reaction mixture was evaporated under reduced pressure to give a dark amorphous material from which the desired product (compound 11, 540 mg, 0.607 mmole, 80.9%) was isolated through column chromatography using a gradient of EtOAc-Hexane mixture (from 0 to 20% of EtOAc).

Example 12

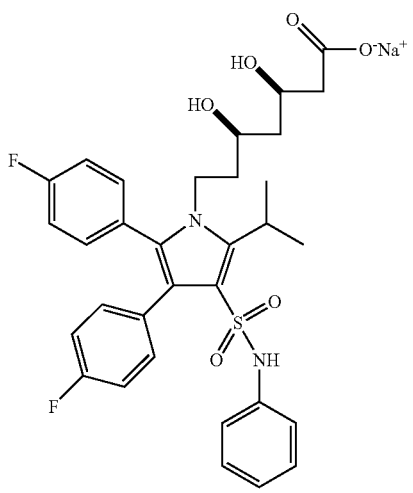

To a DCM solution (5 mL) containing the pyrrolesulfonamide 11 (0.350 g, 0.394 mmole), was added 10 (v/v) % TFA in DCM (5 mL) at once at room temperature. The reaction mixture was stirred for 1 h to be complete, and was evaporated under reduced pressure to give a pale yellow amorphous material (yield: 0.199 g, 85%, MS M+H=595 found: 595, $^1$H NMR structure confirmed).

The lactone (90777×048, 69.7 mg, 0.117 mmole) was dissolved in THF (5 mL), and to this solution was added 1 N NaOH solution (100 µL). After 2 h most of the lactone disappeared in TLC in a 7:3 mix hex:EtOAc to give a baseline spot. The additional NaOH solution (17 µL) was added dropwise. The solution was stirred for an additional 1 h, and was evaporated under reduced pressure. The resultant solid was then re-dissolved in water and frozen, and was lyophilized overnight to yield a white solid 12 70 mg, 0.114 mmole, 97%, MS M+H–Na$^+$=612 found: 612, $^1$H NMR structure confirmed).

Example 13

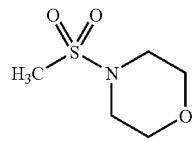

To a DCM solution (50 mL) containing methanesulfonyl chloride at 0° C. was added morpholine, followed by dropwise addition of triethylamine. The reaction mixture was stirred at 0° C. for one hour and slowly warmed to room temperature. The TLC result showed a spot to spot transformation of the morpholine ($R_f$=0.02 to 0.20 in 30% EtOAc/Hex, iodine chamber). Work-up: The reaction mixture was evaporated under reduced pressure, and 1N HCl was added until the pH of the solution was acidic. The desired compound was extracted using EtOAc (25 mL×2), and the organic phase was washed with water (20 mL×2), and brine (10 mL), dried over Na$_2$SO$_4$ and filtered. The filtrate was then evaporated under reduced pressure to give a pale yellow solid (8.06 g, 56%).

Example 14

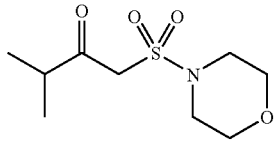

To a THF solution (30 mL) containing morpholino methanesulfonamide (2.0 g) at −78° C. was dropwise added n-butyllithium (6.4 mL of 2.5 M in Hexane). The reaction mixture was then warmed to 0° C. and cooled to −78° C. before methyl isobutyrate (1.081 g in THF (5 mL)) was added. The reaction mixture was stirred for 1 h after the dry ice bath was removed. Work-up: The reaction mixture was acidified with 1N HCl (5 mL) and then concentrated under reduced pressure. The resultant material was extracted with EtOAc, and the organic phase was washed with water, brine, dried over Na$_2$SO$_4$ and filtered. The filtrate was then evaporated under reduced pressure to yield a pale yellow liquid (1.87 g, crude). The crude material was then purified by column chromatography (a 4:1 mixture of Hex. and EtOAc as eluent) to give a transparent liquid (1.16 g).

Example 15

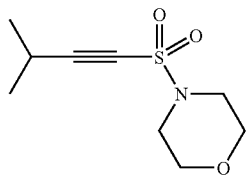

To a DCM solution containing the β-ketosulfonamide 14 (150 mg, 0.638 mmol in 3 mL DCM) was added Hunig's base (333 uL) at 0° C., followed by trifluoromethanesulfonic anhydride (133 uL). The reaction mixture was stirred at the temperature for 24 h. Work-up: The reaction mixture was treated with 1 N aqueous $NH_4Cl$ solution, and the aqueous phase was extracted with DCM (3×10 mL). The combined extracts were washed with sat. aqueous $NH_4Cl$ solution (2×10 mL), water (2×10 mL), dried over MgSO4 and concentrated under reduced pressure. Flash column chromatography of the resulting crude product on silica gel (a gradient up to 30% EtOAc in Hexane) gave of the desired alkynesulfonamide 15 (75 mg, 0.343 mmole, 54%, MS M+H=217 found: 217, $^1$H NMR structure confirmed, IR=2193 $cm^{-1}$).

Example 16

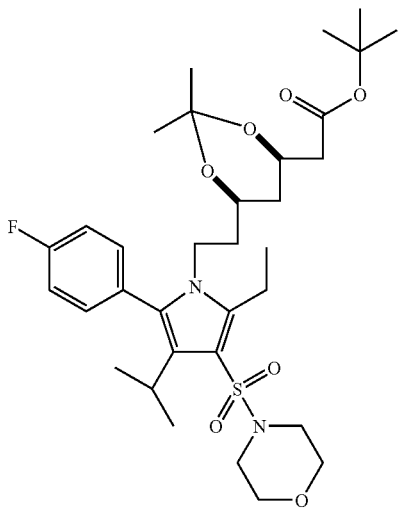

A trifluorotoluene solution (5 mL) containing compound 5'* (0.554 g, 2.5 equiv.) and compound 15 (0.100 g, 0.46 mmole) and acetic anhydride (100 μL) was treated under microwave conditions (180° C., 10 min). After the reaction was complete, the reaction mixture was concentrated under reduced pressure to give a dark brown amorphous material. The compound was submitted for purification and structure analysis. The MS analysis gave the desired mass of the product (M+H 637 found 637).

Example 17

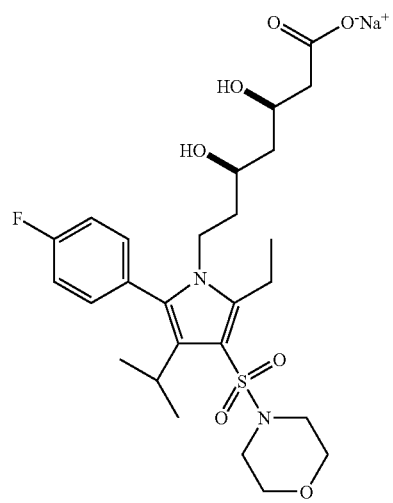

To a DCM solution (10 mL) containing 16 (320 mg, 0.5025 mmole) was added TFA ((2.5 mL) at 0° C. The ice bath was removed after 30 minutes. After 2 h the reaction was complete, the resultant solution was evaporated under reduced pressure to give a pale yellow amorphous material. Work-up: The amorphous material dissolved in 25 mL of DCM and treated with 5 mL of 1N $NaHCO_3$ solution followed by washing with water (2 mL). The organic layer was then dried over $MgSO_4$, filtered. The filtrate was evaporated under reduced pressure to give a pale-yellow amorphous material from which the desired material was isolated by column chromatography (50% EtOAc in hex). Isolated yield: 0.190 g, 72.3%. The lactone (120 mg, 0.223 mmole) was dissolved in THF (5 mL), and to this solution was added 1 N NaOH solution (100 uM). After 2 h most of the lactone disappeared in TLC ($R_f$=0.11 in a 2:8 mixture of hexane: EtOAc) to give a baseline spot. The additional NaOH solution (20 uL) was added a drop-wise manner. The solution was stirred for an additional 1 h, and was evaporated under reduced pressure. The resultant solid was then re-dissolved in water and the solution was frozen, and lyophilized overnight to yield a white solid (129 mg, 0.223 mmole: Yield, 99.8%).

Scheme 7, below, relates to preparation of Intermediates 1-10 and Example 18.

Scheme 7

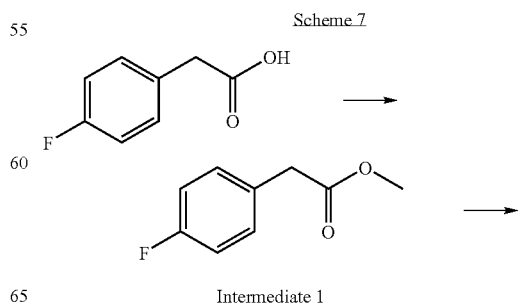

Intermediate 1

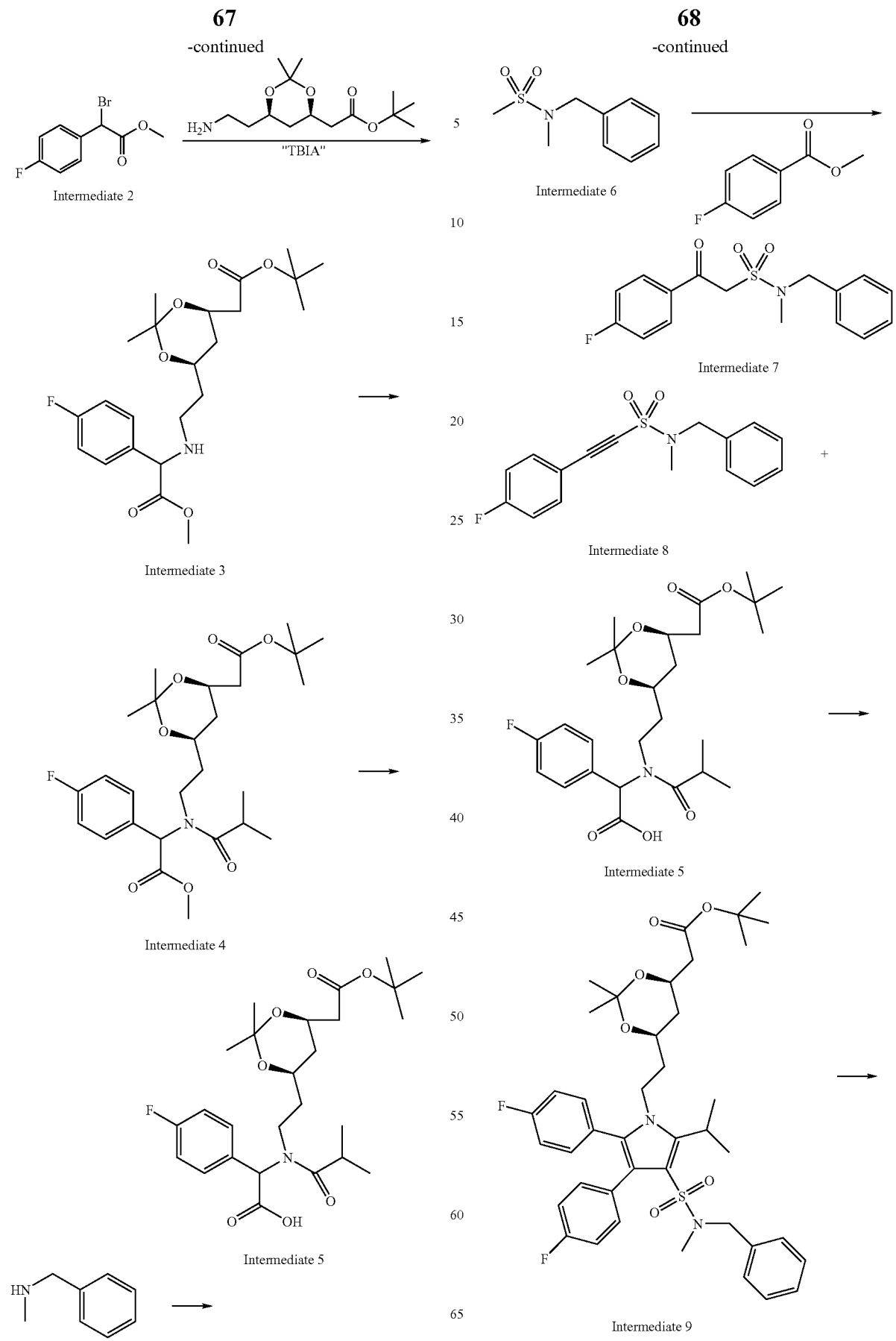

-continued

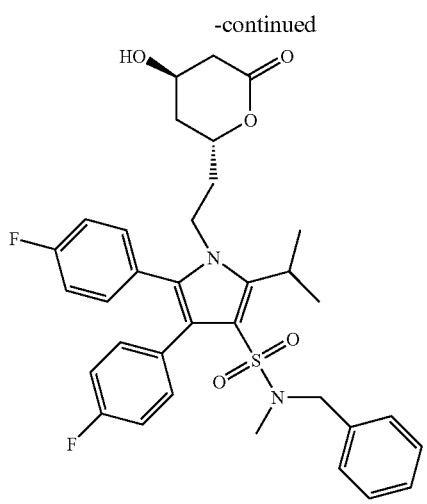

Intermediate 10

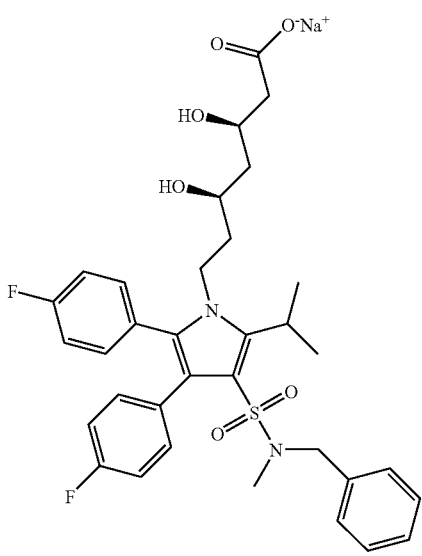

Example 18

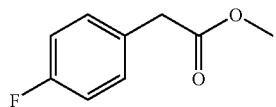

Intermediate 1

A solution of 100 g (0.64 mol) of 4-fluorophenylacetic acid, 0.5 g (2.6 mmol) of p-toluenesulfonic acid in 600 ml of methanol was refluxed with stirring for 3 h. After cooling, the reaction was concentrated and the residue taken up in ethyl acetate. Organics washed with a saturated NaHCO$_3$ solution, water, and brine. Dried over sodium sulfate, filtered, and concentrated to yield 101.5 grams of a clear liquid. MS AP+169.0 (M+1), AP-167.0 (M-1).

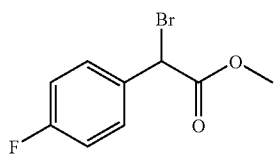

Intermediate 2

Solution of 25.5 g (0.15 mol) of intermediate 1 in 50 ml of carbon tetrachloride was treated with 29.7 g (0.167 mol) of N-bromosuccinimide in 50 ml of carbon tetrachloride. Mixture was treated with 12 drops of HBr/HOAc (30%) and stirred at reflux for 2 h. Treated with another 5 g (0.03 mol) of N-bromosuccinimide and stirred at reflux for 2 h. Cooled and reaction was filtered through a mixture of magnesium sulfate/silica gel (1:1). Concentrated to yield 36.89 g of liquid.

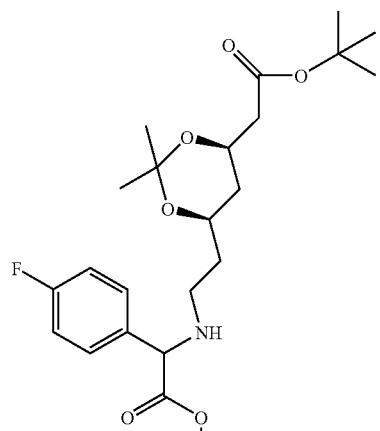

Intermediate 3

Solution of 44.87 g (0.164 mol) of amine (TBIA) in 180 ml of acetonitrile was treated with a solution of 36.89 g (0.149 mol) of intermediate 2 in 90 ml of acetonitrile. Mixture was treated with 31.2 ml (0.224 mol) of triethylamine dropwise and stirred overnight at room temperature. Reaction was concentrated and the residue taken up in ethyl acetate and washed with water (2×). Organics were dried over sodium sulfate, filtered, and concentrated to yield approximately 69 g of a thick oil. MS APCI+440.2 (M+1).

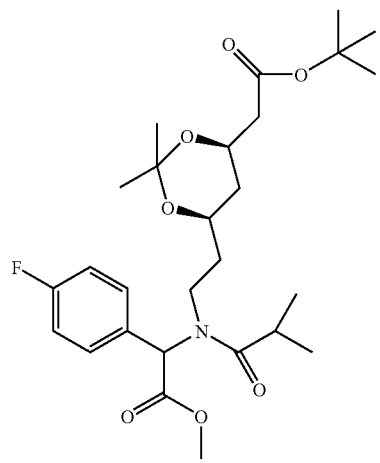

Intermediate 4

Ice cold solution of intermediate 3 (69 g, 0.149 mol) in 320 ml of cold dichloromethane was treated dropwise with a solution of 17.3 ml (0.164 mol) of isobutyryl chloride in 160 ml of cold dichloromethane. Mixture stirred for 5 minutes and treated dropwise with 41.6 ml (0.299 mol) of triethylamine in 50 ml of cold dichloromethane. Stirred in an ice bath for 1 h and allowed to warm to room temperature. After 4 h, the reaction was treated with 400 ml of dichloromethane and 150 ml of 1N HCl and separated quickly. The organics were washed with saturated NaHCO₃, water, and brine. Dried over sodium sulfate, filtered, and concentrated to yield around 78 g of a thick oil. A 30 g portion was chromatographed on silica gel eluting with ethyl acetate/hexanes (5-50%) to yield 19.46 g of a thick oil. MS APCI+510 (M+1).

Intermediate 5

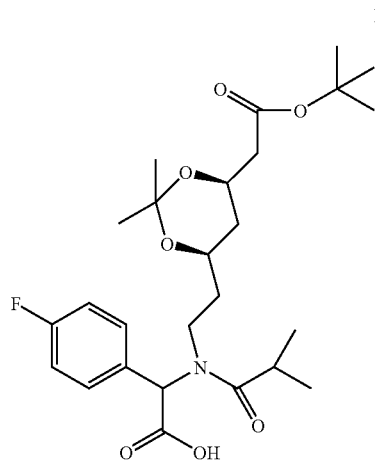

Solution of 10.91 g (21.4 mmol) of intermediate 4 in 150 ml of methanol was treated with 50 ml of 1N LiOH and stirred at room temperature for 3 h. The reaction was concentrated and the residue treated with 30 ml of water. Treated with 1N HCl until pH~7 and extracted with ethyl acetate. Washed organics with brine, dried over sodium sulfate, and concentrated to yield 10.02 g of a foam. MS APCI–494.1 (M–1).

Intermediate 6

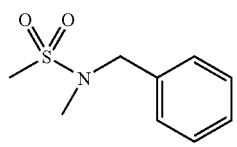

Ice cold solution of 6.77 ml (0.086 mol) of messy chloride in 125 ml of dry dichloromethane was treated slowly with 14.4 ml (0.108 mol) of N-benzylmethylamine and then slowly with 15.2 ml (0.108 mol) of triethylamine. Stirred in an ice bath for 0.5 h and at room temperature for 0.5 h and concentrated. Residue taken up in ethyl acetate and 1N HCl and separated. Organics washed with water (2×) and brine (1×) and then dried over sodium sulfate. Concentrated to yield 17.54 g of a liquid. MS APCI+200.1 (M+1).

Intermediate 7

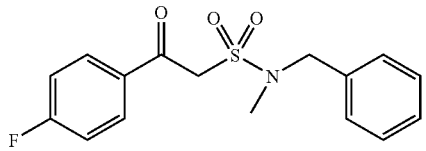

Solution of 3.23 g (16.2 mmol) of intermediate 6 in 20 ml of dry tetrahydrofuran at –78° C. was treated dropwise with 6.6 ml (16.5 mmol) of 2.5M n-BuLi in hexanes. Reaction stirred in an ice bath for 0.5 h and then cooled again to –78° C. Treated dropwise with 2.09 ml (16.2 mmol) of methyl 4-fluorobenzoate. Stirred at room temperature for 1 h. Concentrated and residue treated with 1N HCl until pH~3, diluted with 10 ml water, and extracted with ethyl acetate. Organics washed with brine, dried over sodium sulfate, and concentrated to yield 4.34 g of an oil. Chromatographed on silica gel eluting with ethyl acetate/hexanes (0-20%) to yield 1.06 g of an oil. MS APCI+322.0 (M+1), APCI–320.1 (M–1).

Intermediate 8

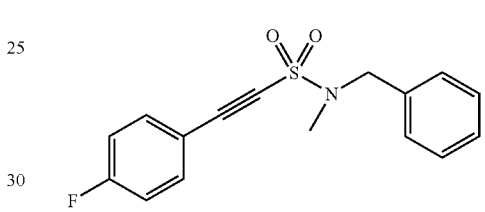

Mixture of 0.88 g (2.75 mmol) of intermediate 7 and 1.32 g (5 mmol) of 2-chloro-N-methylpyridinium iodide in 5.5 ml of dichloromethane was treated dropwise with 8 ml (0.06 mol) of triethylamine, capped and stirred for 3 days at room temperature. Treated with 8.25 ml of 1N NaOH and stirred for 5 min. Extracted with dichloromethane and washed organics with 1N NaOH, 1N HCl, and water. Dried over sodium sulfate and concentrated. Residue was taken up in 5 ml dichloromethane and filtered through 5 g of alumina. Concentrated to yield 0.72 g of solid. MS AP+304.0 (M+1).

Intermediate 9

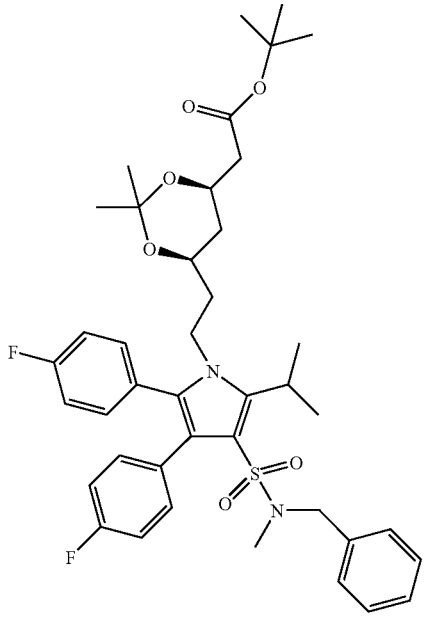

Mixture of 0.5 g (1.65 mmol) of intermediate 8 and 0.83 g (1.68 mmol) of intermediate 5 in 6 ml of toluene was treated with 0.36 ml of acetic anhydride and stirred at 60° C. After 2 h, TLC showed reaction was not complete. Treated with another 0.05 g (0.1 mmol) of intermediate 5 and continued stirring with heat for 2 h. Concentrated and the residue was taken up in ethyl acetate and washed with water. Dried over sodium sulfate and concentrated to yield a film which was chromatographed on silica gel eluting with ethyl acetate/hexanes (0-25%) to yield 0.71 g of a foam. MS APCI+737.1 (M+1).

Solution of 242.5 mg (0.39 mmol) of intermediate 10 in 8.5 ml of tetrahydrofuran was treated with 334 μL of 1N NaOH and stirred at room temperature for 2 h. Reaction was not complete. Treated with another 60 μL of 1N NaOH and stirred for 1 h. Concentrated and residue taken up in water, frozen, and lyophilized overnight. Collected 0.276 g of a white solid. MS (parent) APCI+641.1 (M+1).

CHN Calc with 2.5H$_2$O: C, 57.69; H, 5.98; N, 3.96. Found: C, 57.87; H, 5.58; N, 3.79.

Scheme 8, below, relates to preparation of Intermediates 11-15 and Example 19.

Intermediate 10

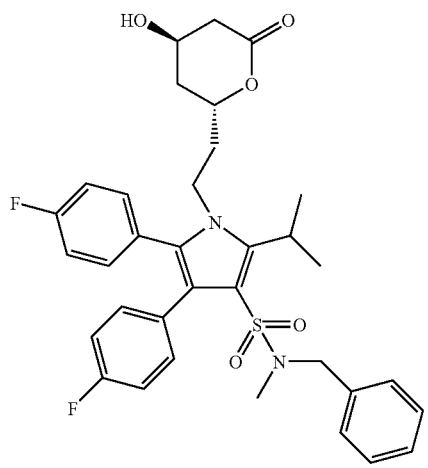

0.35 g (0.47 mmol) of intermediate 9 was treated with 10 ml of TFA/DCM (1:9) and stirred at room temperature for 1.5 h. Concentrated and residue taken up in ethyl acetate and washed with saturated NaHCO$_3$, and water. Dried organics over sodium sulfate and concentrated to yield 319 mg of a foam. MS APCI+623.1 (M+1).

Example 18

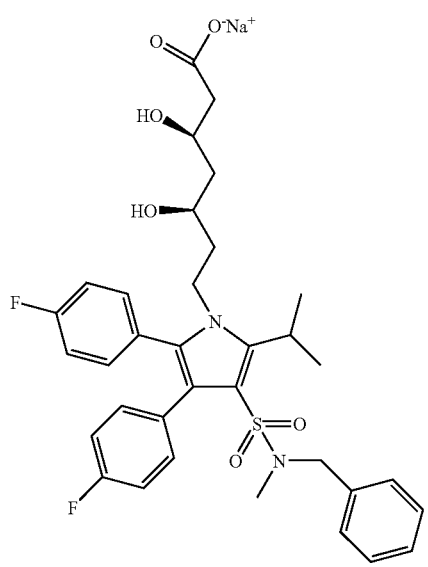

Scheme 8

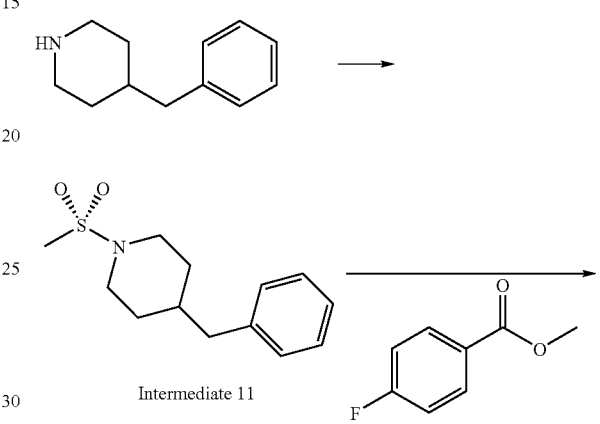

Intermediate 11

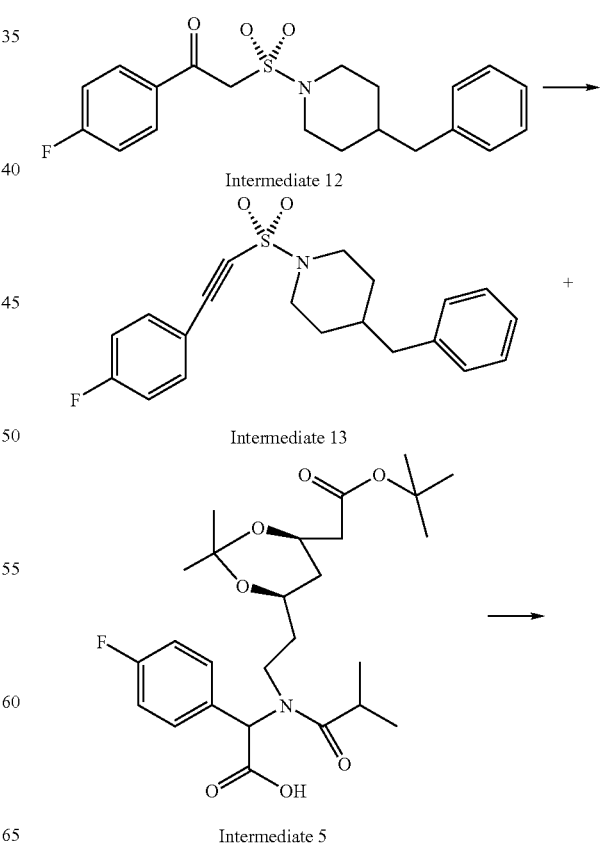

Intermediate 12

Intermediate 13

Intermediate 5

-continued

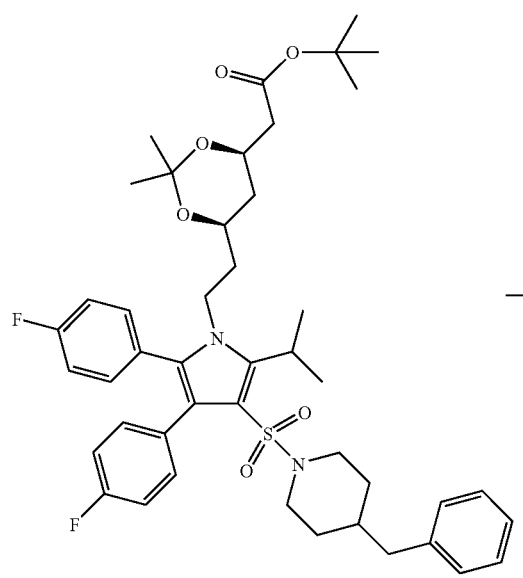

Intermediate 14

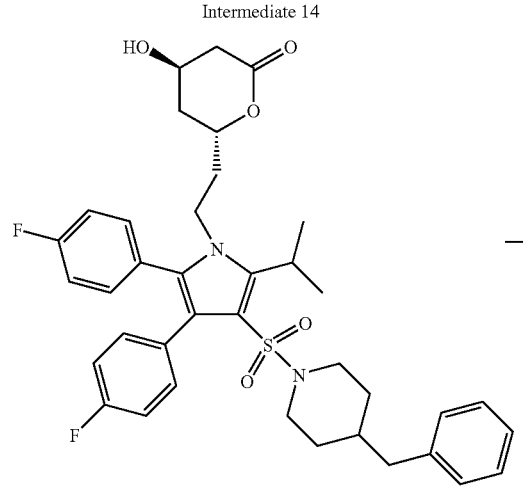

Intermediate 15

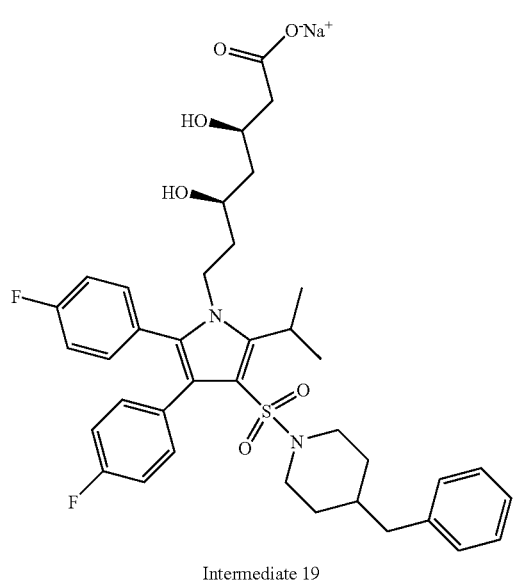

Intermediate 19

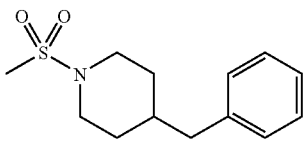

Intermediate 11

Procedure as in intermediate 6 using 19.2 ml (0.108 mol) of 4-benzylpiperidine to yield 21.65 g of a yellow solid. MS APCI+254.1 (M+1).

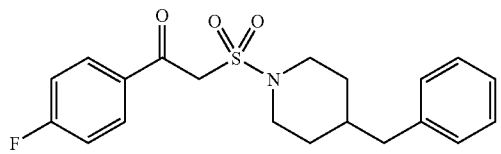

Intermediate 12

Procedure as in intermediate 7 using 4.31 g (17.01 mmol) of intermediate 11 and 6.8 ml (17.01 mmol) of 2.5M n-BuLi in hexanes to yield 6.23 g of solid which was recrystallized from methanol to give 2.96 g of white solid. MS APCI+ 376.0 (M+1), APCI−374.1 (M−1).

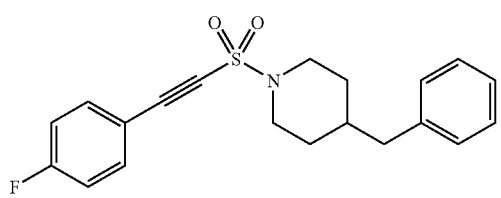

Intermediate 13

Procedure as in intermediate 8 using 1.03 g (2.75 mmol) of intermediate 12 to yield 0.9 g of a film. MS AP+358.1 (M+1).

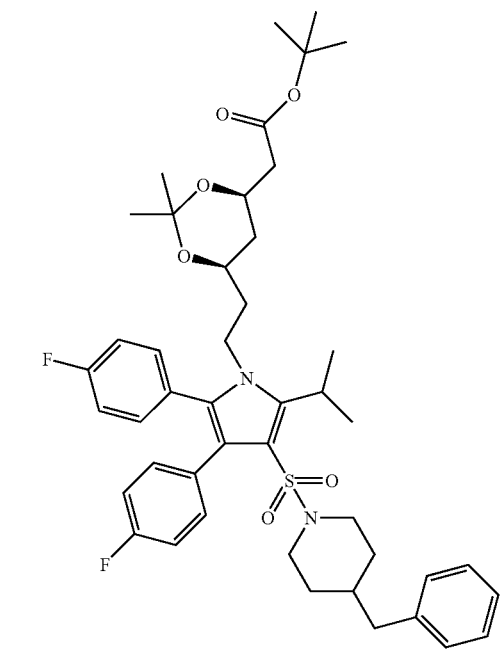

Intermediate 14

Procedure as in intermediate 9 using 0.9 g (1.82 mmol) of intermediate 5 and 0.59 g (1.65 mmol) of intermediate 13. Chromatography gave 0.61 g of a film. MS APCI+791.1 (M+1).

CHN Calc. with 3.0H₂O: C, 59.20; H, 6.36; N, 3.63. Found: C, 58.95; H, 5.89; N, 3.12.

Scheme 9, below, relates to Intermediates 16-19 and Example 20.

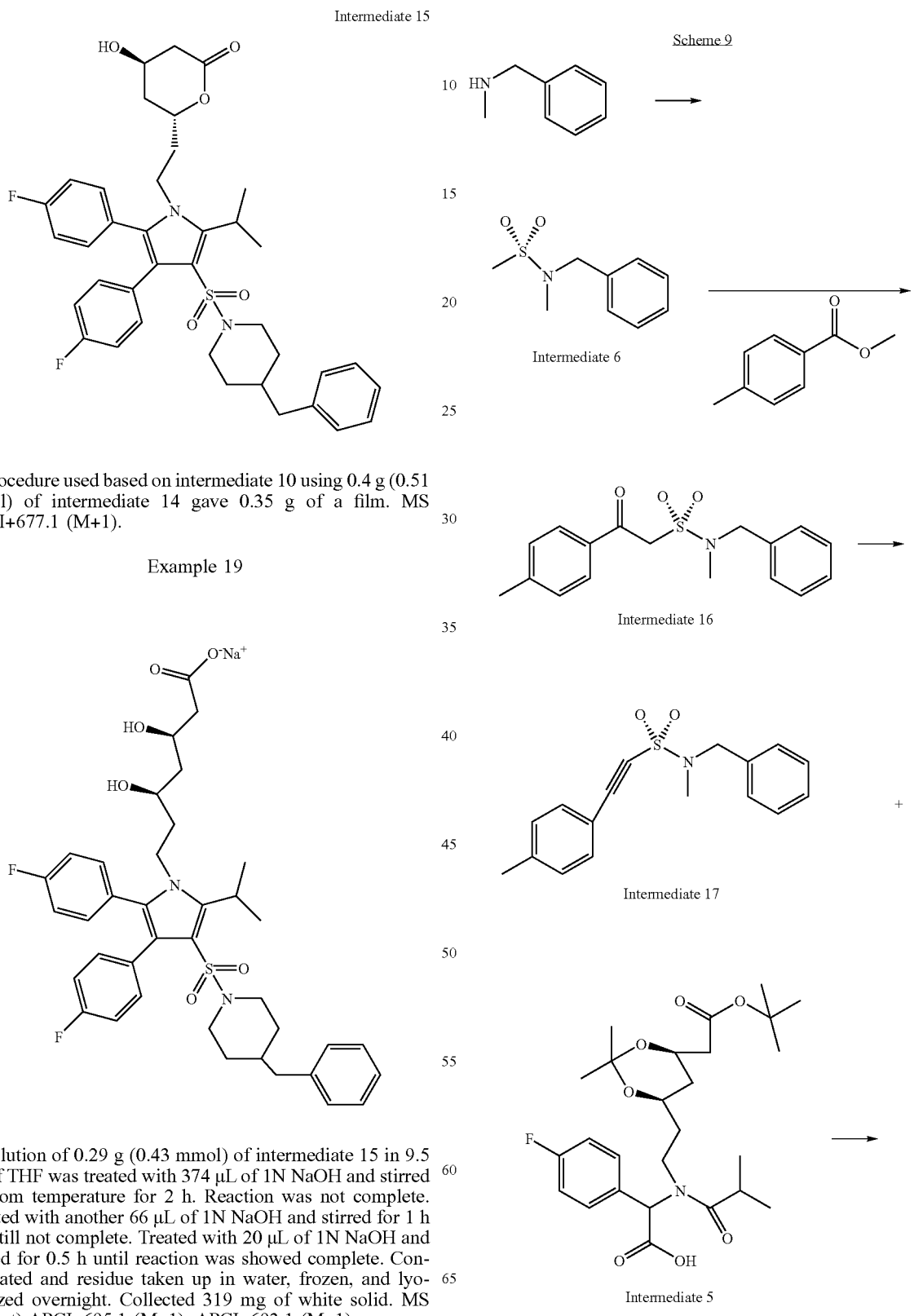

Procedure used based on intermediate 10 using 0.4 g (0.51 mmol) of intermediate 14 gave 0.35 g of a film. MS APCI+677.1 (M+1).

Example 19

Solution of 0.29 g (0.43 mmol) of intermediate 15 in 9.5 ml of THF was treated with 374 μL of 1N NaOH and stirred at room temperature for 2 h. Reaction was not complete. Treated with another 66 μL of 1N NaOH and stirred for 1 h but still not complete. Treated with 20 μL of 1N NaOH and stirred for 0.5 h until reaction was showed complete. Concentrated and residue taken up in water, frozen, and lyophilized overnight. Collected 319 mg of white solid. MS (parent) APCI+695.1 (M+1), APCI−693.1 (M−1).

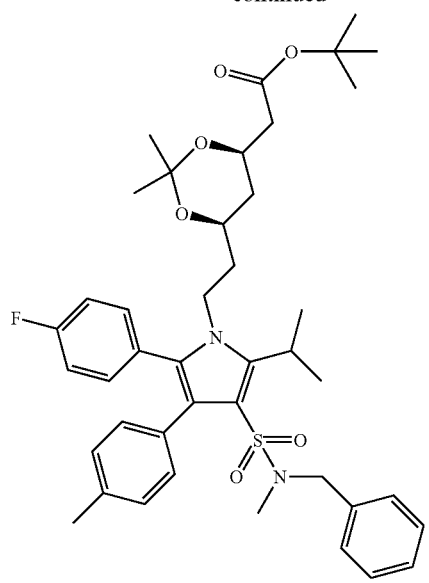

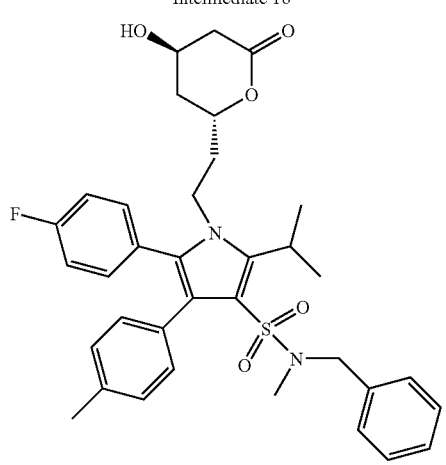

Intermediate 18

Intermediate 19

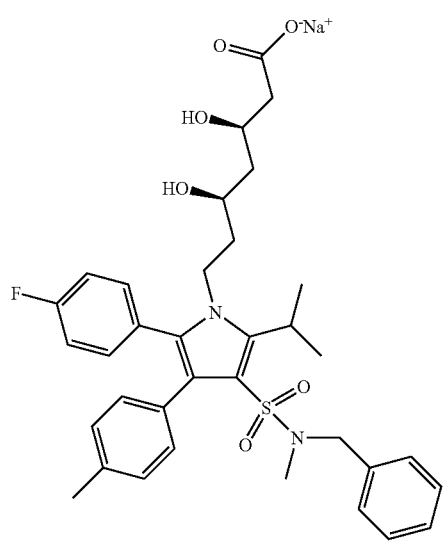

Example 20

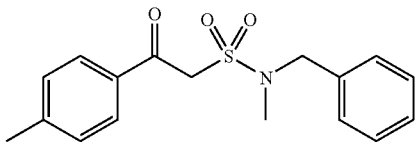

Intermediate 16

Procedure as in intermediate 7 using 3.39 g (17.01 mmol) of intermediate 6, 6.8 ml (17.01 mmol) of 2.5M n-BuLi in hexanes, and 2.46 g (16.2 mmol) of methyl 4-methylbenzoate gave 6.11 g of solid. Recrystallized from methanol to yield 2.11 g of white solid. MS APCI+318.1 (M+1), APCI–316.0 (M–1).

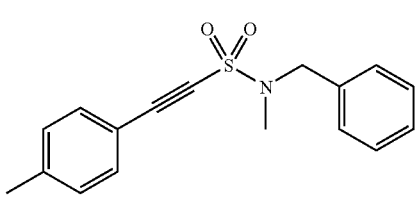

Intermediate 17

Procedure as in intermediate 8 using 0.87 g (2.75 mmol) of intermediate 16 yielded 0.77 g of solid. MS AP+300.1 (M+1).

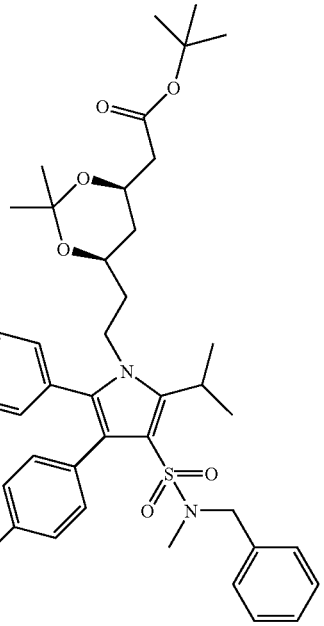

Intermediate 18

Mixture of 0.9 g (1.82 mmol) of intermediate 5 and 0.49 g (1.65 mmol) of intermediate 17 in 6 ml of toluene was treated with 0.36 ml of acetic anhydride and stirred at 60° C. for 4 h. Concentrated and chromatographed on silica gel eluting with ethyl acetate/hexanes (0-25%) to yield 0.75 g of white solid. MS APCI+733.1 (M+1).

Intermediate 19

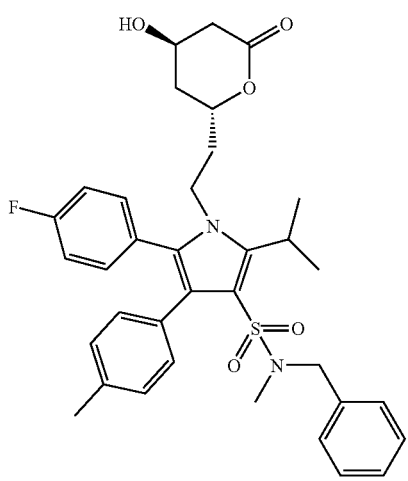

Procedure as in intermediate 10 using 0.35 g (0.48 mmol) of intermediate 18 gave a foam which was chromatographed on silica gel using a mixture of ethyl acetate/hexanes (gradient of 50% mixture to 75% mixture) to yield 0.29 g of a film. MS APCI+619.1 (M+1).

Example 20

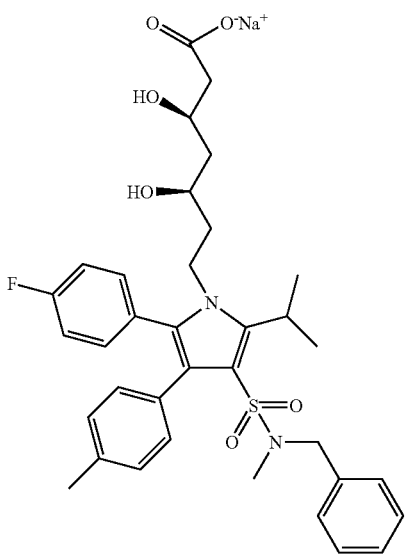

Solution of 0.23 g (0.37 mmol) of intermediate 19 in 8 ml of THF was treated with 322 µL of 1N NaOH and stirred at room temperature for 2 h. Reaction was not complete and was treated with another 60 µL of 1N NaOH and stirred for 1 h. Concentrated and residue taken up in water, frozen, and lyophilized overnight. Collected 254 mg of white solid. MS (parent) APCI+637.1 (M+1), APCI−635.1(M−1).

CHN Calc. With 4.18H$_2$O: C, 57.27; H, 6.64; N, 3.82.

Found: C, 56.88; H, 6.03; N, 3.32.

Scheme 10, below, relates to preparation of Intermediates 20-23 and Example 21.

Scheme 10

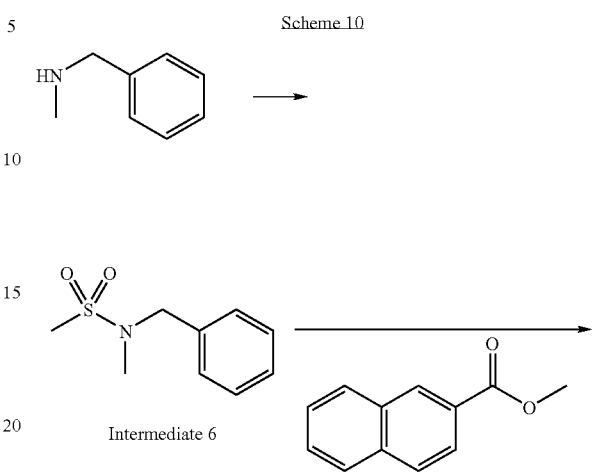

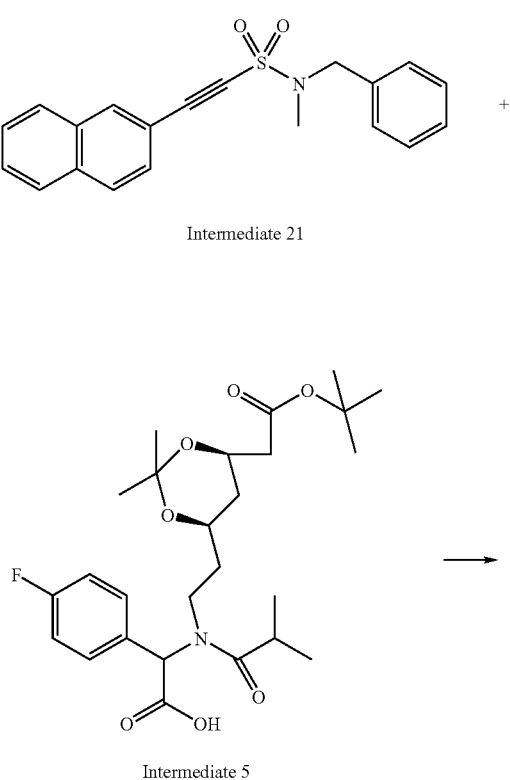

-continued

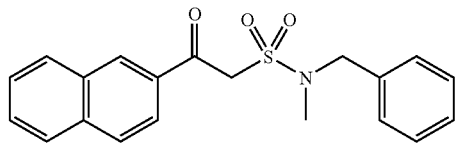

Intermediate 20

Procedure as in intermediate 7 using 3.39 g (17.01 mmol) of intermediate 6, 6.8 ml (17.01 mmol) of 2.5M n-BuLi in hexanes, and 3.10 g (16.2 mmol) of methyl 2-naphthoate gave 6.25 g of a thick oil. Recrystallized from methanol to yield 2.62 g of white solid. MS APCI+354.0 (M+1), APCI−352.0 (M−1).

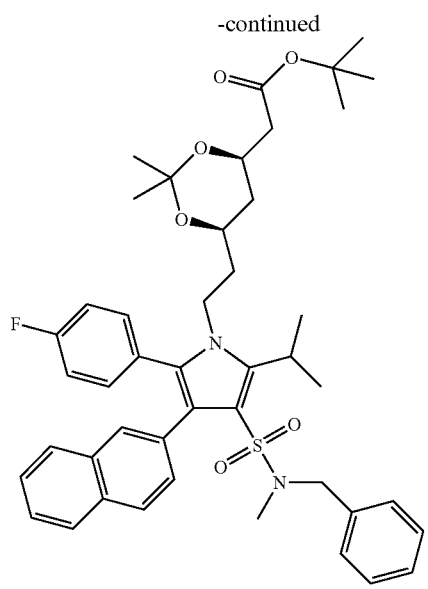

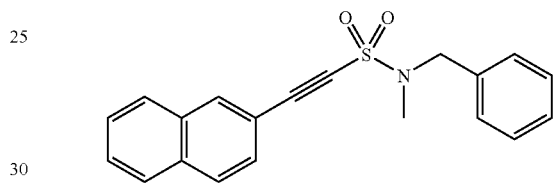

Intermediate 21

Procedure as in intermediate 8 using 0.97 g (2.75 mmol) of intermediate 20 gave 0.88 g of solid. MS AP+336.1 (M+1)

Intermediate 22

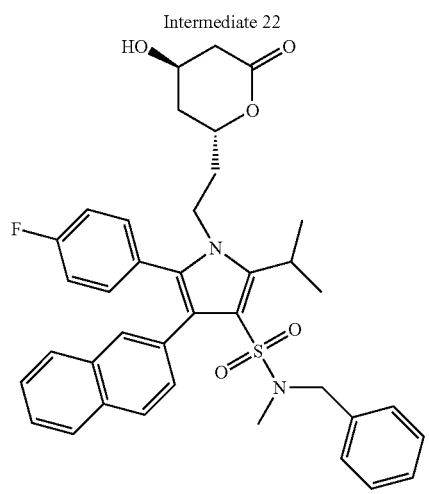

Intermediate 22

Intermediate 23

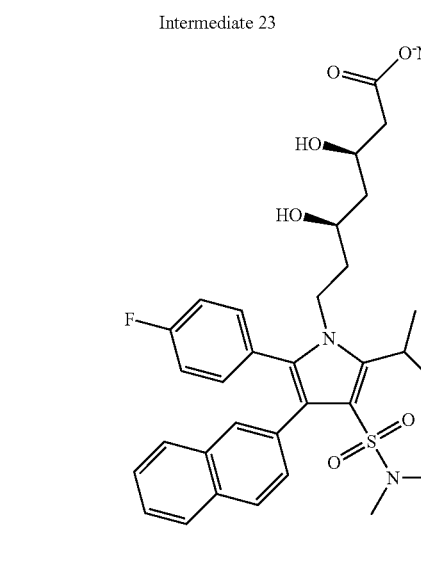

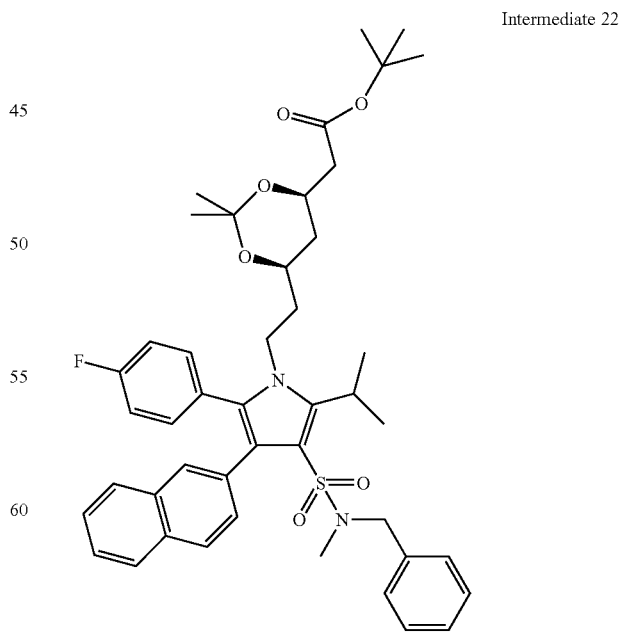

Example 21

Mixture of 0.9 g (1.82 mmol) of intermediate 5 and 0.55 g (1.65 mmol) of intermediate 21 in 6 ml of toluene was treated with 0.36 ml of acetic anhydride and stirred at 60° C. for 6 h. Concentrated and chromatographed on silica gel eluting with ethyl acetate/hexanes (0-25%) to yield 0.77 g of white solid. MS APCI+769.1 (M+1).

CHN Calc. for 2.81H$_2$O: C, 61.23; H, 6.16; N, 3.76.
Found: C, 60.83; H, 5.77; N, 3.42.

Scheme 12, below, relates to preparation of Intermediates 24-27 and Example 22.

Intermediate 23

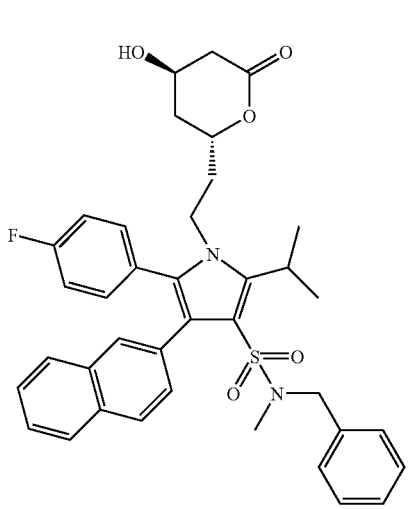

Procedure as in intermediate 10 using 0.40 g (0.52 mmol) of intermediate 22 gave a foam which was isolated by column chromatography using silica gel and a mixture of ethyl acetate/hexanes (gradient of 50% mixture to 75% mixture) to yield 0.31 g of a film. MS APCI+655.1 (M+1).

Example 21

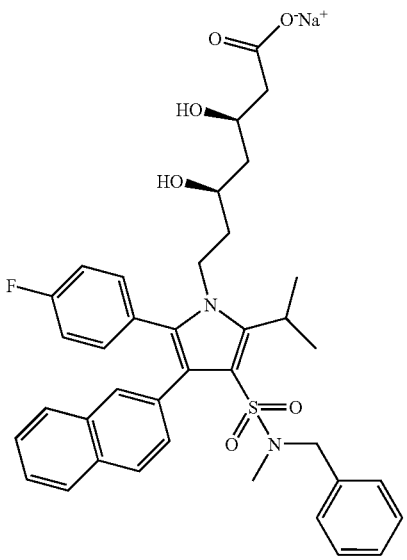

Solution of 0.258 g (0.39 mmol) of intermediate 23 in 8 ml of THF was treated with 338 μL of 1N NaOH and stirred at room temperature for 2 h. Reaction was not complete and was treated with another 50 μL of 1N NaOH and stirred for 1 h. Concentrated, residue taken up in water, frozen, and lyophilized overnight. Collected 278 mg of white solid. MS (parent) APCI+673.1 (M+1), APCI−671.1 (M−1).

Scheme 12

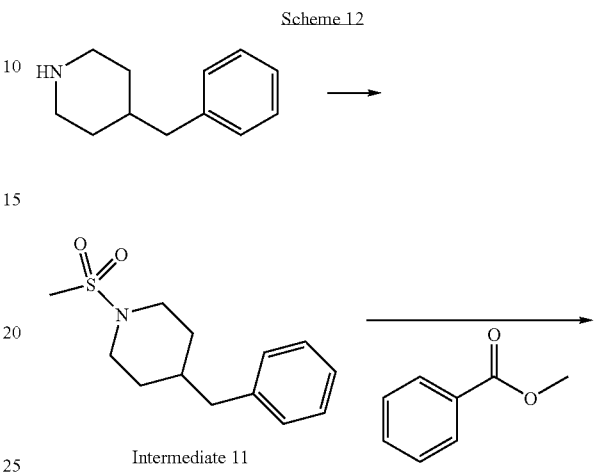

Intermediate 11

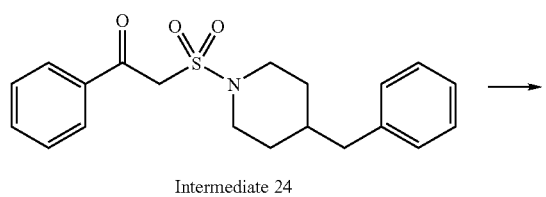

Intermediate 24

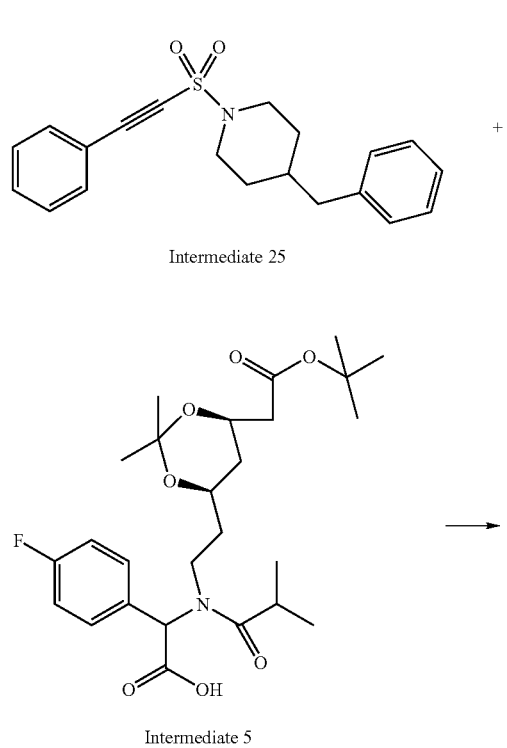

Intermediate 25

Intermediate 5

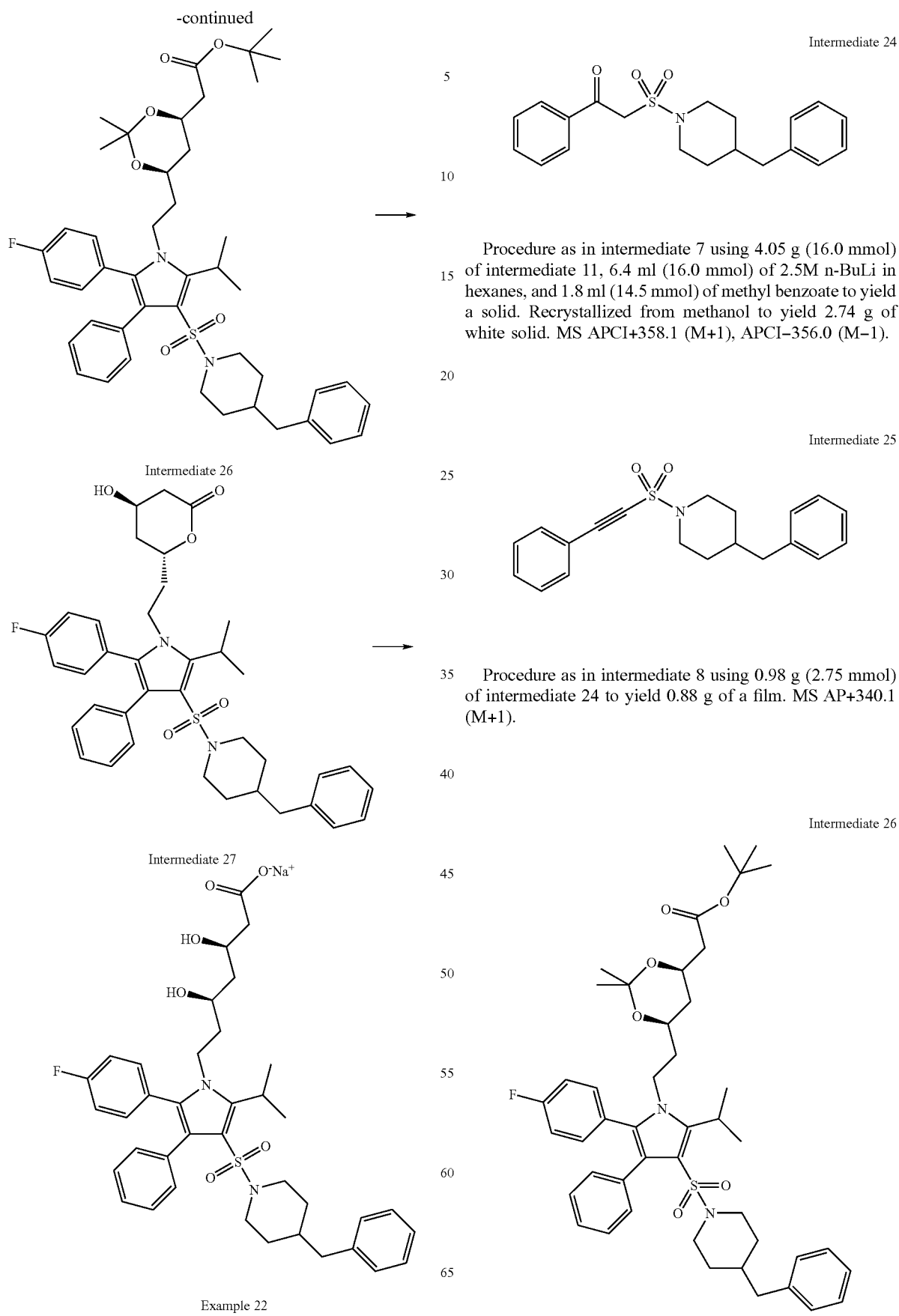
Procedure as in intermediate 7 using 4.05 g (16.0 mmol) of intermediate 11, 6.4 ml (16.0 mmol) of 2.5M n-BuLi in hexanes, and 1.8 ml (14.5 mmol) of methyl benzoate to yield a solid. Recrystallized from methanol to yield 2.74 g of white solid. MS APCI+358.1 (M+1), APCI–356.0 (M–1).
Procedure as in intermediate 8 using 0.98 g (2.75 mmol) of intermediate 24 to yield 0.88 g of a film. MS AP+340.1 (M+1).

Procedure as in intermediate 9 using 0.9 g (1.82 mmol) of intermediate 5 and 0.56 g (1.65 mmol) of intermediate 25. Chromatography gave 0.74 g of a foam. MS APCI+773.2 (M+1).

CHN Calc. for 3.07H₂O: C, 60.52; H, 6.70; N, 3.71. Found: C, 60.13; H, 6.26; N, 3.47.

Scheme 13, below, relates to preparation of Intermediates 28-31 and Example 23.

Intermediate 27

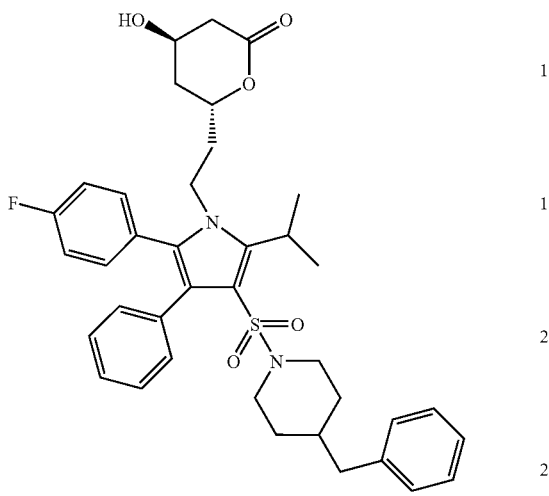

Procedure as in intermediate 10 using 0.38 g (0.49 mmol) of intermediate 26 gave a foam which was isolated by column chromatography using silica gel and a mixture of ethyl acetate/hexanes (gradient of 50% mixture to 75% mixture) to yield 233 mg of a film. MS APCI+659.1 (M+1).

Example 22

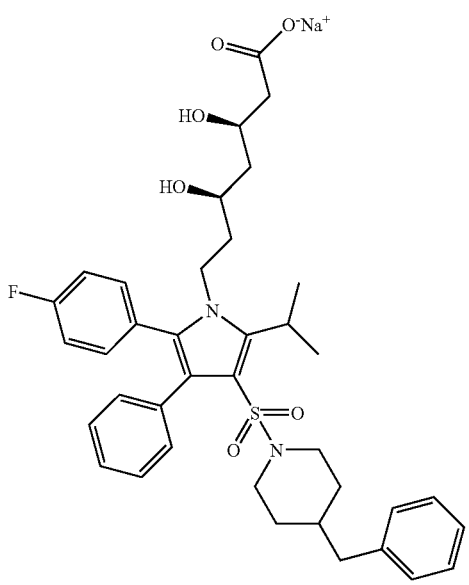

Solution of 0.177 g (0.27 mmol) of intermediate 27 in 6 ml of THF was treated with 230 μL of 1N NaOH and stirred at room temperature for 2 h. Reaction was not complete and was treated with another 45 μL of 1N NaOH and stirred for 1 h. Concentrated, residue taken up in water, frozen, and lyophilized overnight. Collected 0.19 g of white solid. MS (parent) APCI+677.1 (M+1), APCI−675.1 (M−1).

Scheme 13

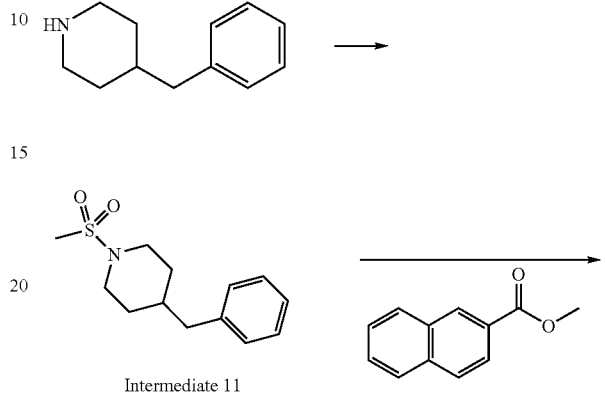

Intermediate 11

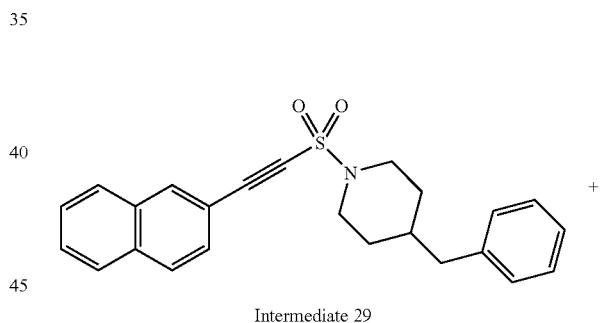

Intermediate 28

Intermediate 29

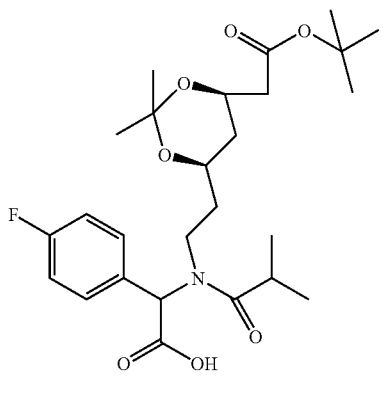

Intermediate 5

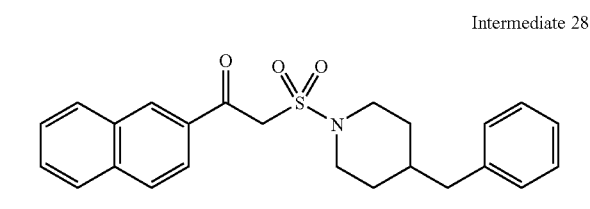
Intermediate 28
Procedure as in intermediate 7 using 4.05 g (16.0 mmol) of intermediate 11, 6.4 ml (16.0 mmol) of 2.5M n-BuLi in hexanes, and 2.78 g (14.5 mmol) of methyl 2-naphthoate to yield a solid. Recrystallized from methanol/ethanol to yield 2.80 g of white solid. MS APCI+408.0 (M+1).
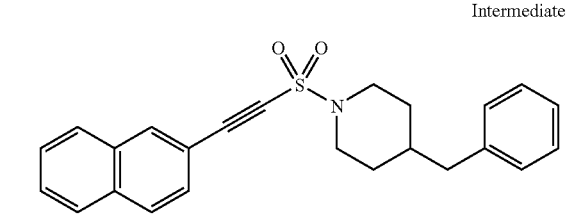
Intermediate 29
Procedure as in intermediate 8 using 1.12 g (2.75 mmol) of intermediate 28 to yield 1.04 g of a film. MS AP+390.1 (M+1).
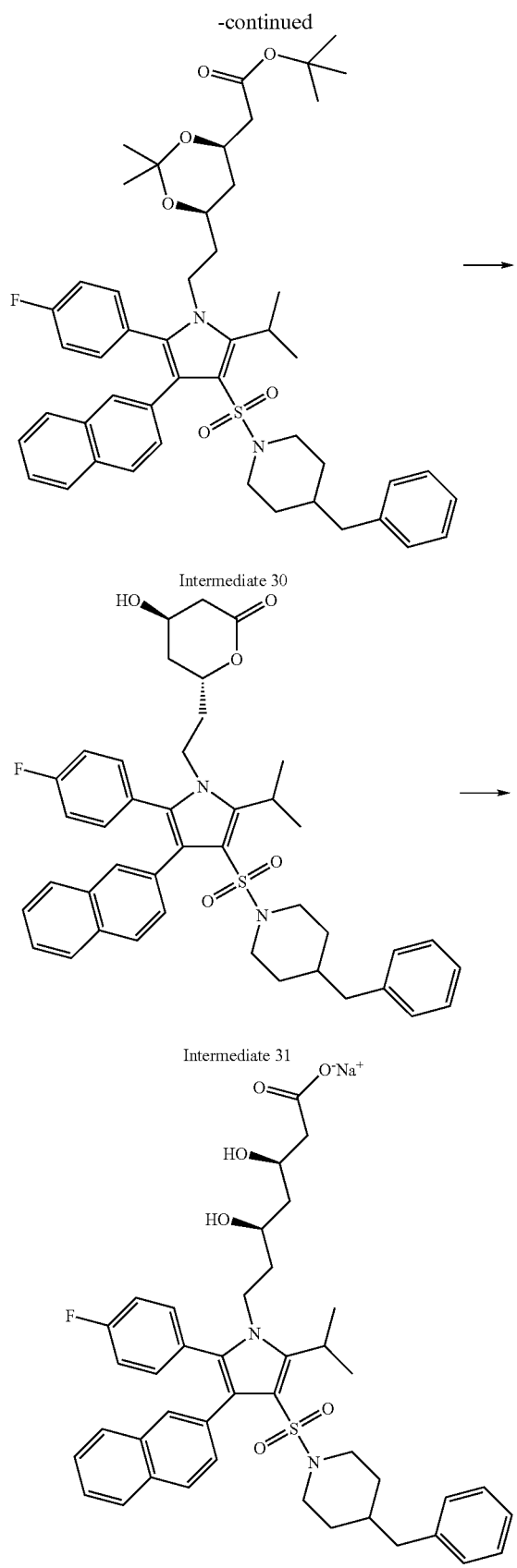
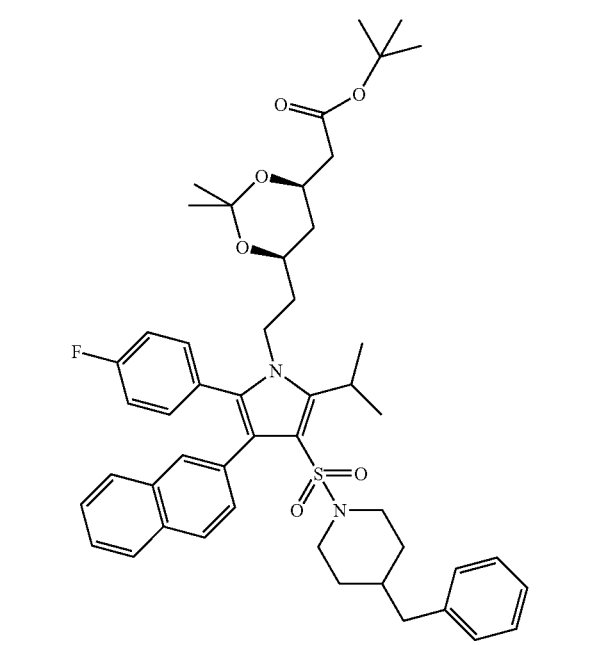
Intermediate 30

Procedure as in intermediate 9 using 0.9 g (1.82 mmol) of intermediate 5 and 0.64 g (1.65 mmol) of intermediate 29. Chromatography gave 0.74 g of a film. MS APCI+823.2 (M+1).

CHN Calc. for 2.97H$_2$O: C, 62.87; H, 6.52; N, 3.49. Found: C, 62.48; H, 6.25; N, 3.19.

Scheme 14, below, relates to preparation of Intermediates 32-35 and Example 24.

Intermediate 31

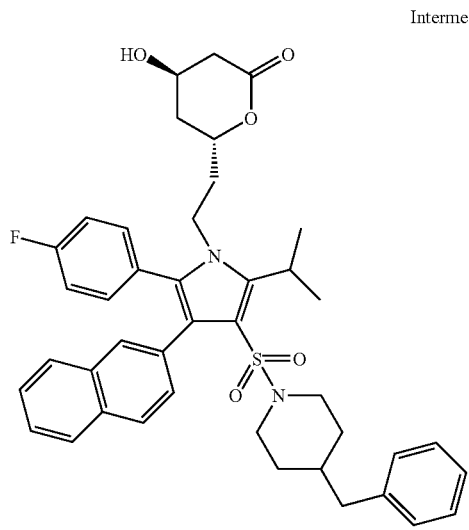

Procedure as in intermediate 10 using 0.47 g (0.57 mmol) of intermediate 30 gave a foam which was isolated by column chromatography using silica gel and a mixture of ethyl acetate/hexanes (50% to 75%) to yield 298 mg of a film. MS APCI+709.1 (M+1).

Example 23

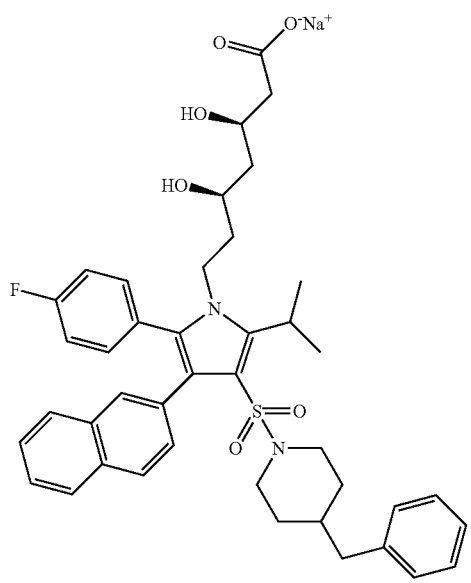

Solution of 0.238 g (0.34 mmol) of intermediate 31 in 8 ml of THF was treated with 290 μL of 1N NaOH and stirred at room temperature for 2 h. Reaction was not complete and was treated with another 25 μL of 1N NaOH and stirred for 1 h. Concentrated, residue taken up in water, frozen, and lyophilized overnight. Collected 0.25 g of white solid. MS (parent) APCI+727.1 (M+1).

Scheme 14

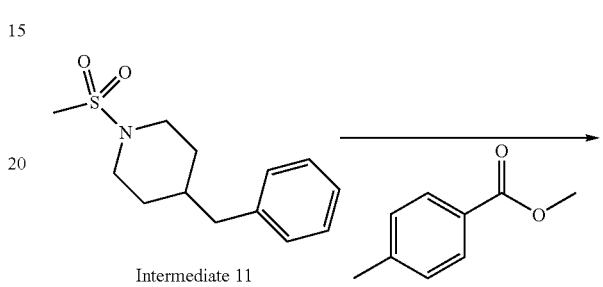

Intermediate 11

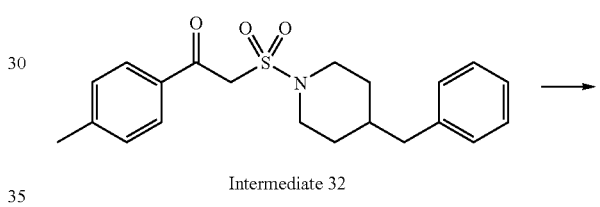

Intermediate 32

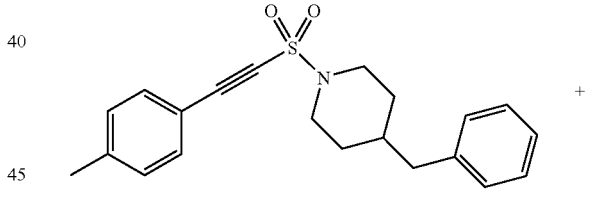

Intermediate 33

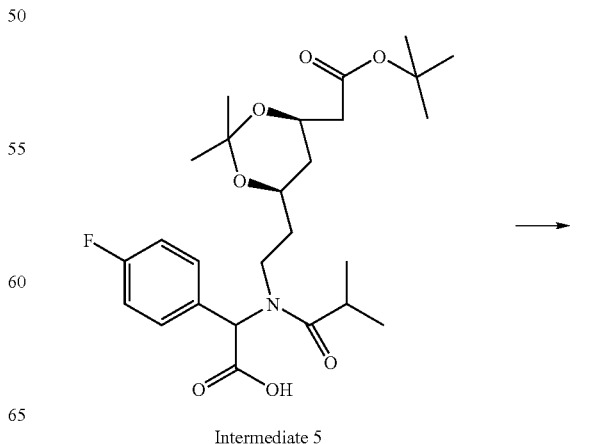

Intermediate 5

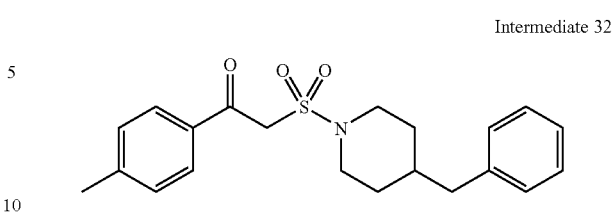

Intermediate 32

Procedure as in intermediate 7 using 4.05 g (16.0 mmol) of intermediate 11, 6.4 ml (16.0 mmol) of 2.5M n-BuLi in hexanes, and 2.20 g (14.5 mmol) of methyl 4-methylbenzoate to yield an oil. Chromatographed on silica gel using ethyl acetate/hexanes (0-35%) to yield 2.27 g of white solid. MS APCI+372.1 (M+1).

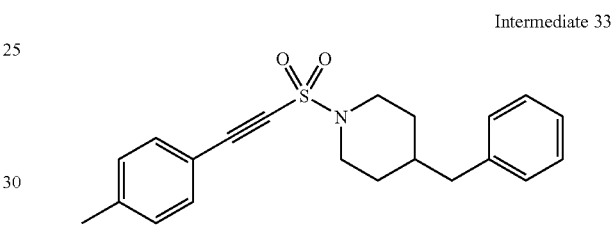

Intermediate 33

Procedure as in intermediate 8 using 1.02 g (2.75 mmol) of intermediate 32 to yield 0.83 g of a film. MS APCI+354.1 (M+1).

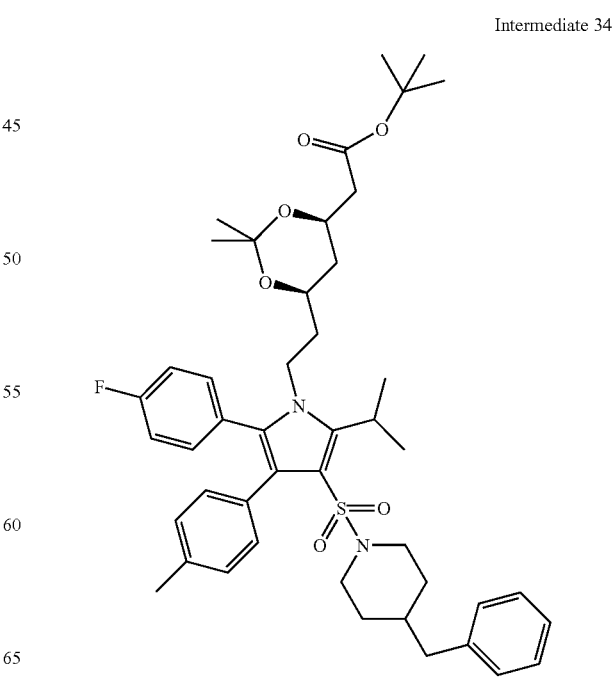

Intermediate 34

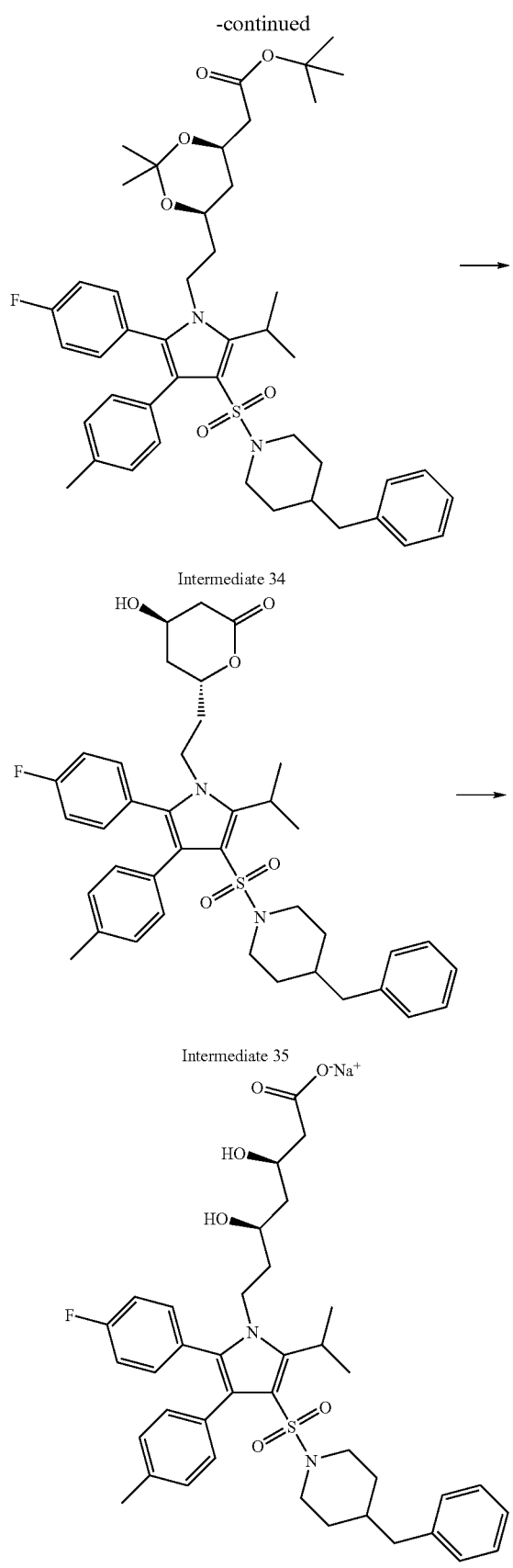

Example 24

Procedure as in intermediate 9 using 0.9 g (1.82 mmol) of intermediate 5 and 0.58 g (1.65 mmol) of intermediate 33. Chromatography gave 0.46 g of a film. MS APCI+787.2 (M+1).

Intermediate 35

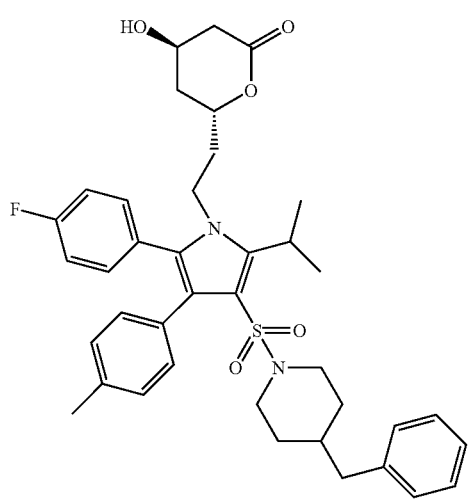

Procedure as in intermediate 10 using 0.44 g (0.56 mmol) of intermediate 34 gave a foam which was isolated by column chromatography using silica gel and a mixture of ethyl acetate/hexanes (gradient of 50% mixture to 75% mixture) to yield 200 mg of a film. MS APCI+673.1 (M+1).

Example 24

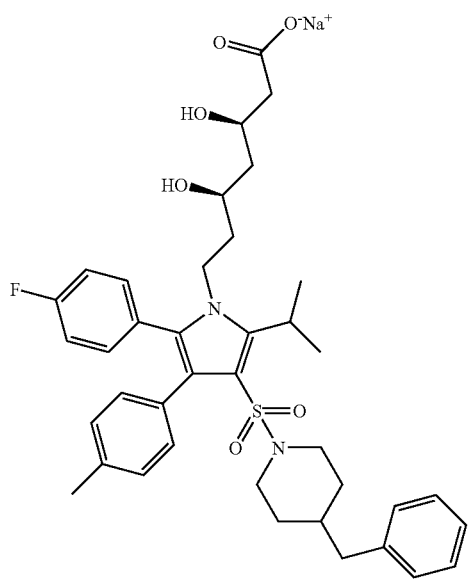

Solution of 0.162 g (0.24 mmol) of intermediate 35 in 5 ml of THF was treated with 230 μL of 1N NaOH and stirred at room temperature for 2 h. Concentrated, residue taken up in water, frozen, and lyophilized overnight. Collected 0.167 g of white solid. MS (parent) APCI+691.1 (M+1), APCI−689.1 (M−1).

CHN Calc. for 2.84H$_2$O: C, 61.31; H, 6.82; N, 3.67.
Found: C, 60.92; H, 6.34; N, 3.37.

Scheme 15, below, relates to preparation of Intermediates 36-39 and Example 25.

Scheme 15

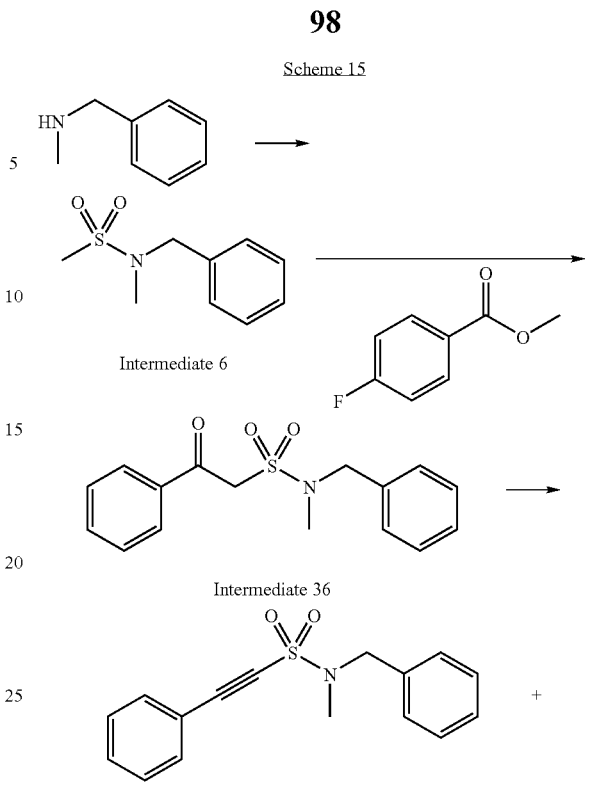

Intermediate 6

Intermediate 36

Intermediate 37

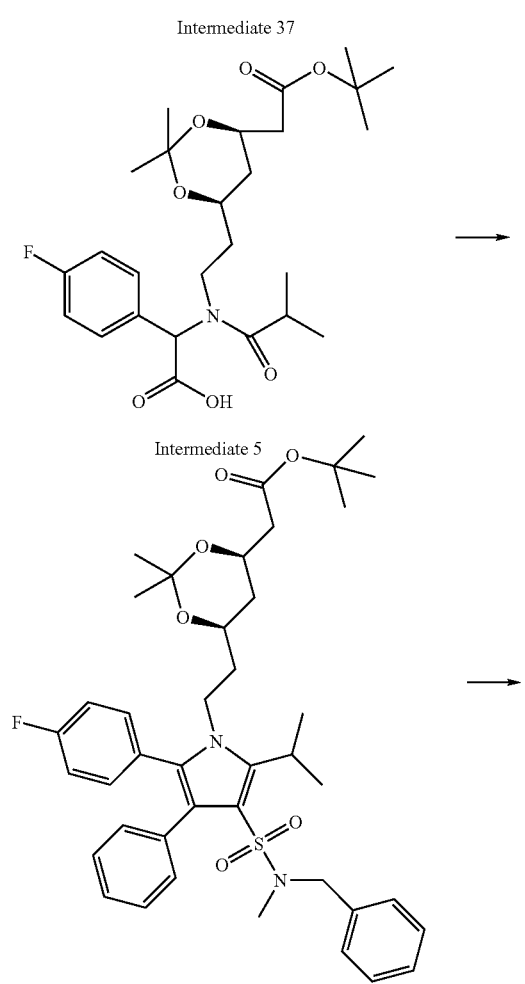

Intermediate 5

Intermediate 38

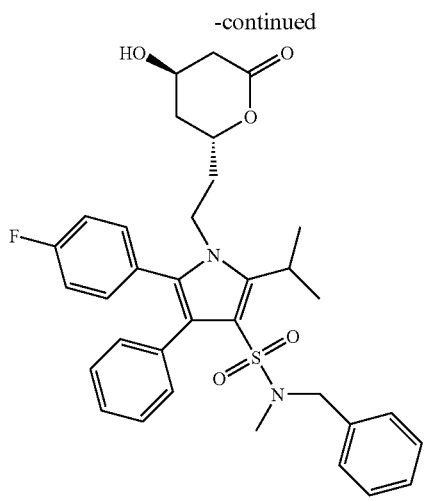

Intermediate 39

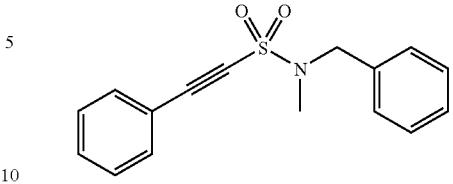

Intermediate 37

Procedure as in intermediate 8 using 0.83 g (2.75 mmol) of intermediate 36 to yield 0.75 g of a film. MS AP+286.0 (M+1).

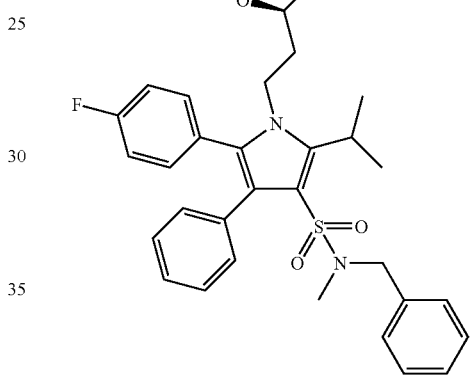

Intermediate 38

Procedure as in intermediate 9 using 0.9 g (1.82 mmol) of intermediate 5 and 0.47 g (1.65 mmol) of intermediate 37. Chromatography gave 0.72 g of a film. MS APCI+719.1 (M+1).

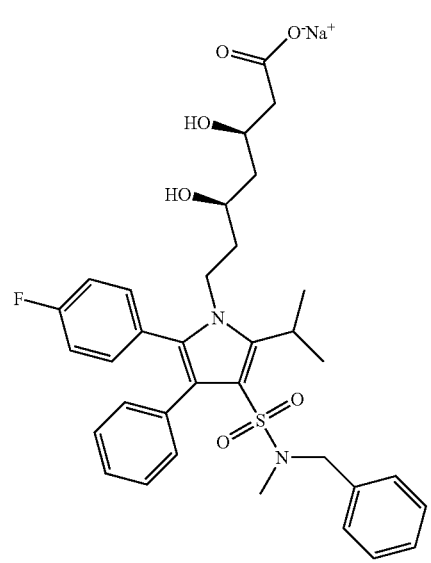

Example 25

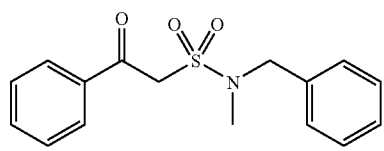

Intermediate 36

Procedure as in intermediate 7 using 3.39 g (17.0 mmol) of intermediate 6, 6.8 ml (17.0 mmol) of 2.5M n-BuLi in hexanes, and 2.02 ml (14.5 mmol) of methyl benzoate to yield an oil. Chromatographed on silica gel using ethyl acetate/hexanes (0-35%) to yield 2.47 g of white solid. MS APCI+304.1 (M+1).

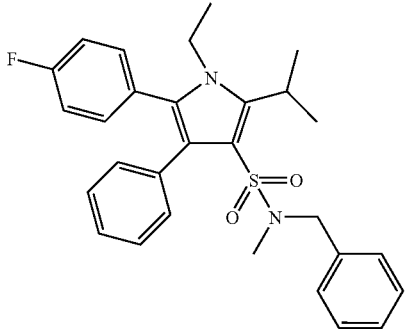

Intermediate 39

0.71 g (0.99 mmol) of intermediate 38 was treated with 20 ml of TFA/DCM (1:9) and stirred at room temperature for 1 h. Concentrated and residue taken up in ethyl acetate and washed with saturated NaHCO₃, and water. Dried organics over sodium sulfate and concentrated to yield a foam which was isolated by column chromatography using silica gel and a mixture of ethyl acetate/hexanes (gradient of 50% mixture to 75% mixture) to yield 0.5 g of a film. MS APCI+605.1 (M+1).

Example 25

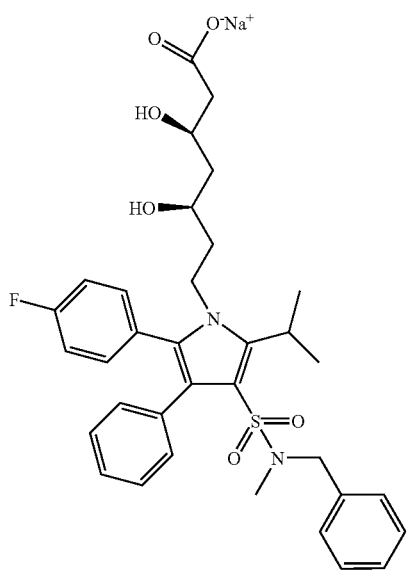

Solution of 0.378 g (0.625 mmol) of intermediate 39 in 13 ml of THF was treated with 540 µL of 1N NaOH and stirred at room temperature for 2 h. Reaction not complete and treated with another 50 µL of 1N NaOH and stirred for 1 h. Concentrated, residue taken up in water, frozen, and lyophilized overnight. Collected 0.414 g of white solid. MS (parent) APCI+623.1 (M+1), APCI−621.1 (M−1).

CHN Calc. for 2.15H₂O: C, 59.75; H, 6.24; N, 4.10 Found: C, 59.36; H, 5.99; N, 3.76.

Example 26

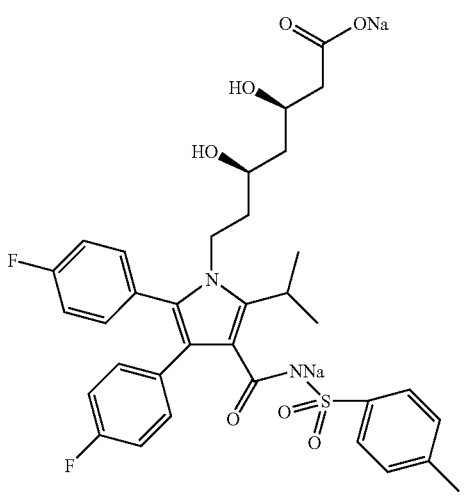

-continued

Step A

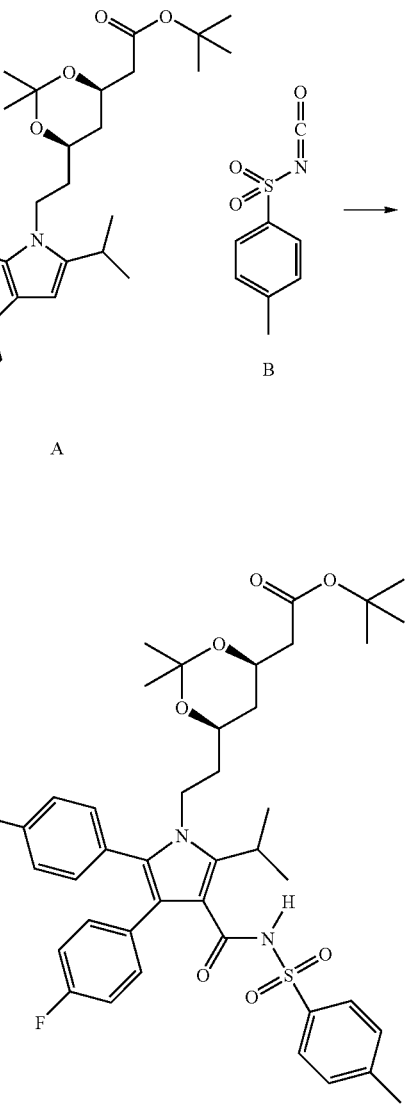

Preparation:

A solution of the above starting material-B in Et₂O (2 mL) was added to a solution of A from Example 1, Step A in Et₂O (3 mL) under N₂ over 2 minutes. The reaction mixture was stirred for another 1 hour, TLC (20% EtOAc in hexanes) indicated that A was not completely consumed. More B was added (2×0.083 mL). After stirring for another 3 hours, the reaction was concentrated in vacuo, and the residue was diluted with EtOAc. The solution was washed with 1 N HCl (2×30 mL) and brine (2×30 mL), and dried over Na₂SO₄. The mixture was filtered and the filtrate was concentrated. A white solid was formed, which was removed via filtration. The filtrate was concentrated, and further purified by chromatography (5-40% EtOAc in hexanes) to give the desired compound as a white foam, 0.1164 g. MS APCI−749.3 (M−H); MP 79-88° C.

Combustion Analysis for [C₄₁H₄₈F₂N₂O₇S.0.1H₂O]:

|        | Carbon | Hydrogen | Nitrogen | F    |
|--------|--------|----------|----------|------|
| Theory | 65.42  | 6.45     | 3.72     | 5.05 |
| Found  | 65.16  | 6.50     | 3.66     | 5.29 |

Step B

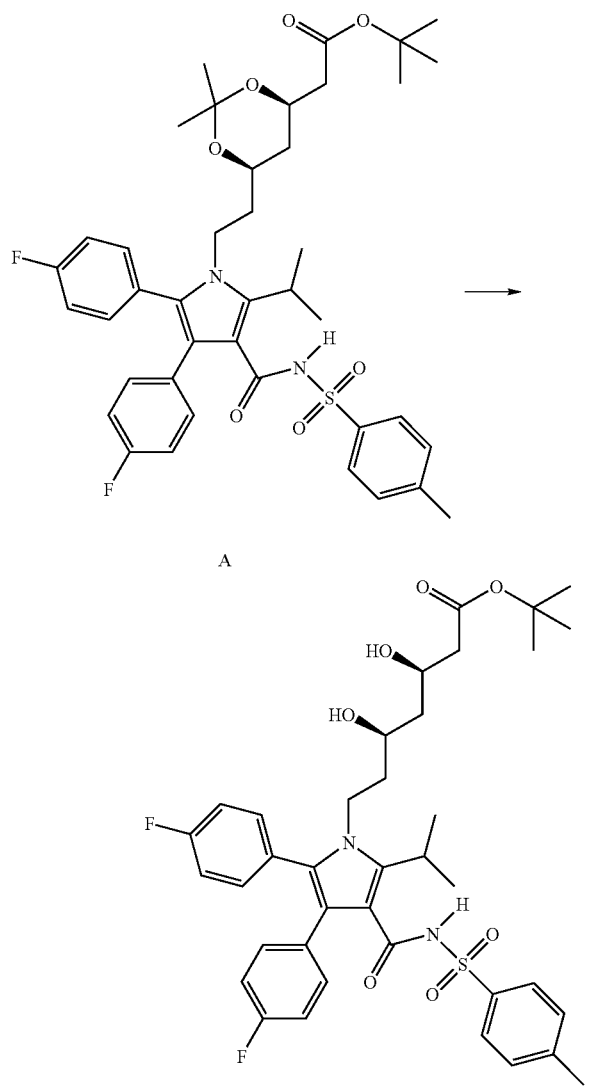

A

B

Preparation:
To a suspension of the above starting material-A from Step A in MeOH (8.88 mL/mmol, 2 mL) was added 1 N HCl (0.100 mL). The resulting mixture was stirred for 5 hours. The reaction mixture was diluted with 30 mL of EtOAc, and then washed with 1 N HCl (2×20 mL) and brine (2×20 mL), dried over Na$_2$SO$_4$. The mixture was filtered and the filtrate was concentrated in vacuo to give an oil, which was further purified by chromatography (10-60% EtOAc in hexanes). The desired product was isolated. (74 mg.) MS (APCI+, 711.2 M+H) MP 80-91° C.
Combustion Analysis for (C$_{38}$H$_4$F$_2$N$_2$O$_7$S):

|        | Carbon | Hydrogen | Nitrogen |
|--------|--------|----------|----------|
| Theory | 64.21  | 6.24     | 3.94     |
| Found  | 63.95  | 6.31     | 3.84     |

Step C

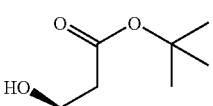

NaOH →

A

B

Preparation:
To a suspension of the above starting material-A from Step B in MeOH (2 mL) was added 1N NaOH. The resulting reaction solution was stirred at RT for 2.5 hours. MS showed that A was consumed and product was formed (655.1, acid+H). The reaction mixture was then concentrated in vacuo. 2 mL of MeOH was added to dissolve the residue and 5 mL of toluene was added, and then evaporated to azeotropically remove water. This process was repeated (twice) until a white solid was obtained. The white solid was dissolved in 4 mL of MeOH, then methylene chloride was added dropwise until a cloudy solution was obtained (the final solution was approximately 15-20% MeOH in methylene chloride). After standing for 0.5 hour, the mixture was filtered to remove the solid (excess of NaOH, the di-sodium salt is soluble in 15% MeOH in methylene chloride). The filtrate was concentrated in vacuo to afford a solid, which was triturated with ether to afford a white precipitate. Filtration gave a white solid, (0.0267 g), desired product. NMR and MS showed the acid-ester peak APCI+ (655.2, acid+H). MP>240° C. (decomposed).

Combustion Analysis for
($C_{34}H_{34}F_2N_2Na_2O_7S.2.25NaOH.2.1H_2O$):

|  | Carbon | Hydrogen | Nitrogen |
|---|---|---|---|
| Theory | 49.41 | 4.93 | 3.39 |
| Found | 49.27 | 4.54 | 2.99 |

Example 27

Step A

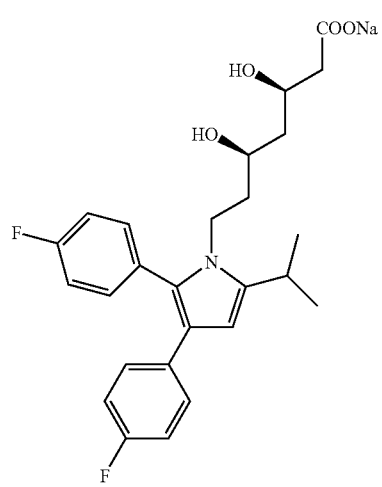

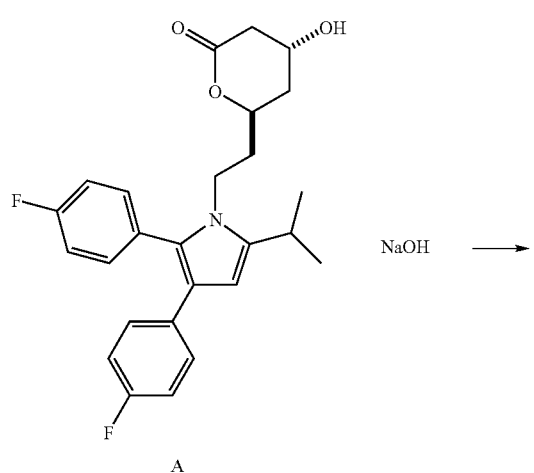

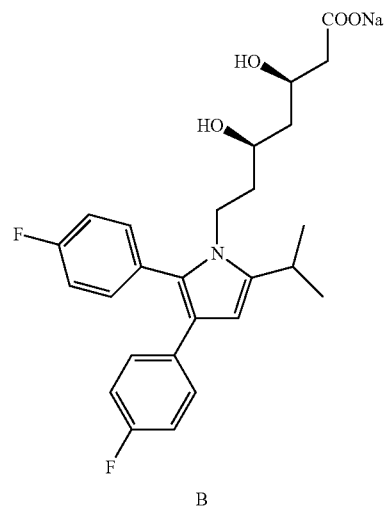

Preparation:

To a solution of the above starting material-A from Example 1, Step E in MeOH (20 mL) and THF (15 mL) was added 1N NaOH (2.9 mL). The resulting reaction solution was stirred at RT for 2 hours, and then concentrated in vacuo. 5 mL of MeOH was added to dissolve the residue and 20 mL of toluene was added, and then evaporated to azeotropically remove water. This process was repeated (twice) until a white solid was obtained. The white solid was dissolved in 10 mL of MeOH, then diluted with 40 mL of methylene chloride. A cloudy solution was obtained. After standing for 0.5 hour, the mixture was filtered to remove the solid (excess of NaOH, the sodium salt is soluble in 20% MeOH in methylene chloride), the filtrate was concentrated in vacuo to afford a solid, which was triturated with ether to afford a white precipitate. Filtration gave a white solid. The solid was dissolved in 2 mL of MeOH again, and then diluted with 28 mL of dichloromethane (6% MeOH in dichloromethane solution). The solution became cloudy and was allowed to stand at RT for 10 minutes, then filtered. The filtrate was concentrated in vacuo to give a solid which was triturated with ether. A yellow gel was obtained. Ether was stripped off and a yellow foam was obtained. (0.31 g, desired product) NMR (product+$H_2O$+$Et_2O$) and MS showed the acid peak APCI+ (458, acid+H). MP 215-220° C. (decomposed).

Combustion Analysis for ($C_{32}H_{33}F_2N_2NaO_6S.C_4H_{10}O.1.5H_2O$):

|  | Carbon | Hydrogen | Nitrogen | F |
|---|---|---|---|---|
| Theory | 63.34 | 6.57 | 2.64 | 7.16 |
| Found | 63.13 | 6.48 | 2.52 | 7.33 |

Example 28
(3R,5R)-7-[2,3-Bis-(4-fluoro-phenyl)-5-isopropyl-4-(4-sulfamoyl-phenylsulfamoyl)-pyrrol-1-yl]-3,5-dihydroxy-heptanoic acid disodium salt

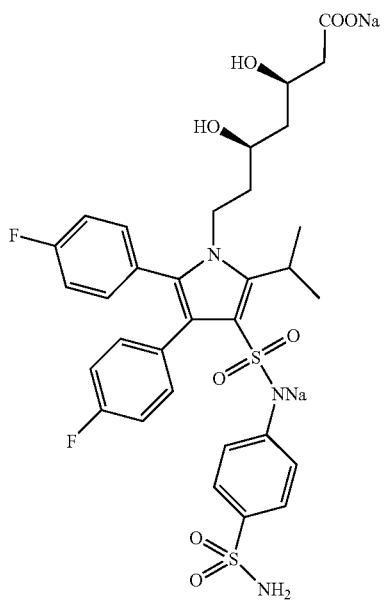

Step A

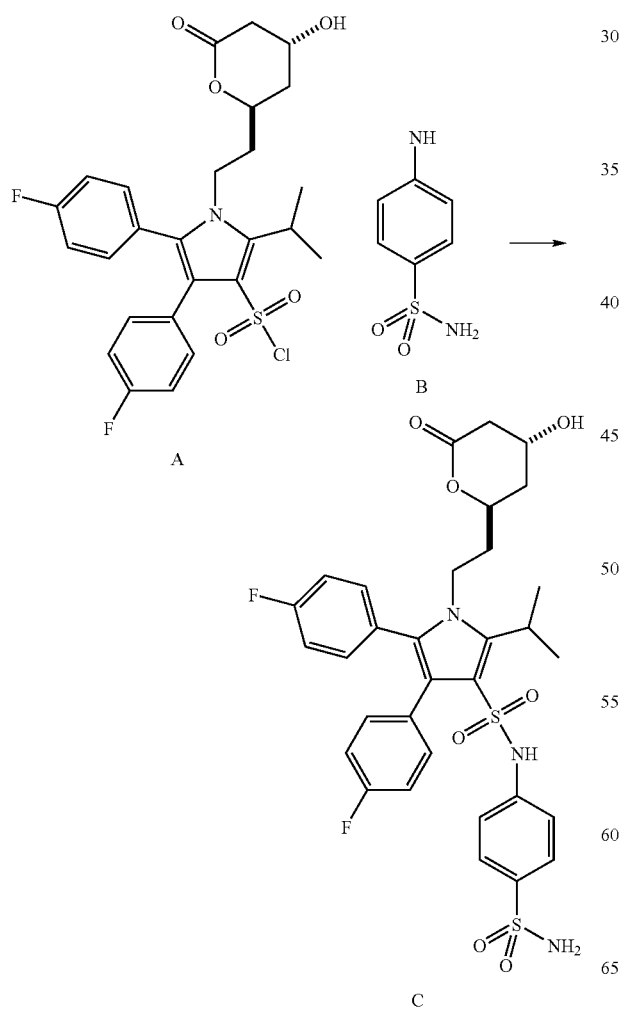

Preparation:

To a solution of the above starting material A from Example 1, Step D in DMF (4.0 mL) was added sulfanilamide. The reaction mixture was stirred at RT under nitrogen for 3.5 hours. The reaction mixture was diluted with 50 mL of ethyl acetate and then washed with 1 N HCl (3×30 mL) and brine, and dried over $Na_2SO_4$. The mixture was filtered and the filtrate was concentrated. The crude product was purified by chromatography and the desired product was isolated as a beige foam, (0.1615 g). MS APCI+674.1 (M+H), MP, 111-115° C.

Combustion Analysis for $[C_{32}H_{33}F_2N_3O_7S_2.1.0C_4H_8O_2$ (ethyl acetate)]:

|  | Carbon | Hydrogen | Nitrogen |
|---|---|---|---|
| Theory | 56.75 | 5.42 | 5.52 |
| Found | 56.38 | 5.09 | 5.50 |

Step B

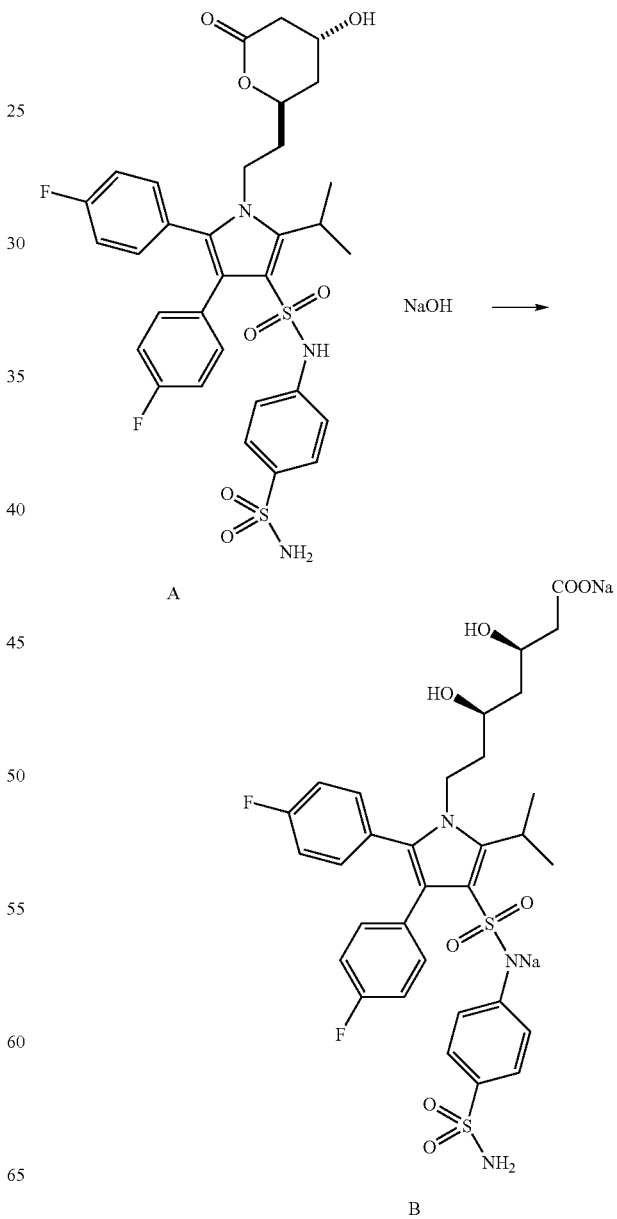

Preparation:

To a solution of the above starting material-A from Step A in MeOH (2 mL) was added 1N NaOH. The resulting reaction solution was stirred at RT for 2.0 hours. MS showed peak 692.2 (acid+H). The reaction mixture was then concentrated in vacuo. 2 m/L of MeOH was added to dissolve the residue and 5 mL of toluene was added, and then evaporated to azeotropically remove water. This process was repeated (twice) until a white solid was obtained. The white solid was dissolved in 4 mL of MeOH, then diluted with 16 mL of methylene chloride (overall solution would be 20% MeOH in methylene chloride). A cloudy solution was obtained. After standing for 0.5 hour, the mixture was filtered to remove the solid (excess of NaOH, the sodium salt is soluble in 20% MeOH in methylene chloride), the filtrate was concentrated in vacuo to afford a solid, which was triturated with ether to get a white solid. Filtration gave a white solid, (0.1248 g, desired product). NMR and MS showed the acid peak APCI+ (692.3, acid+H). MP 205-207° C. (decomposed).

Combustion Analysis for $(C_{32}H_{33}F_2N_3Na_2O_8S_2 \cdot 2.5H_2O)$:

|  | Carbon | Hydrogen | Nitrogen |
|---|---|---|---|
| Theory | 49.23 | 4.91 | 5.38 |
| Found | 49.45 | 4.75 | 5.00 |

Example 29

3,5-Dihydroxy-4-[3-(1H-imidazol-4-yl)-2-(3-naphthalen-1-yl-2-naphthalen-1-ylmethyl-propionylamino)-propionylamino]-pentanoic acid (1-benzyl-carbamoyl-3-methyl-butyl)-amide disodium salt

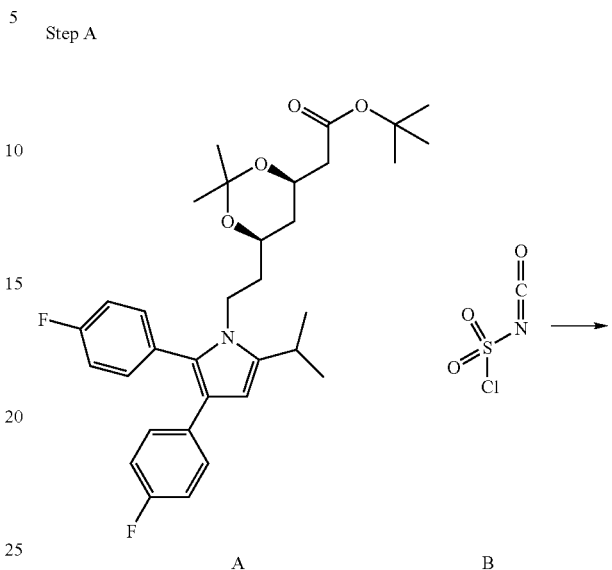

Step A

Preparation:

A solution of the above starting material-B in Et₂O (5 mL) was added to a solution of starting material A from Example 1, Step A in Et₂O (5 mL) under N₂ over 5 minutes. The reaction mixture was stirred for another 10 minutes, concentrated in vacuo. A yellow foam was obtained. The crude product was used in the next step without further purifications.

Step B

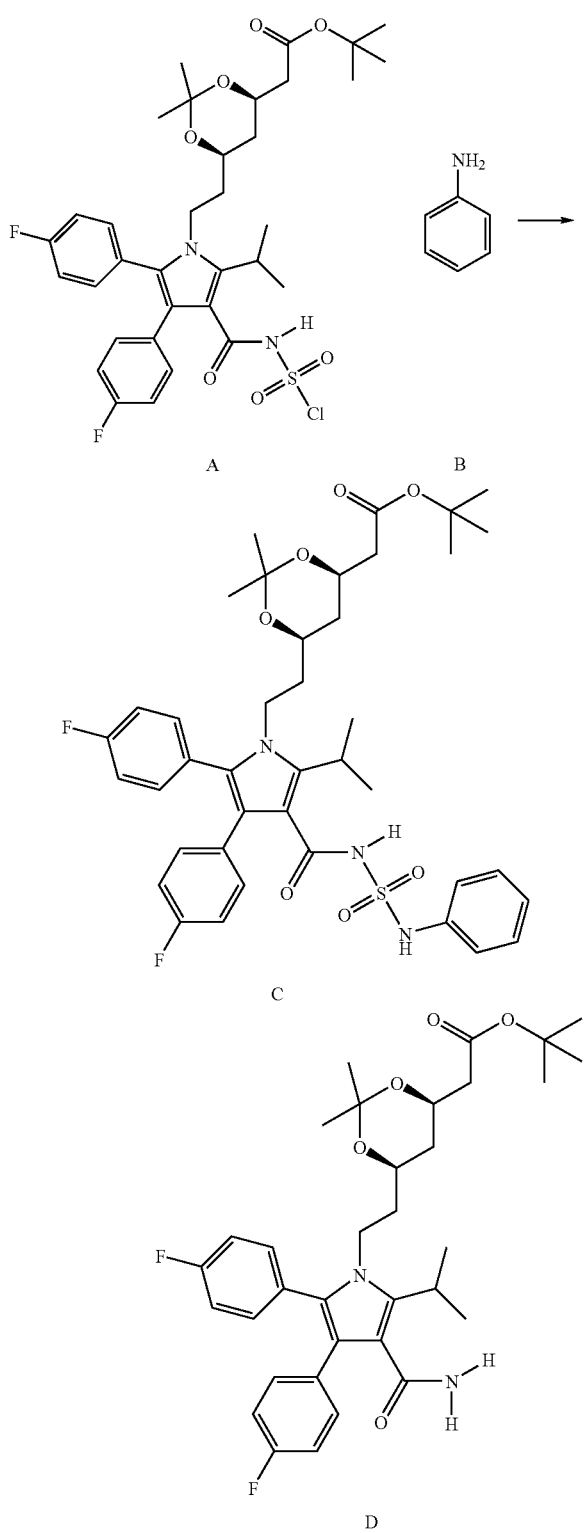

in vacuo. The crude product was purified by chromatography (5-50% EtOAc in hexanes). The desired product was isolated as a yellow foam and characterized by NMR and MS. (0.37 g, 71% over two steps) MP 79-85° C.; MS, APCI-750.4 (M-H).

Combustion Analysis for [C40H47F2N3O7S.0.2H2O]:

|  | Carbon | Hydrogen | Nitrogen | F |
|---|---|---|---|---|
| Theory | 63.59 | 6.32 | 5.56 | 5.03 |
| Found | 63.25 | 6.53 | 5.21 | 4.99 |

Step C

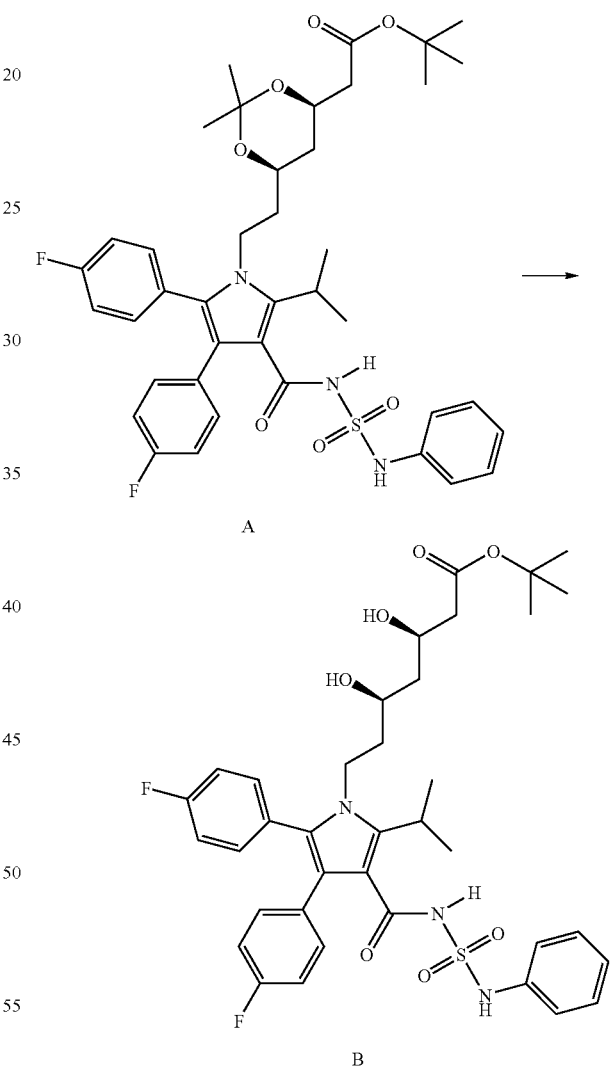

Preparation:

To a solution of the above starting material-A from Step A in THF (5 mL) was added aniline (0.189 mL) under N₂. White precipitate formed instantly. The reaction mixture was stirred for another 16 hours. The reaction mixture was diluted with EtOAc, washed with 1 N HCl (2×30 mL), and brine, and dried over Na₂SO₄. The mixture was concentrated Preparation:

To a suspension of the above starting material-A from Step B in MeOH (8.88 mL/mmol, 4 mL) was added 1 N HCl (0.1517 mL). The resulting mixture was stirred for 6 hours. The reaction mixture was diluted with 30 mL of EtOAc, washed with 1 N HCl (2×20 mL) and brine (2×20 mL), and dried over Na₂SO₄. The mixture was filtered and the filtrate was concentrated in vacuo to afford a white foam. Fairly pure desired product B based NMR and MS. (1229 g.) was used in the next step without further purifications.

Step D

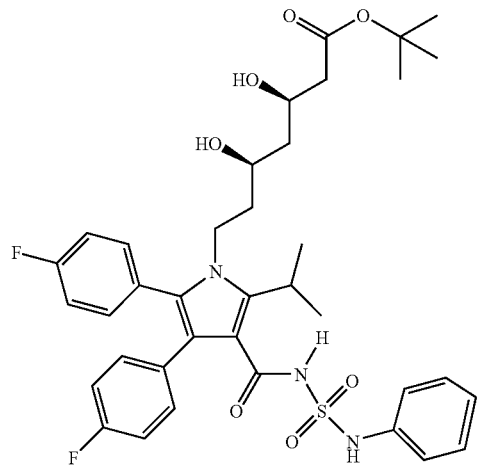

A

B

Preparation:

To a solution of the above starting material-A from Step C in MeOH (8.88 mL/mmol, 4 mL) was added 1 N NaOH (0.3596 mL). The resulting mixture was stirred for 6 hours. The reaction mixture was diluted with 30 mL of EtOAc, washed with 1 N HCl (2×20 mL) and brine (2×20 mL), and dried over $Na_2SO_4$. The mixture was filtered and the filtrate was concentrated in vacuo. The residue was purified by chromatography (10-30% MeOH in DCM). The compound with an Rf value of 0.1 was isolated as a white solid, (41.1 mg).

Step E

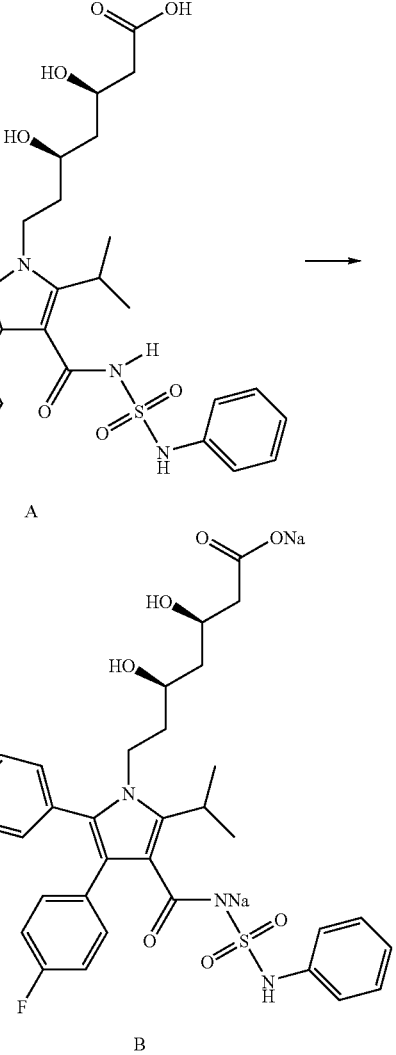

A

B

Preparation:

To a solution of the above starting material-A from Step D in MeOH (3 mL) was added 1 N NaOH (0.1254 mL). The resulting mixture was stirred for 10 minutes. The reaction mixture was concentrated in vacuo. The residue was mixed with toluene and concentrated. The residue was mixed with 5 mL of MeOH and filtered to remove insoluble material. The filtrate was concentrated, and triturated with $Et_2O$ to afford a white solid which was isolated. (43.3 mg. desired product) MS APCI+656.1 (M+H for the parent). MP>240° C.

Combustion Analysis for $[C_{33}H_{33}F_2N_3Na_2O_7S.0.10C_4H_8O_2$ (ethyl acetate). $0.30H_2O.1.85NaOH]$:

|  | Carbon | Hydrogen | Nitrogen |
|---|---|---|---|
| Theory | 51.63 | 5.07 | 5.10 |
| Found | 51.38 | 4.69 | 4.71 |

Example 30

(3R,5R)-7-[3-Carbamoyl-4,5-bis-(4-fluoro-phenyl)-2-isopropyl-pyrrol-1-yl]-3,5-dihydroxy-heptanoic acid monosodium salt

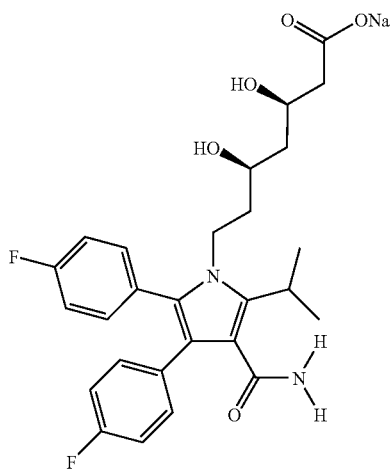

Preparation:

A solution of the above starting material-B in THF (5 mL) was added to a solution of the above starting material-A from Example 29, Step A, in THF (5 mL) under $N_2$ over 1 minute. White precipitate formed instantly. The reaction mixture was stirred for another 15 minutes. The reaction mixture was diluted with EtOAc, washed with 1 N HCl (2×30 mL), and brine, and dried over $Na_2SO_4$. The mixture was filtered and the filtrate was concentrated in vacuo. The crude product was purified by chromatography (10-50% EtOAc in hexanes) to give the desired product. The product was purified again (10-50% EtOAc in hexanes) to give 170 mg. pure product D based on MS and NMR. MP: 76-84° C.; MS, APCI+597.2 (M+H).

Combustion Analysis for $[C_{34}H_{42}F_2N_2O_5 \cdot 1.0\ H_2O]$:

|        | Carbon | Hydrogen | Nitrogen | F    |
|--------|--------|----------|----------|------|
| Theory | 66.43  | 7.21     | 4.56     | 6.18 |
| Found  | 66.61  | 7.07     | 4.58     | 6.15 |

Step A

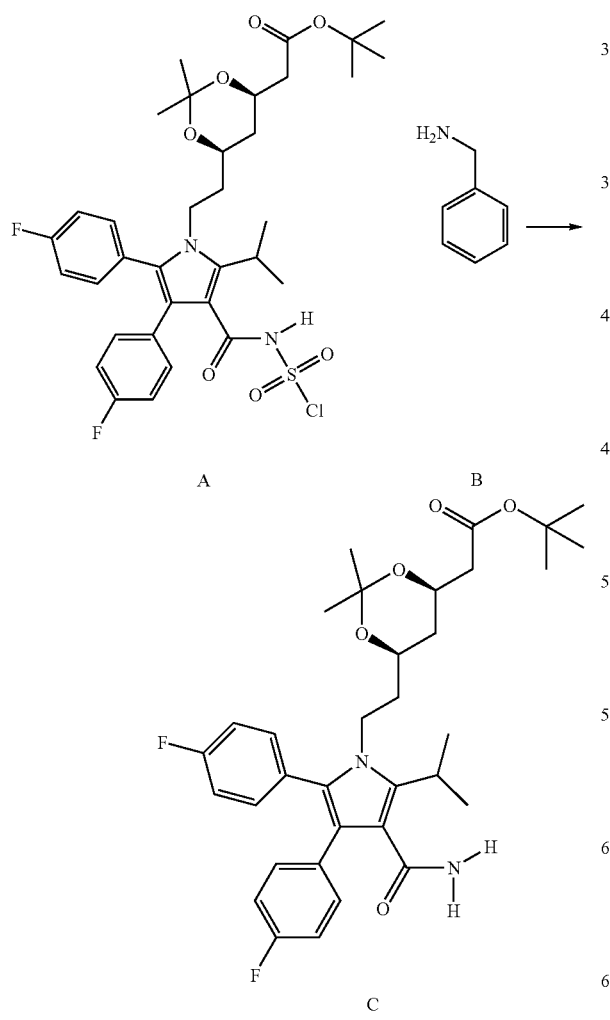

Step B

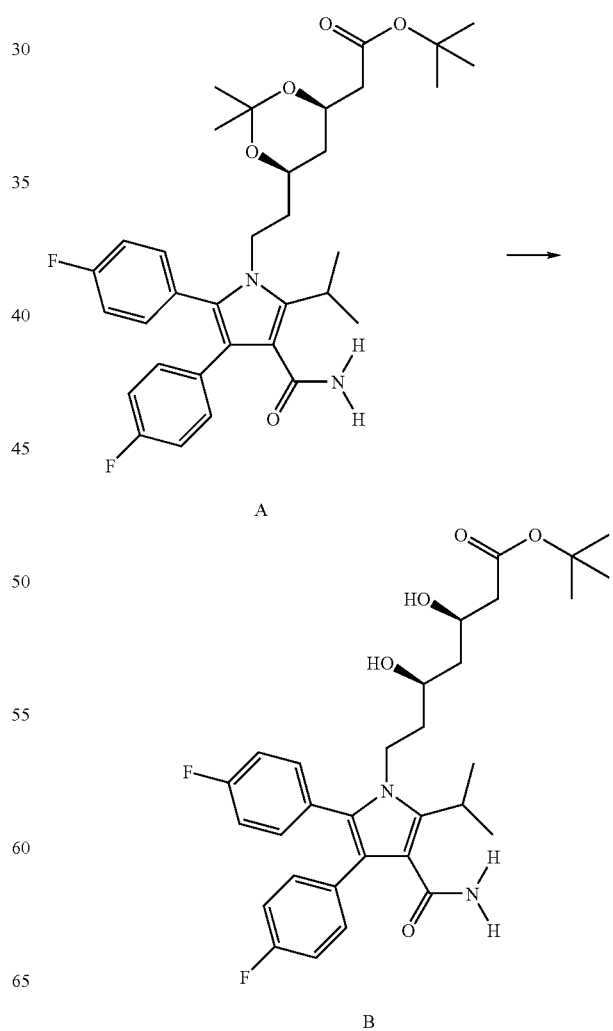

Preparation:

To a suspension of the above starting material-A from Step A in MeOH (8.88 mL/mmol, 2 mL) was added 1 N HCl (0.133 mL). The resulting mixture was stirred for 5 hours. The reaction mixture was diluted with 30 mL of EtOAc, washed with 1 N HCl (2×20 mL) and brine (2×20 mL), and dried over $Na_2SO_4$. The mixture was filtered and the filtrate was concentrated in vacuo to afford a white foam pure desired product (0.077 g.) based NMR and MS (APCI+, 557.2 M+H).

MP 73-78° C.

Combustion Analysis for ($C_{31}H_{38}F_2N_2O_5$):

|  | Carbon | Hydrogen | Nitrogen |
|---|---|---|---|
| Theory | 66.89 | 6.88 | 5.03 |
| Found | 66.62 | 7.03 | 4.86 |

Preparation:

To a suspension of the above starting material-A from Step B in MeOH (2 mL) was added 1N NaOH. The resulting reaction solution was stirred at RT for 2 hours. MS showed that A was consumed and product was formed (501.2, acid+H). The reaction mixture was then concentrated in vacuo. 2 mL of MeOH was added to dissolve the residue and 5 mL of toluene was added, and then evaporated to azeotropically remove water. This process was repeated (twice) until a white solid was obtained. The white solid was dissolved in 0.5 mL of MeOH, then diluted with 9.5 mL of methylene chloride (overall solution would be 5% MeOH in methylene chloride). A cloudy solution was obtained. After standing for 0.5 hour, the mixture was filtered to remove the solid (excess of NaOH, the sodium salt is soluble in 5% MeOH in methylene chloride). The filtrate was concentrated in vacuo to afford a solid, which was triturated with ether to afford a white precipitate. Filtration gave a white solid, 0.0303 g, desired product based on NMR. MS showed the acid-ester peak APCI+ (501.2, acid+H). MP 195-198° C. (decomposed).

Combustion Analysis for ($C_{27}H_{29}F_2N_2NaO_5 \cdot 0.3NaOH \cdot 2.40H_2O$):

|  | Carbon | Hydrogen | Nitrogen |
|---|---|---|---|
| Theory | 56.13 | 5.95 | 4.85 |
| Found | 56.22 | 5.56 | 4.46 |

Step C

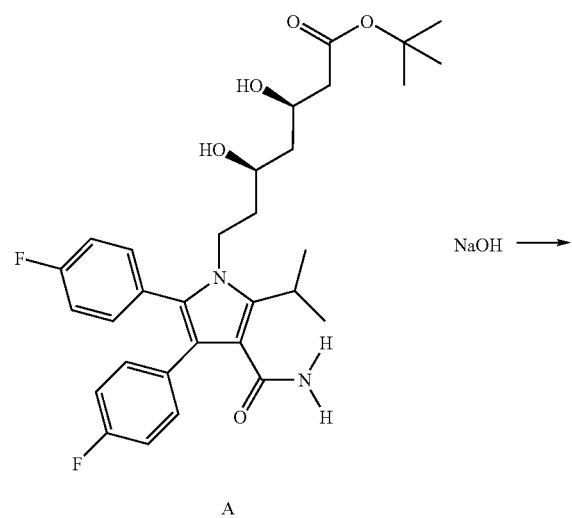

Example 31

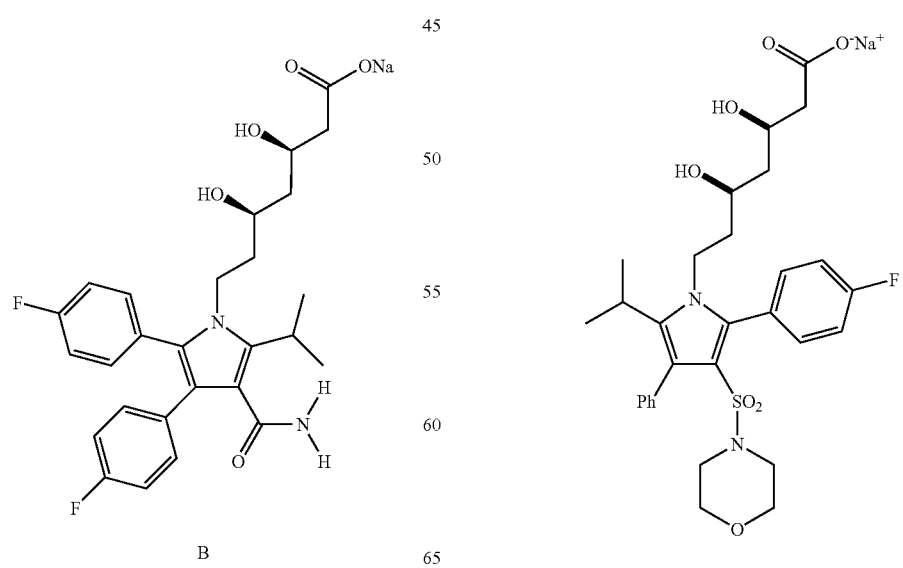

Step A

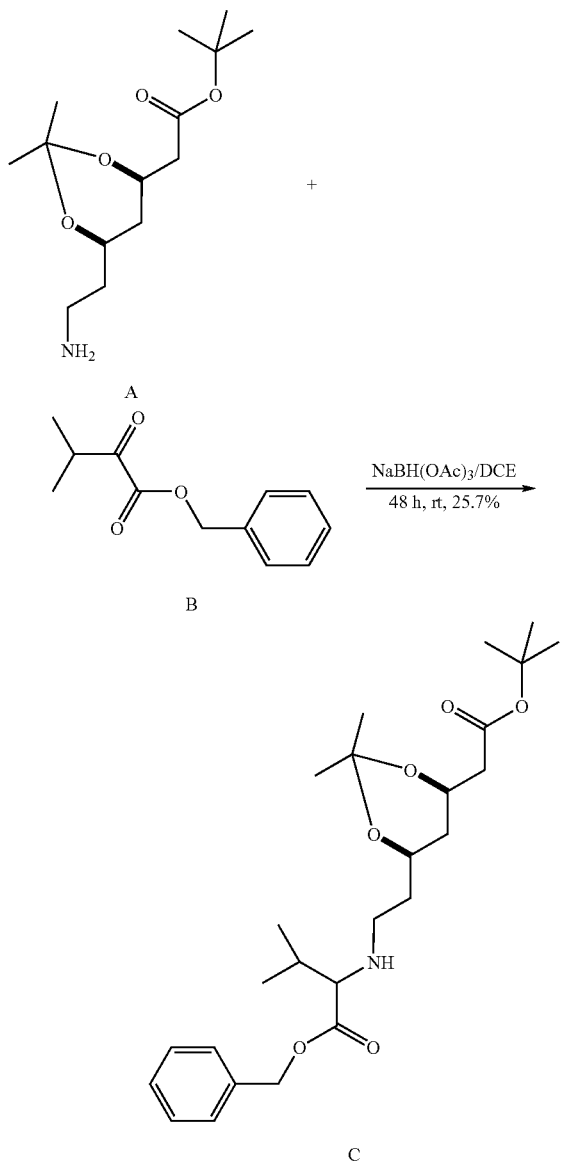

The chiral amine, starting material A, and the α-ketoester, starting material B, were combined in 150 ml of DCE. After stirring @ RT for 1 h, solid sodium triacetoxyborohydride ("NaBH(OAc)₃") was added and the resulting mixture was allowed to stir @ RT for 48 h. The reaction mixture was quenched with sat. aqueous NH₄Cl (10 mL) and water (200 mL). The aqueous layer was adjusted to pH>10 with KOH. The organic layer was diluted with dichloromethane, removed, washed with brine, dried (Na₂SO₄), and concentrated to a crude yellow oil. TLC indicates several major components including starting amine and starting ketone as well as the desired product [R$_f$=0.48, Hexanes/ethyl acetate (1:1), KmnO₄)], and reduced ketoester [R$_f$=0.67, Hexanes/ethyl acetate (1:1), KmnO₄)]

This material was purified by silica gel chromatography eluting with a gradient of hexanes/ethyl acetate mixture [Hexanes/ethyl acetate (95:5 to 70:30)] to give 3.85 g of the desired product, C, as a light oil.

Loop LC-MS [M+H]⁺=464

¹H NMR is consistent with expected product that appears to be contaminated with benzyl alcohol~1 equiv The resulting material, C will be used in next reaction without additional purification.

Step B

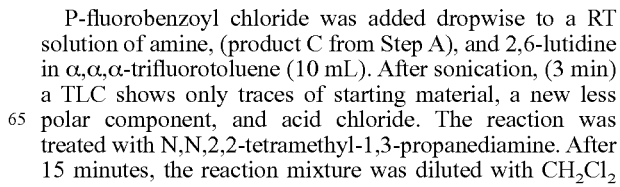

P-fluorobenzoyl chloride was added dropwise to a RT solution of amine, (product C from Step A), and 2,6-lutidine in α,α,α-trifluorotoluene (10 mL). After sonication, (3 min) a TLC shows only traces of starting material, a new less polar component, and acid chloride. The reaction was treated with N,N,2,2-tetramethyl-1,3-propanediamine. After 15 minutes, the reaction mixture was diluted with CH₂Cl₂

(10 mL), and washed sequentially with dilute HCl (pH<1), 1 N NaHCO₃, and brine. The organic layer was dried (Na₂SO4), and concentrated to an oil.

TLC indicates baseline material and one major component: [Hexanes/Ethyl Acetate (3:1; $R_f$=0.27; UV, KMnO₄)].

Purification by flash SiO₂-gel chromatography [Hexanes/Ethyl Acetate 90:10 to 50:50] provides product as a transparent solid.

LC-MS [M+H]⁺=586, (base peak=528).

Hydrogenation

The benzyl ester was submitted to High Pressure Lab for hydrogenation

The returned sample was concentrated and dried under high vacuum to give a colorless solid.

Loop LC-MS [M–H]⁻=494

¹H MNR (CD₃CN) appears to be consistent with the desired product.

The resulting material, C, is used in the subsequent reaction without additional purification.

Step C

To a toluene solution (10 mL) containing the Munchnone precursor (176 mg, 0.355 mmole), (compound C from Step B), and starting material B (89.3 mg, 0.355 mmole), was added acetic anhydride (200 uL). The reaction mixture was then heated to 60° C. for 3 h. The reaction mixture was cooled and evaporated under reduced pressure to give a pale-yellow syrup. Using a silica plug, most of the polar contaminants were removed by using 30% EtOAc in hexane as eluent. Liquid Chromatography coupled with mass spectrometer, ("LCMS") results showed the presence of both regioisomers: Sought 684.2, observed 685.2. Retention time at 2.872 minutes and 3.040 minutes was 8% and 33%, respectively (%=UV ratio at 214 nm). The peak with the retention time of 3.040 min. was identified as desired compound C. ¹H NMR structure confirmed.

Step D

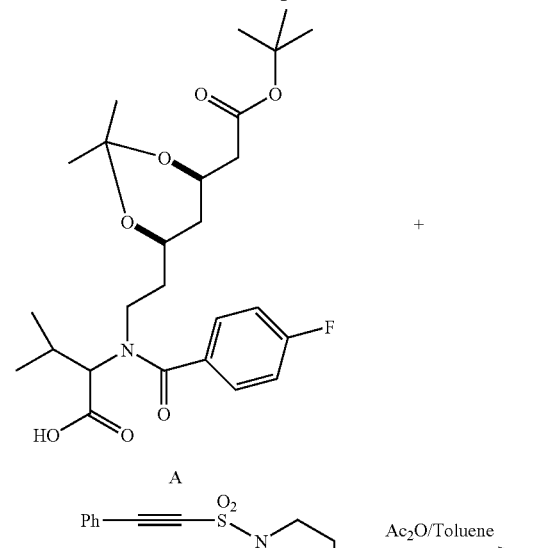

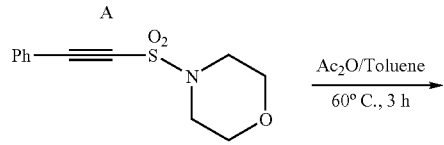

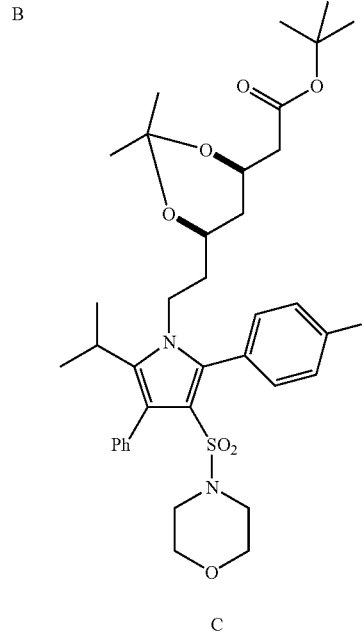

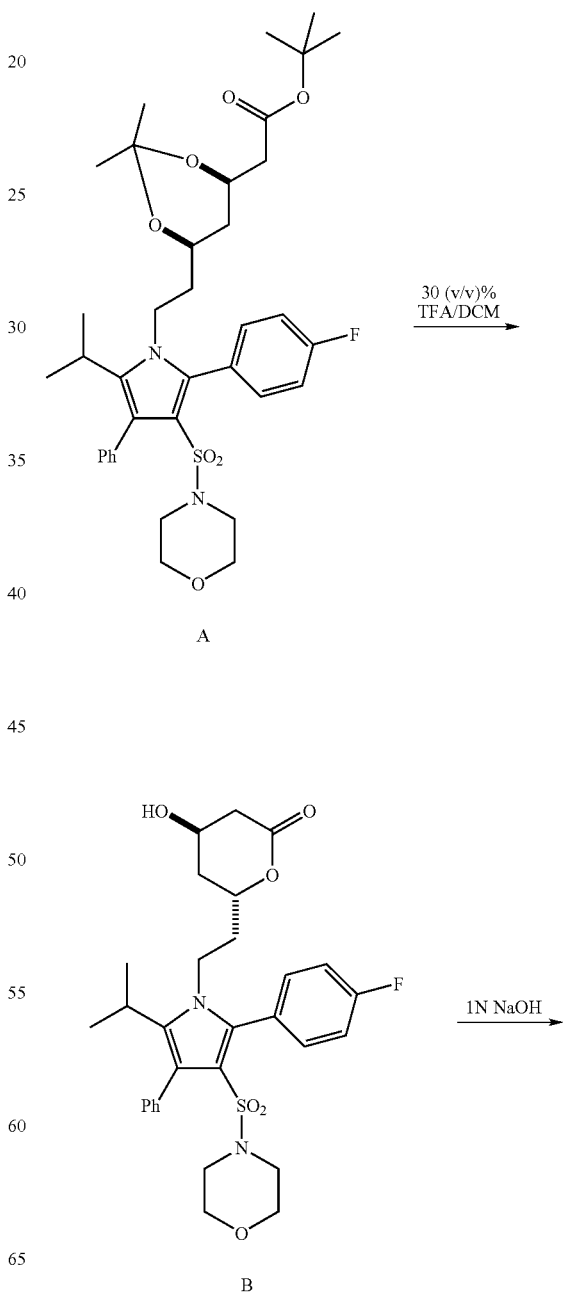

123
-continued

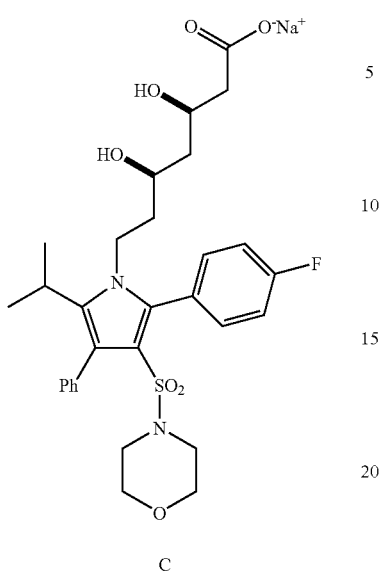

C

To a DCM solution (10 mL) containing compound C from Step C (125 mg, 0.5025 mmole) was added TFA (2.5 mL) at 0° C. The ice-bath was removed after the reaction mixture was well mixed. After 3 h, the reaction was complete. The resultant solution was evaporated under reduced pressure to give a pale yellow amorphous material. Work-up: The amorphous material was dissolved in 25 mL of DCM and treated with 5 mL of 1N NaHCO$_3$ solution followed by washing with water (2 mL). The organic layer was then dried over MgSO$_4$ and filtered. The filtrate was evaporated under reduced pressure to give a pale-yellow amorphous material from which the desired material was isolated by column chromatography (50% EtOAc in hexane). Isolated yield of desired lactone compound B: 94.4 mg, 90.27%: LCMS result (retention time: 2.065 min (1:1 ACN:H$_2$O), surface area=100% at 214 nm; Sought 570, observed M+H=571);

$^1$H NMR structure confirmed.

The lactone B was dissolved in THF (5 mL), and to this solution was added 1 N NaOH solution (450 uM). After 2 h, most of the lactone disappeared to give a baseline spot in TLC. The additional NaOH solution (20 uL) was added dropwise. The solution was stirred for an additional 1 h, and was evaporated under reduced pressure. The resultant solid was then re-dissolved in water and frozen. This was lyophilized overnight to yield a white solid of C: 60.55 mg, 99.9%; LCMS result (retention time: 1.597 min (1:1 ACN: H$_2$O), surface area=100% at 214 nm; Sought 587, observed M+H=588); $^1$H NMR structure confirmed.

124

Example 32

(3R,5R)-7-[3-(Azetidine-1-sulfonyl)-5-(4-fluoro-phenyl)-2-isopropyl-4-phenyl-pyrrol-1-yl]-3,5-dihydroxy-heptanoic acid sodium salt

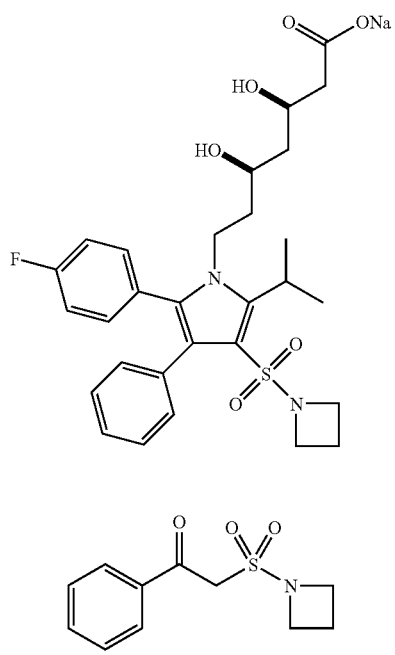

Step A 2-(Azetidine-1-sulfonyl)-1-phenyl-ethanone

To a THF solution (30 mL) containing Azetidine methanesulfonamide (2.0 g) at −78° C. was dropwise added n-butyllithium (6.4 mL of 2.5 M in Hexane). The reaction mixture was then warmed to 0° C. and cooled back to −78° C. before methyl benzoate (2.01 g in THF (5 mL)) was dropwise added. The reaction mixture was stirred for 1 h after the dry ice bath was removed. Work-up: The reaction mixture was acidified with 1N HCl (5 mL) and then concentrated under reduced pressure. The resultant material was extracted with EtOAc, and the org. phase was washed with water, brine and dried over Na$_2$SO$_4$, filtered. The filtrate was then evaporated under reduced pressure to yield a pale yellow liquid (2.95 g, crude). The crude material was then purified by column chromatography (a 4:1 mixture of Hex. and EtOAc as eluent) to give a transparent liquid (2.30 g). MS, APCI+240.0 (M+H); $^1$H NMR spectrum (400 MHz, CDCl$_3$) δ 7.90 (d, J=7.6 Hz, 2H), 7.65 (m, 3H), 4.13 (dd, J=7.9 Hz, J=7.80 Hz, 4H), 2.75 (s, 2H), 1.730 (m, 2H).

Step B

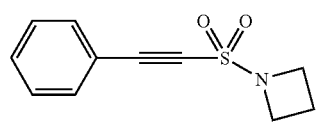

1-(2-Phenyl-ethynesulfonyl)-azetidine

Dry triethylamine (7.5 mL) was slowly added to a DCM solution (10 mL) containing the ketosulfonamide from Step A and N-methylpyridinium Iodide at ambient temperature.

The suspension was stirred at room temperature for 2 days. To take a TLC a small aliquot of the sample was treated with 1 N NaOH, extracted with DCM. The TLC spot was taken from the org. phase. Work-Up: After 2 days, the suspension was treated with 1N NaOH (5 mL) for 5 min. Then it was extracted with DCM (20 mL×2). This organic phase was successively washed with 1N NaOH, 1N HCl, water, and dried over Na2SO4, and filtered. The filtrate was then passed through a short column of basic alumina. The resultant DCM solution was then evaporated under reduced pressure to give a yellow solid. MS, APCI+222.1 (M+H); $^1$H NMR spectrum (400 MHz, CDCl$_3$) δ 7.65 (d, J=7.6 Hz, 2H), 7.50 (m, 1H), 7.43 (m, 2H), 4.13 (dd, J=7.9 Hz, J=6.80 Hz, 4H), 2.30 (q, J=6.8 Hz, 2H).

Step C

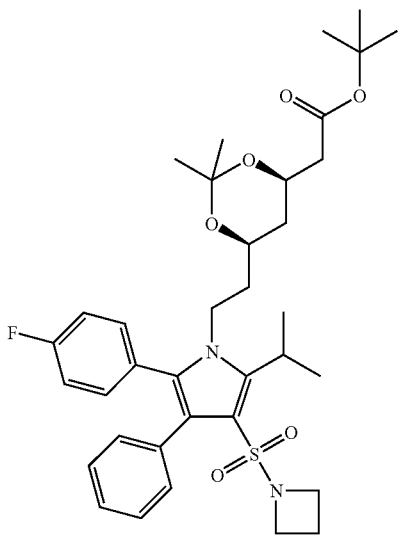

((4R,6R)-6-{2-[3-(Azetidine-1-sulfonyl)-5-(4-fluoro-phenyl)-2-isopropyl-4-phenyl-pyrrol-1-yl]-ethyl}-2,2-dimethyl-[1,3]dioxan-4-yl)-acetic acid tert-butyl ester A solution of the Munchnone acid (1.23 g), an alkynyl azetidine sulfonamide from Step B (0.50 g, 2.26 mmole) and acetic anhydride (2.3 mmole, 300 uL) in toluene (10 mL) was heated to 60° C. for 3 h. After the reaction was complete the mixture was cooled to r.t., and evaporated under reduced pressure to yield a dark-yellow amorphous material. The desired product was isolated by a column chromatography using a gradient from 0 to 30% (v/v) of EtOAC and Hex, respectively. MS, APCI+655.3 (M+H); $^1$H NMR spectrum (400 MHz, CDCl$_3$) δ 7.24-7.05 (m, 7H), 6.90 (dd, J=8.5 Hz, 8.6 Hz, 2H), 4.20-4.01 (m Hz, 4H), 3.88 (m, 1H), 3.48 (m, 4H), 2.33 (dd, J=7.1, 6.8 Hz 1H), 2.18 (dd, 6.1, 6.4 Hz, 1H), 1.90 (m, 2H), 1.45 (m, 6H), 1.40 (s, 9H), 1.29 (d, 6H).

Step D

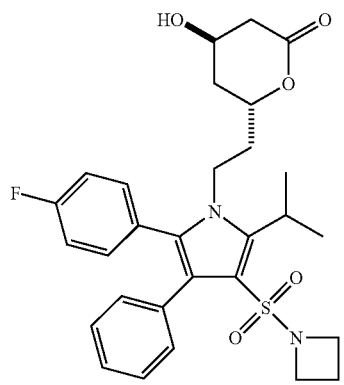

(4R,6R)-6-{2-[3-(Azetidine-1-sulfonyl)-5-(4-fluoro-phenyl)-2-isopropyl-4-phenyl-pyrrol-1-yl]-ethyl}-4-hydroxy-tetrahydro-pyran-2-one A TFA solution (30% (v/v), 15 mL) was added to the protected pyrrole from Step C (1.509 mmole) at r.t. The reaction was complete within 30 min., indicated by a new spot in TLC (Rf=0.11 in 7:3 hex:EtOAc mix). The reaction mixture was evaporated under reduced pressure, and the resultant yellow amorphous material was diluted with EtOAc (20 mL), and treated with NaHCO$_3$ (1.0 mL), washed with water (5 mL) and brine. The org. layer was then dried over Na$_2$SO$_4$, and filtered. The filtrate was subsequently evaporated under reduced pressure to give a pale yellow mat. (0.722 g, crude). The desired lactone was obtained by a column chromatography by using a gradient of 6:4 to 8:2 EtOAc: hex mix, respectively: 0.503 g. MS, APCI+541.2 (M+H); $^1$H NMR spectrum (400 MHz, CD$_3$OD) δ 7.24-7.05 (m, 7H), 6.98 (dd, J=8.5 Hz, 8.6 Hz, 2H), 4.45 (m, 1H), 4.15 (m, 2H), 3.57 (m, 4H), 2.63-2.44 (m, 2H), 1.95 (m, 2H), 1.90 (m, 2H), 1.45 (2s, 6H).

Step E (3R,5R)-7-[3-(Azetidine-1-sulfonyl)-5-(4-fluoro-phenyl)-2-isopropyl-4-phenyl-pyrrol-1-yl]-3,5-dihydroxy-heptanoic acid sodium salt To a solution containing the lactone from Step D (0.670 mmole in 10 mL THF) was dropwise added 1 N NaOH (669.75 uL, 1 equiv.) at room temperature. The reaction mixture was stirred until all lactone disappeared. The reaction was evaporated under reduced pressure and redissolved in water (2 mL). This was freeze-dried to give a white solid (377.9 mg).

MS, APCI+559.2 (M+H);

Combustion Analysis for (C$_{29}$H$_{34}$F$_1$N$_2$O$_6$S$_1$Na$_1$0.74H$_2$O):

|  | Carbon | Hydrogen | Nitrogen |
|---|---|---|---|
| Theory | 58.64 | 6.02 | 4.72 |
| Found | 58.25 | 6.01 | 4.41 |

Following a similar reaction scheme as described in the previous Example, the following compounds are a representative sample of additional final compounds synthesized.

Example 33

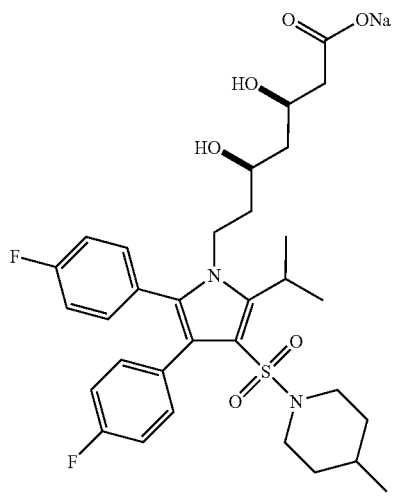

(3R,5R)-7-[2,3-Bis-(4-fluoro-phenyl)-5-isopropyl-4-(4-methyl-piperidine-1-sulfonyl)-pyrrol-1-yl]-3,5-dihydroxy-heptanoic acid sodium salt MS, APCI+619.0 (M+H);
Combustion Analysis for ($C_{32}H_{39}F_2N_2O_6S_1Na_1$ 2.05$H_2O$):

|  | Carbon | Hydrogen | Nitrogen |
| --- | --- | --- | --- |
| Theory | 56.72 | 6.41 | 4.13 |
| Found | 56.32 | 6.33 | 3.74 |

Example 34

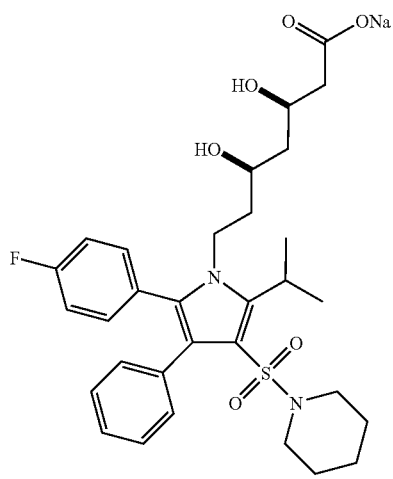

(3R,5R)-7-[2-(4-Fluoro-phenyl)-5-isopropyl-3-phenyl-4-(piperidine-1-sulfonyl)-pyrrol-1-yl]-3,5-dihydroxy-heptanoic acid sodium salt MS, APCI+587.2 (M+H);
Combustion Analysis for ($C_{31}H_{38}F_1N_2O_6S_1Na_1$ 1.81$H_2O$):

|  | Carbon | Hydrogen | Nitrogen |
| --- | --- | --- | --- |
| Theory | 58.06 | 6.54 | 4.37 |
| Found | 57.67 | 6.35 | 4.04 |

Example 35

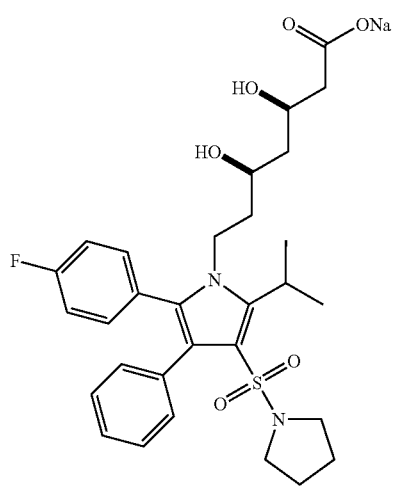

(3R,5R)-7-[2-(4-Fluoro-phenyl)-5-isopropyl-3-phenyl-4-(pyrrolidine-1-sulfonyl)-pyrrol-1-yl]-3,5-dihydroxy-heptanoic acid sodium salt MS, APCI+573.2 (M+H);
Combustion Analysis for ($C_{30}H_{36}F_1N_2O_6S_1Na_1$ 1.90$H_2O$):

|  | Carbon | Hydrogen | Nitrogen |
| --- | --- | --- | --- |
| Theory | 57.29 | 6.38 | 4.45 |
| Found | 56.90 | 6.23 | 4.09 |

Example 36

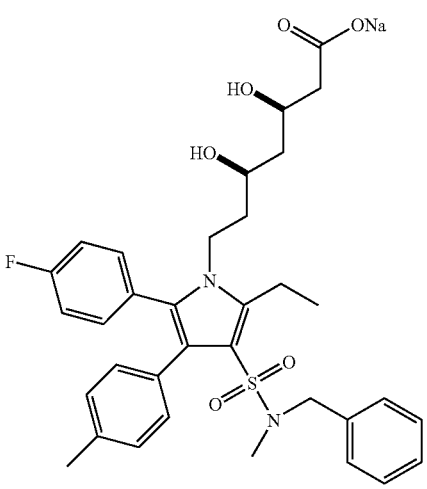

(3R,5R)-7-[3-(Benzyl-methyl-sulfamoyl-2-ethyl-5-(4-fluoro-phenyl)-4-p-tolyl-pyrrol-1-yl]-3,5-dihydroxy-heptanoic acid sodium salt

MS, APCI+623.3 (M+H);

Combustion Analysis for ($C_{34}H_{38}F_1N_2O_6S_1Na_1$ 2.68$H_2O$):

|  | Carbon | Hydrogen | Nitrogen |
|---|---|---|---|
| Theory | 58.93 | 6.31 | 4.04 |
| Found | 58.54 | 6.11 | 3.70 |

Example 37

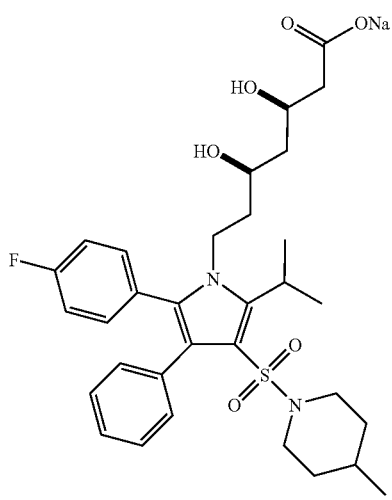

(3R,5R)-7-[2-(4-Fluoro-phenyl)-5-isopropyl-4-(4-methyl-piperidine-1-sulfonyl)-3-phenyl-pyrrol-1-yl]-3,5-dihydroxy-heptanoic acid sodium salt

MS, APCI+601.3 (M+H);

Combustion Analysis for ($C_{32}H_{40}F_1N_2O_6S_1Na_1$ 2.29$H_2O$):

|  | Carbon | Hydrogen | Nitrogen |
|---|---|---|---|
| Theory | 57.88 | 6.77 | 4.22 |
| Found | 57.72 | 6.72 | 3.82 |

Example 38

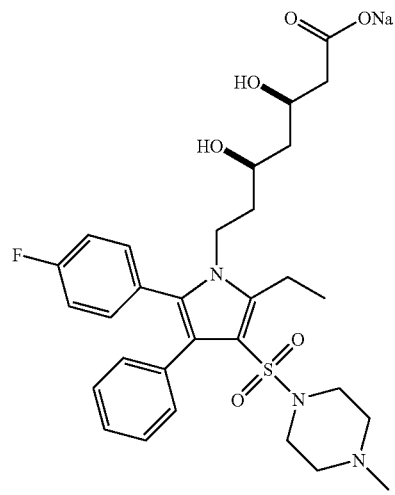

(3R,5R)-7-[2-Ethyl-5-(4-fluoro-phenyl)-3-(4-methyl-piperazine-1-sulfonyl)-4-phenyl-pyrrol-1-yl]-3,5-dihydroxy-heptanoic acid sodium salt

MS, APCI+588.1 (M+H);

Combustion Analysis for ($C_{30}H_{37}F_1N_3O_6S_1Na_1$ 2.75$H_2O$):

|  | Carbon | Hydrogen | Nitrogen |
|---|---|---|---|
| Theory | 54.66 | 6.50 | 6.37 |
| Found | 54.27 | 6.28 | 6.04 |

Example 39

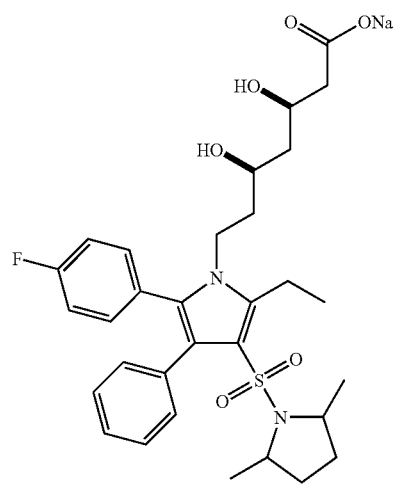

(3R,5R)-7-[3-(2,5-Dimethyl-pyrrolidine-1-sulfonyl)-2-ethyl-5-(4-fluoro-phenyl)-4-phenyl-pyrrol-1-yl]-3,5-dihydroxy-heptanoic acid sodium salt

MS, APCI+587.1 (M+H);

Combustion Analysis for ($C_{31}H_{38}F_1N_2O_6S_1Na_1$ 2.08H$_2$O):

|  | Carbon | Hydrogen | Nitrogen |
|---|---|---|---|
| Theory | 57.62 | 6.58 | 4.34 |
| Found | 57.23 | 6.35 | 4.08 |

Example 40

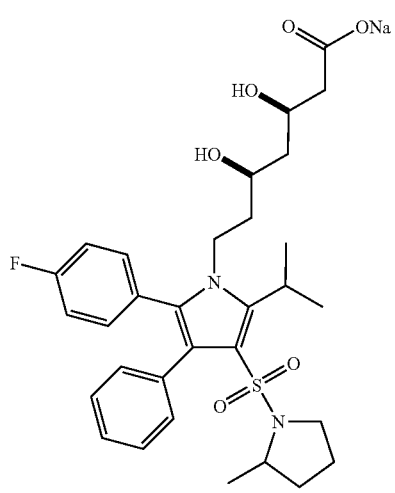

(3R,5R)-7-[2-(4-Fluoro-phenyl)-5-isopropyl-4-(2-methyl-pyrrolidine-1-sulfonyl)-3-phenyl-pyrrol-1-yl]-3,5-dihydroxy-heptanoic acid sodium salt

MS, APCI+587.3 (M+H);

Combustion Analysis for ($C_{31}H_{38}F_1N_2O_6S_1Na_1$ 1.13H$_2$O):

|  | Carbon | Hydrogen | Nitrogen |
|---|---|---|---|
| Theory | 59.19 | 6.45 | 4.45 |
| Found | 58.80 | 6.46 | 4.22 |

Example 41

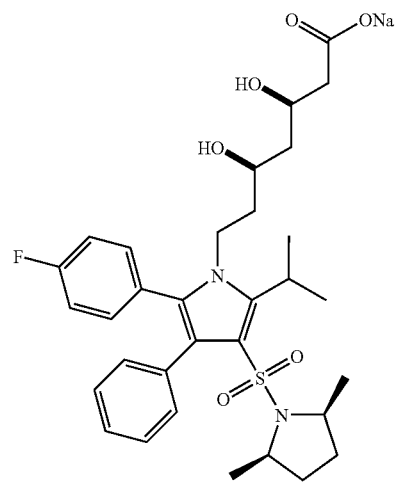

(3R,5R)-7-[3-((2S,5R)-2,5-Dimethyl-pyrrolidine-1-sulfonyl)-5-(4-fluoro-phenyl)-2-isopropyl-4-phenyl-pyrrol-1-yl]-3,5-dihydroxy-heptanoic acid sodium salt

MS, APCI+601.3 (M+H);

Combustion Analysis for ($C_{32}H_{40}F_1N_2O_6S_1Na_1$ 1.27H$_2$O):

|  | Carbon | Hydrogen | Nitrogen |
|---|---|---|---|
| Theory | 59.53 | 6.64 | 4.34 |
| Found | 59.14 | 6.66 | 4.16 |

Example 42

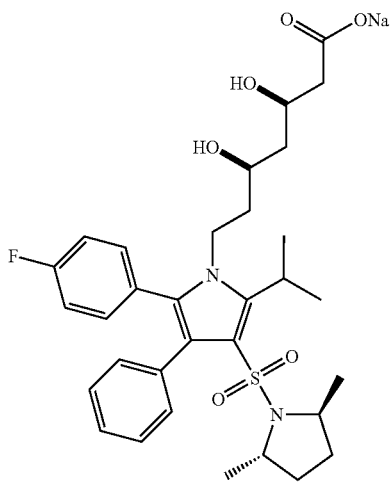

(3R,5R)-7-[3-((2S,5S)-2,5-Dimethyl-pyrrolidine-1-sulfonyl)-5-(4-fluoro-phenyl)-2-isopropyl-4-phenyl-pyrrol-1-yl]-3,5-dihydroxy-heptanoic acid sodium salt

MS, APCI+601.3 (M+H);

Combustion Analysis for (C$_{32}$H$_{40}$F$_1$N$_2$O$_6$S$_1$Na$_1$ 1.75H$_2$O):

|  | Carbon | Hydrogen | Nitrogen |
|---|---|---|---|
| Theory | 58.75 | 6.70 | 4.28 |
| Found | 58.36 | 6.44 | 3.98 |

Example 43

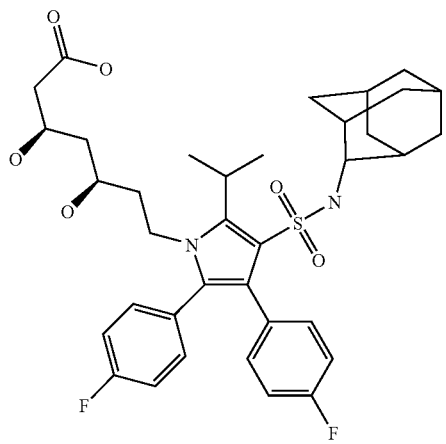

7-[3-(Adamantan-2-ylsulfamoyl)-4,5-bis-(4-fluoro-phenyl)-2-isopropyl-pyrrol-1-yl]-3,5-dihydroxy-heptanoic acid Sodium Salt MS APCI+671.2 (acid+1)

Analyzed for: C36H43F2N2Na1O6S1.2.06H2O1

|  | C | H | N |
|---|---|---|---|
| Theory | 59.24 | 6.51 | 3.84 |
| Found | 58.84 | 6.11 | 3.79 |

Example 44

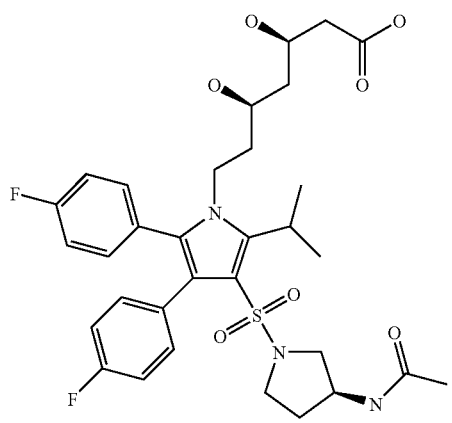

7-[3-(3-Acetylamino-pyrrolidine-1-sulfonyl)-4,5-bis-(4-fluoro-phenyl)-2-isopropyl-pyrrol-1-yl]-3,5-dihydroxy-heptanoic acid Sodium Salt MS APCI+647.1 (acid+1)
Analyzed for: C32H38F2N3Na1O7S1.040H2O1

|  | C | H | N |
|---|---|---|---|
| Theory | 56.78 | 5.78 | 6.21 |
| Found | 56.39 | 5.86 | 5.81 |

Example 45

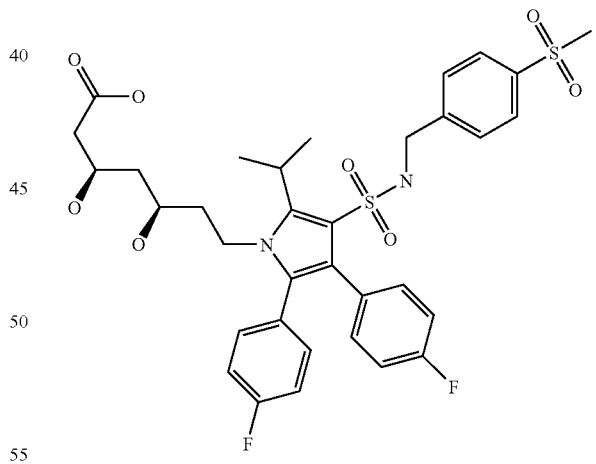

7-[2,3-Bis-(4-fluoro-phenyl)-5-isopropyl-4-(4-methanesulfonyl-benzylsulfamoyl)-pyrrol-1-yl]-3,5-dihydroxy-heptanoic acid Sodium Salt MS APCI+705.1 (acid+1)
Analyzed for: C34H37F2N2Na1O8S2.0.17C1H2Cl2

|  | C | H | N |
|---|---|---|---|
| Theory | 55.37 | 5.08 | 3.78 |
| Found | 54.98 | 5.24 | 3.65 |

Example 46

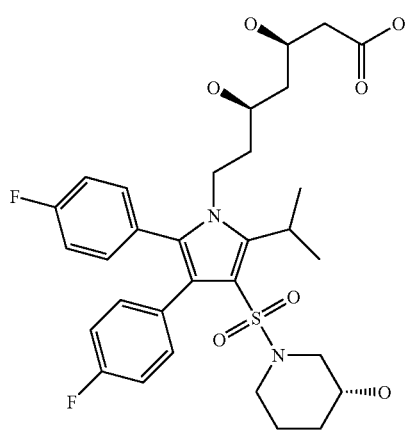

7-[2,3-Bis-(4-fluoro-phenyl)-4-(3-hydroxy-piperidine-1-sulfonyl)-5-isopropyl-pyrrol-1-yl]-3,5-dihydroxy-heptanoic acid Sodium Salt MS APCI+621.2 (acid+1)
Analyzed for: C31H37F2N2Na1O7S1.2.35H2O1

|  | C | H | N |
|---|---|---|---|
| Theory | 54.35 | 6.14 | 4.09 |
| Found | 54.61 | 5.74 | 3.69 |

Example 47

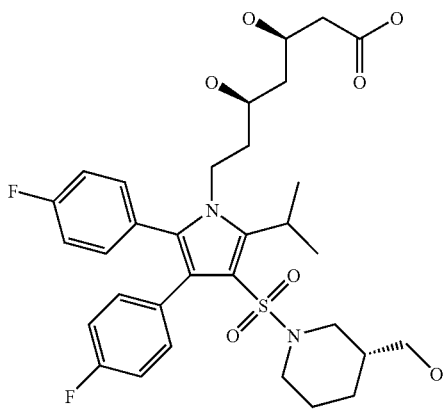

7-[2,3-Bis-(4-fluoro-phenyl)-4-(3-hydroxymethyl-piperidine-1-sulfonyl)-5-isopropyl-pyrrol-1-yl]-3,5-dihydroxy-heptanoic acid Sodium Salt MS APCI+635.2 (acid+1)
Analyzed for: C32H39F2N2Na1O7S1.1.29H2O1

|  | C | H | N |
|---|---|---|---|
| Theory | 56.52 | 6.16 | 4.12 |
| Found | 56.13 | 6.07 | 3.89 |

Example 48

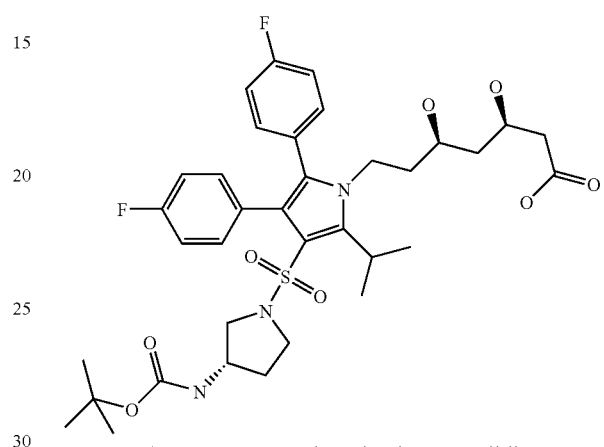

7-[3-(3-tert-Butoxycarbonylamino-pyrrolidine-1-sulfonyl)-4,5-bis-(4-fluoro-phenyl)-2-isopropyl-pyrrol-1-yl]-3,5-dihydroxy-heptanoic acid Sodium Salt MS APCI+706.2 (acid+1)
Analyzed for: C35H44F2N3Na1O8S1.2.07H2O1

|  | C | H | N |
|---|---|---|---|
| Theory | 54.94 | 6.34 | 5.49 |
| Found | 54.55 | 6.03 | 5.25 |

Example 49

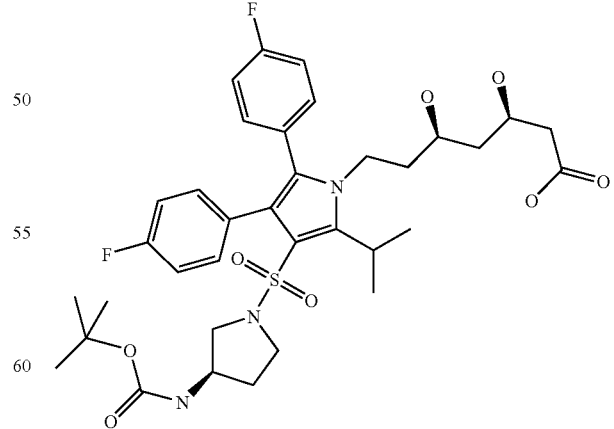

7-[3-(3-tert-Butoxycarbonylamino-pyrrolidine-1-sulfonyl)-4,5-bis-(4-fluoro-phenyl)-2-isopropyl-pyrrol-1-yl]-3,5-dihydroxy-heptanoic acid Sodium Salt MS APCI+706.1 (acid+1)
Analyzed for: C35H44F2N3Na1O8S1.0.96H2O1

|  | C | H | N |
|---|---|---|---|
| Theory | 56.42 | 6.21 | 5.64 |
| Found | 56.03 | 6.12 | 5.30 |

Example 50

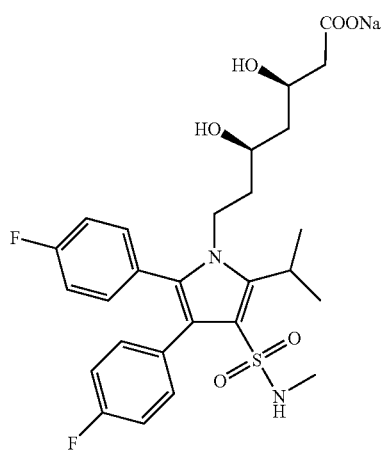

MP: 140-143° C.
Combustion Analysis: (C27H31F2N2Na1O6S1.0.35C4H10O1 (ethyl ether). 1.7H2O1):

|  | Carbon | Hydrogen | Nitrogen | F |
|---|---|---|---|---|
| Theory | 54.22 | 6.07 | 4.45 | 6.04 |
| Found | 54.33 | 5.71 | 4.06 | 6.10 |

Example 51

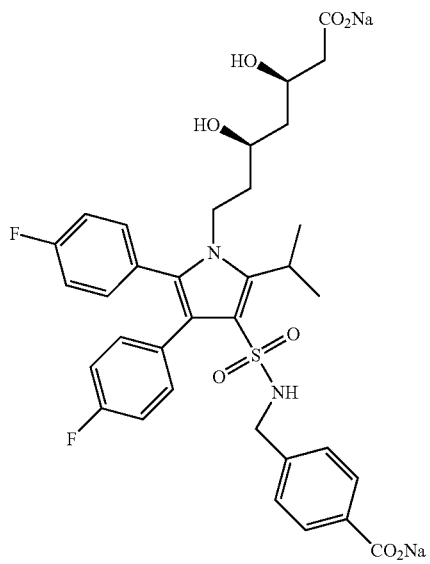

MS showed the di-acid peak APCI+ (671.2, acid+H). MP>250° C.

Combustion Analysis for (C34H34F2N2Na2O8S1.4.0H2O1.1.60 NaOH):

|  | Carbon | Hydrogen | Nitrogen |
|---|---|---|---|
| Theory | 48.00 | 5.17 | 3.29 |
| Found | 47.76 | 4.78 | 2.92 |

Formulations

The compounds of the present invention including those exemplified herein and all compounds of Formula I, hereafter referred to as "compound(s)" can be administered alone or in combination with one or more therapeutic agents. These include, for example, other agents for treating, preventing or controlling dyslipidemia, non-insulin dependent diabetes mellitus, obesity, hyperglycemia, hypercholesteremia, hyperlipidemia, atherosclerosis, hypertriglyceridemia, or hyperinsulinemia.

The compounds are thus well suited to formulation for convenient administration to mammals for the prevention and treatment of such disorders.

The following examples further illustrate typical formulations of the compounds provided by the invention.

| Formulation 1 | |
|---|---|
| Ingredient | Amount |
| compound | 0.5 to 800 mg |
| sodium benzoate | 5 mg |
| isotonic saline | 1000 mL |

The above ingredients are mixed and dissolved in the saline for IV administration to a patient.

| Formulation 2 | |
|---|---|
| Ingredient | Amount |
| compound | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a patient.

Formulation 3

| Ingredient | Amount |
| --- | --- |
| compound | 0.5 to 800 mg |
| starch, dried | 250 mg |
| magnesium stearate | 10 mg |

The ingredients are combined and milled to afford material suitable for filling hard gelatin capsules administered to a patient.

Formulation 4

| Ingredient | Amount % wt./ (total wt.) |
| --- | --- |
| compound | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

Biological Assays

The compounds of the invention have demonstrated HMG Co-A reductase inhibition in standard assays commonly employed by those skilled in the art. (See, e.g., J. of Lipid Research 1998; 39:75-84; Analytical Biochemistry, 1991; 196:211-214; RR 740-01077 Pharmacology 8-Nov.-82) Accordingly, such compounds and formulations comprising such compounds are useful for treating, controlling or preventing inter alia hypercholesterolemia, hyperlipidemia, hypertriglyceridemia or atherosclerosis.

A.) In Vitro assay

Rat Liver Microsomal Isolation Procedure: Male Charles River Sprague-Dawley rats were fed with 2.5% cholestyramine in rat chow diets for 5 days before sacrificing. Livers were minced and homogenized in a sucrose homogenizing solution in an ice bath 10 times. Homogenates were diluted into a final volume of 200 mL and centrifuged 15 min. with a Sorvall Centrifuge at 5° C., 10,000 rpm (12,000×G). The upper fat layer was removed and the supernatant decanted into fresh tubes. This step was repeated one more time before transferring the supernatant into ultracentrifuge tubes and centrifuged at 36,000 rpm (105,000×G) for an hour at 5° C. The resulting supernatant was discarded and the pellet was added to total of 15 mL 0.2 M $KH_2PO_4$. Pellets were homogenized gently by hand about 10 times. Samples were pooled and diluted into total of 60 mL buffer. The protein concentration of the homogenate was determined by the Lowry Method using a BCA kit from Pierce Chemical Company. 1 mL aliquots of microsomes were kept frozen in liquid nitrogen.

HMGCoA (3-Hydroxy-3-methylglutaryl CoA) Reductase Assay:

Materials and Methods:

[3-$^{14}$C]-HMGCoA (57.0 mCi/mmol) was purchased from Amersham Biosciences, UK. HMGCoA, mevalonolactone, NADPH were purchased from Sigma Chemical Co. AG 1-8× resin was purchased from Bio-Rad Laboratory.

One µL of dimethyl sulfoxide (DMSO) or 1 µL of DMSO containing a test compound at a concentration sufficient to give a final assay concentration of between 0.1 nM to 1 mM was placed into each well of a Corning 96 well plate. A Volume of 34 µL of buffer (100 mM $NaH_2PO_4$, 10 mM Imidazole and 10 mM EDTA) containing with 50 µg/mL rat liver microsomes was added into each well. After incubation for 30 min. on ice, 15 µL of $^{14}$C-HMGCoA (0.024 µCi) with 15 mM NADPH, 25 mM DTT was added and incubated at 37° C. for an additional 45 min. The reaction was terminated by the addition of 10 µL of HCl followed by 5 µL of mevalonolactone. Plates were incubated at room temperature overnight to allow lactonization of mevalonate to mevalonolactone. The incubated samples were applied to columns containing 300 µL of AG1-X8 anion exchange resin in a Corning filter plate. The eluates were collected into Corning 96 well capture plates. Scintillation cocktail (Ultima-Flo-M) was added into each well and plates counted on a Trilux Microbeta Counter. The $IC_{50}$ values were calculated with GraphPad software (Prism).

Procedure:
1. Add 1 µL DMSO or compounds into the wells according to the protocol
2. Add 35 µL incubation buffer with the rat microsomes into each well. Incubate 30 min. at 4° C.
3. Add 15 µL $^{14}$C-HMGCoA. Incubate 45 min. at 37° C.
4. Add 10 µL HCl stop reagent
5. Add 5 µL mevelonolactone. Incubate overnight at room temperature
6. Apply the containing into the AG 1-X8 anion exchange resin in Corning filter plate
7. Collect the eluate into Corning capture plate
8. Add scintillation cocktail Ultima-Flo-M
9. Count on a Trilux Microbeta Counter
10. Calculate $IC_{50}$ values Compounds of the invention exhibit a range of $IC_{50}$ values of less than about 1000 nM. Preferred compounds of the invention exhibit a range of $IC_{50}$ values of less than about 100 nM. More preferred compounds of the invention exhibit a range of $IC_{50}$ values of less than about 20 nM.

B.) Cell Assay

Protocol for Sterol Biosynthesis in Rat Hepatocytes:

Cell culture, Compounds Treatment and Cell Labeling:

Frozen rat hepatocytes purchased from XenoTech (cat# N400572) were seeded on 6-well collagen I coated plates at a density of $10^5$ cells/per well. The cells were grown in DMEM medium (Gibco, #11054-020) containing 10% FBS and 10 mM HEPES (Gibco # 15630-080) for 24 hrs. The cells were pre-incubated with compounds for 4 hrs and then labeled by incubating in medium containing 1 uCi/per ml of $^{14}$C acetic acid for an additional 4 hrs. After labeling, the cells were washed twice with 5 mM MOPS solution containing 150 mM NaCl and 1 mM EDTA and collected in the lysis buffer containing 10% KOH and 80% (vol.) ethanol.

Cholesterol Extraction and Data Analysis:

In order to separate labeled cholesterol from labeled non-cholesterol lipids, the cells lysates were subject to saponification at 60° C. for 2 hrs. The lysates were then combined with 0.5 volume of $H_2O$ and 2 volumes of hexane, followed by 30 minutes of vigorous shaking. After the separation of two phases, the upper-phase solution was collected and combined with 5 volumes of scintillation cocktail. The amount of $^{14}C$ cholesterol was quantified by liquid scintillation counting. The $IC_{50}$ values were calculated with GraphPad software (Prism 3.03).

Compounds of the invention exhibit a range of $IC_{50}$ values of less than about 100 nM. Preferred compounds of the invention exhibit a range of $IC_{50}$ values of less than about 10 nM.

What is claimed is:
1. A compound of Formula I,

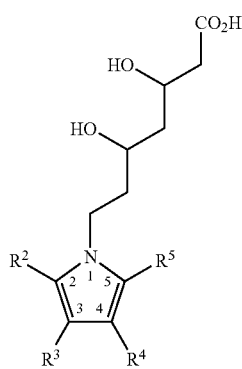

Formula I.

or a pharmaceutically acceptable salt, ester, amide, stereoisomer or prodrug thereof, or a pharmaceutically acceptable salt of the prodrug, wherein:

$R^2$ is benzyl, naphthyl or cyclohexyl, optionally substituted; or phenyl optionally substituted with fluorine, chlorine, bromine, hydroxyl or trifluoromethyl; pyridinyl or pyridinyl substituted with fluorine, chlorine, bromine, hydroxyl or trifluoromethyl; or alkyl of from one to seven carbon atoms;

One of $R^3$ and $R^4$ is H; aryl, aralkyl, optionally substituted; $C_1$-$C_8$ alkyl straight chain or branched; or $C_3$-$C_8$ cycloalkyl; and the other one of $R^3$ and $R^4$ is I, COOR', $R^6R^7NC(O)$— or $SO_2NR^9R^{10}$;

One of $R^6$ and $R^7$ is $SO_2NHR^8$ or $SO_2R^8$; and the other one of $R^6$ and $R^7$ is H or $C_1$-$C_4$ alkyl;

$R^8$ is aryl, optionally substituted;

$R^9$ and $R^{10}$ are each independently H; aryl, aralkyl, optionally substituted with halogen, OR', $(CH_2)_n$COOR', $(CH_2)_n$CONR'R'', $(CH_2)_n$SO_2NR'R'', $(CH_2)_n$SO_2R'$ or CN; $C_1$-$C_{10}$ alkyl unsubstituted or substituted with OH, $CO_2R'$ or CONR'R'';

$R^5$ is alkyl of from one to four carbon atoms, optionally substituted with a halogen;

R' and R'' are each independently H, lower alkyl or taken together form a 4-7 member ring;

and n is 0-2, with a proviso when $R^2$ is phenyl substituted with fluorine, $R^5$ is alkyl, $R^4$ is aryl and $R^3$ is COOR', then R' is not H or lower alkyl.

2. A compound of claim 1 or the pharmaceutically acceptable salt, ester, amide, stereoisomer or prodrug thereof, or the pharmaceutically acceptable salt of the prodrug, wherein $R^2$ is phenyl or substituted phenyl.

3. A compound of claim 2 or the pharmaceutically acceptable salt, ester, amide, stereoisomer or prodrug thereof, or the pharmaceutically acceptable salt of the prodrug, wherein $R^2$ is phenyl substituted with a halogen.

4. A compound of claim 3 or the pharmaceutically acceptable salt, ester, amide, stereoisomer or prodrug thereof, or the pharmaceutically acceptable salt of the prodrug, wherein $R^2$ is para-fluorophenyl.

5. A compound of claim 1 or the pharmaceutically acceptable salt, ester, amide, stereoisomer or prodrug thereof, or the pharmaceutically acceptable salt of the prodrug, wherein $R^3$ is phenyl, biphenyl or substituted phenyl, lower alkyl, or naphthyl.

6. A compound of claim 1 or the pharmaceutically acceptable salt, ester, amide, stereoisomer or prodrug thereof, or the pharmaceutically acceptable salt of the prodrug, wherein $R^3$ is cyclohexyl-, cyclopentyl-, cyclobutyl-, cyclopropyl-, methyl-, ethyl-, isopropyl-, difluoromethyl, trifluoro-methyl or phenyl substituted with one or more halogen.

7. A compound of claim 5 or the pharmaceutically acceptable salt, ester, amide, stereoisomer or prodrug thereof, or the pharmaceutically acceptable salt of the prodrug, wherein $R^3$ is para-fluorophenyl, 3,4-difluorophenyl, para-cyanophenyl or para-methylphenyl.

8. A compound of claim 1 or the pharmaceutically acceptable salt, ester, amide, stereoisomer or prodrug thereof, or the pharmaceutically acceptable salt of the prodrug, wherein $R^5$ is $C_1$-$C_4$ alkyl.

9. A compound of claim 8 or the pharmaceutically acceptable salt, ester, amide, stereoisomer or prodrug thereof, or the pharmaceutically acceptable salt of the prodrug, wherein $R^5$ is $C_{1-3}$ alkyl.

10. A compound of claim 1 or the pharmaceutically acceptable salt, ester, amide, stereoisomer or prodrug thereof, or the pharmaceutically acceptable salt of the prodrug, wherein $R^4$ is $SO_2NR^9R^{10}$.

11. A compound of claim 10 or the pharmaceutically acceptable salt, ester, amide, stereoisomer or prodrug thereof, or the pharmaceutically acceptable salt of the prodrug, wherein $R^9$ and $R^{10}$ are each independently H, methyl, phenyl or phenyl substituted with OH, F, $CO_2R'$, CONR'R'', $SO_2NR'R''$ or one or more halogen; or benzyl or benzyl substituted with OH, $CO_2R'$ or CONR'R''.

12. A compound of claim 1 or the pharmaceutically acceptable salt, ester, amide, stereoisomer or prodrug thereof, or the pharmaceutically acceptable salt of the prodrug, wherein $R^5$ is isopropyl, ethyl, trifluoromethyl or difluoromethyl.

13. A compound of claim 12 or the pharmaceutically acceptable salt, ester, amide, stereoisomer or prodrug thereof, or the pharmaceutically acceptable salt of the prodrug, wherein $R^5$ is isopropyl and $R^2$ is para-fluorophenyl.

14. A pharmaceutically acceptable salt of a compound of claim 1 wherein the salt is a sodium salt or a calcium salt.

15. A sterioisomer of a compound of claim 1 is a (3R, 5R)-isomer or the pharmaceutically acceptable salt, ester or amide thereof.

16. A sterioisomer of a compound of claim 1 is a (3S, 5R)-isomer or the pharmaceutically acceptable salt, ester or amide thereof.

17. A sterioisomer of a compound of claim 1 is a (3R, 5S)-isomer or the pharmaceutically acceptable salt, ester or amide thereof.

18. A sterioisomer of a compound of claim 1 is a (3S, 5S)-isomer or the pharmaceutically acceptable salt, ester or amide thereof.

19. A pharmaceutically acceptable ester of claim 1 wherein the ester is a methyl ester.

20. A compound of claim 9 wherein $R^5$ is isopropyl.

21. A compound of claim 1 or the pharmaceutically acceptable salt, ester, amide, stereoisomer or prodrug thereof, or the pharmaceutically acceptable salt of the prodrug, wherein $R^2$ and $R^3$ are each independently phenyl or substituted phenyl and $R^5$ is $C_1$-$C_4$ alkyl.

22. A compound of claim 21 or the pharmaceutically acceptable salt, ester, amide, stereoisomer or prodrug thereof, or the pharmaceutically acceptable salt of the prodrug, wherein $R^4$ is $SO_2NR^9R^{10}$.

23. A compound of claim 22 or the pharmaceutically acceptable salt, ester, amide, stereoisomer or prodrug thereof, or the pharmaceutically acceptable salt of the prodrug, wherein $R^9$ and $R^{10}$ are each independently H, Me, phenyl substituted with OH, F, $CO_2R$, $SO_2NR'R''$ or CONR'R'', benzyl or benzyl substituted with OH, F, $CO_2R'$ or CONR''.

24. A compound of claim 1 or the pharmaceutically acceptable salt, ester, amide, stereoisomer or prodrug thereof, or the pharmaceutically acceptable salt of the prodrug, wherein $R^8$ is phenyl or substituted phenyl.

25. A compound selected from the group consisting of: (3R,5R)-7-[2,3-Bis-(4-fluoro-phenyl)-5-isopropyl-4-methylsulfamoyl-pyrrol-1-yl]-3,5-dihydroxy-heptanoic acid; (3R,5R)-7-[2,3-Bis-(4-fluoro-phenyl)-5-isopropyl-pyrrol-1-yl]-3,5-dihydroxy-heptanoic acid; (3R,5R)-7-[3-Benzylsulfamoyl-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-4-(2-hydroxy-phenylsulfamoyl)-5-isopropyl-pyrrol-1-yl]-3,5-dihydroxy-heptanoic acid; (3R,5R)-7-[2,3-Bis-(4-fluoro-phenyl)-5-isopropyl-4-phenylsulfamoyl-pyrrol-1-yl]-3,5-dihydroxy-heptanoic acid; 4-[1-((3R,5R)-6-Carboxy-3,5-dihydroxy-hexyl)-4,5-bis-(4-fluoro-phenyl)-2-isopropyl-1H-pyrrole-3-sulfonylamino]-benzoic acid; (3R,5R)-7-[2,3-Bis-(4-fluoro-phenyl)-5-isopropyl-4-(2-methoxycarbonyl-ethylsulfamoyl)-pyrrol-1-yl]-3,5-dihydroxy-heptanoic acid; (3R,5R)-7-[2,3-Bis-(4-fluoro-phenyl)-5-isopropyl-4-(3-methoxycarbonyl-propylsulfamoyl)-pyrrol-1-yl]-3,5-dihydroxy-heptanoic acid; (3R,5R)-7-[3-(2,4-Difluoro-phenylsulfamoyl)-4,5-bis-(4-fluoro-phenyl)-2-isopropyl-pyrrol-1-yl]-3,5-dihydroxy-heptanoic acid; (3R,5R)-7-[3-Carbamoyl-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-5-isopropyl-4-(toluene-4-sulfonylaminocarbonyl)-pyrrol-1-yl]-3,5-dihydroxy-heptanoic acid; and (3R,5R)-7-[2,3-Bis-(4-fluoro-phenyl)-4-(2-hydroxy-ethylsulfamoyl)-5-isopropyl-pyrrol-1-yl]-3,5-dihydroxy-heptanoic acid; and pharmaceutically acceptable salts, esters, and amides thereof.

26. A compound of claim 23 or the pharmaceutically acceptable salt, ester, amide, stereoisomer or prodrug thereof, or the pharmaceutically acceptable salt of the prodrug, wherein $R^9$ and $R^{10}$ are each independently H, Me, phenyl or phenyl substituted with OH or benzyl.

27. A compound selected from the group consisting of: 4-{[1-((3R,5R)-6-Carboxy-3,5-dihydroxy-hexyl)-5-(4-fluoro-phenyl)-2-isopropyl-4-phenyl-1H-pyrrole-3-carbonyl]-amino}-benzoic acid; 4-{[1-((3R,5R)-6-Carboxy-3,5-dihydroxy-hexyl)-5-(4-fluoro-phenyl)-2-isopropyl-4-phenyl-1H-pyrrole-3-carbonyl]-amino}-benzoic acid; (3R,5R)-7-[2,3-Bis-(4-fluoro-phenyl)-4-(2-hydroxy-phenylsulfamoyl)-5-isopropyl-pyrrol-1-yl]-3,5-dihydroxy-heptanoic acid; and (3R,5R)-7-[3-(4-Dimethylcarbamoyl-phenylcarbamoyl)-5-(4-fluoro-phenyl)-2-isopropyl-4-phenyl-pyrrol-1-yl]-3,5-dihydroxy-heptanoic acid; and pharmaceutically acceptable salts, esters and amides thereof.

28. A compound selected from the group consisting of: (3R,5R)-7-[2-(4-Fluoro-phenyl)-4-iodo-5-isopropyl-3-phenyl-pyrrol-1-yl]-3,5-dihydroxy-heptanoic acid; (3R,5R)-7-[4-Benzylcarbamoyl-2-(4-fluoro-phenyl)-5-isopropyl-imidazol-1-yl]-3,5-dihydroxy-heptanoic acid; (3R,5R)-7-[2,3-Bis-(4-fluoro-phenyl)-4-(2-fluoro-phenylsulfamoyl)-5-isopropyl-pyrrol-1-yl]-3,5-dihydroxy-heptanoic acid; (3R,5R)-7-[2,3-Bis-(4-fluoro-phenyl)-4-(3-hydroxy-phenylsulfamoyl)-5-isopropyl-pyrrol-1-yl]-3,5-dihydroxy-heptanoic acid; (3R,5R)-7-[3-(4-Carbamoyl-phenylsulfamoyl)-4,5-bis-(4-fluoro-phenyl)-2-isopropyl-pyrrol-1-yl]-3,5-dihydroxy-heptanoic acid; and (3R,5R)-7-[2,3-Bis-(4-fluoro-phenyl)-5-isopropyl-4-(4-sulfamoyl-phenylsulfamoyl)-pyrrol-1-yl]-3,5-dihydroxy-heptanoic acid; and pharmaceutically acceptable salts, amides and esters thereof.

29. A compound selected from the group consisting of: (3R,5R)-7-[3-(Benzyl-methyl-sulfamoyl)-4,5-bis-(4-fluoro-phenyl)-2-isopropyl-pyrrol-1-yl]-3,5-dihydroxy-heptanoic acid; (3R,5R)-7-[3-(Benzyl-methyl-sulfamoyl)-5-(4-fluoro-phenyl)-2-isopropyl-4-p-tolyl-pyrrol-1-yl]-3,5-dihydroxy-heptanoic acid; and (3R,5R)-7-[3-(Benzyl-methyl-sulfamoyl)-5-(4-fluoro-phenyl)-2-isopropyl-4-naphthalen-2-yl-pyrrol-1-yl]-3,5-dihydroxy-heptanoic acid; and pharmaceutically acceptable salts, esters and amides thereof.

30. A compound selected from the group consisting of: (3R,5R)-7-[2-ethyl-4-(2-methoxy-ethylcarbamoyl)-3-4-methoxy-phenyl)-5-methyl-pyrrol-1-yl]-3,5-dihydroxy-heptanoic acid; (3R,5R)-7-[2-ethyl-4-(2-methoxy-ethylcarbamoyl)-5-methyl-3-naphthalen-2-yl-pyrrol-1-yl]-3,5-dihydroxy-heptanoic acid; and pharmaceutically acceptable salts, esters and amides thereof.

31. A compound selected from the group consisting of: (3R,5R)-3,5-Dihydroxy-7-(3-isobutylcarbamoyl-2,5-dimethyl-4-phenyl-pyrrol-1-yl)-heptanoic acid; (3R,5R)-3,5-Dihydroxy-7-(3-isobutylcarbamoyl-2,5-dimethyl-4-p-tolyl-pyrrol-1-yl)-heptanoic acid; (3R,5R)-7-(2-Ethyl-4-isobutylcarbamoyl-5-methyl-3-p-tolyl-pyrrol-1-yl)-3,5-dihydroxy-heptanoic acid; (3R,5R)-7-(2,5-Dimethyl-3-phenethylcarbamoyl-4-p-tolyl-pyrrol-1-yl)-3,5-dihydroxy-heptanoic acid; (3R,5R)-7-(2-benzyl-5-methyl-3-phenyl-4-phenylcarbamoyl-pyrrol-1-yl)-3,5-dihydroxy-heptanoic acid; (3R,5R)-7-[3-(4-Chloro-phenyl)-5-isopropyl-2-methyl-4-phenylcarbamoyl-pyrrol-1-yl]-3,5-dihydroxy-heptanoic acid; and (3R,5R)-3,5-Dihydroxy-7-(2-methyl-4,5-diphenyl-3-phenylcarbamoyl-pyrrol-1-yl)-heptanoic acid; and pharmaceutically acceptable salts, amides and esters thereof.

32. A pharmaceutical composition comprising a compound of claim 1, the pharmaceutically acceptable salt, ester, amide or prodrug thereof, or the pharmaceutically acceptable salt of the prodrug; and a pharmaceutically acceptable carrier, diluent, or vehicle.

33. A compound selected from the group consisting of: (3R,5R)-7-[2-(4-fluoro-phenyl)-4-iodo-5-isopropyl-3-phenyl-pyrrol-1-yl]-3,5-dihydroxy-heptanoic acid; (3R,5R)-7-[3-(4-Carbamoyl-phenylsulfamoyl)-4,5-bis-(4-fluoro-phenyl)-2-isopropyl-pyrrol-1-yl]-3,5-dihydroxy-heptanoic acid; (3R,5R)-7-[2,3-Bis-(4-fluoro-phenyl)-5-isopropyl-4-(4-sulfamoyl-phenylsulfamoyl)-pyrrol-1-yl]-3,5-dihydroxy-heptanoic acid; (3R,5R)-7-[3-(Benzyl-methyl-sulfamoyl)-5-(4-fluoro-phenyl)-2-isopropyl-4-naphthalen-2-yl-pyrrol-1-yl]-3,5-dihydroxy-heptanoic acid; and pharmaceutically acceptable salts, esters and amides thereof.

34. A racemic mixture of a compound of claim 1.

* * * * *